(12) United States Patent
Watterson et al.

(10) Patent No.: US 8,063,047 B2
(45) Date of Patent: Nov. 22, 2011

(54) PYRIDAZINE COMPOUNDS AND METHODS

(75) Inventors: Martin Watterson, Chicago, IL (US); Linda Van El Dik, Chicago, IL (US); Jacques Haiech, Strasbourg (FR); Marcel Hibert, Eschau (FR); Jean-Jacques Bourguignon, Illkirch (FR); Anastasia Veleniza, San Diego, CA (US); Wenhui Hu, Guangzhou (CN); Magdaena Zasadzki, Chicago, IL (US)

(73) Assignees: Centre National de la Recherche Scientifique (CNRS), Paris (FR); Northwestern University, Evanston, IL (US); Universite de Strasbourg, Strasbourg (FR)

( * ) Notice: Subject to any disclaimer, the term of this patent is extended or adjusted under 35 U.S.C. 154(b) by 368 days.

(21) Appl. No.: 12/119,208

(22) Filed: May 12, 2008

(65) Prior Publication Data

US 2009/0029985 A1 Jan. 29, 2009

Related U.S. Application Data

(63) Continuation of application No. 11/666,872, filed on May 1, 2007, now abandoned.

(60) Provisional application No. 60/624,346, filed on Nov. 2, 2004, provisional application No. 60/723,376, filed on Oct. 4, 2005.

(51) Int. Cl.
| | |
|---|---|
| C07D 237/26 | (2006.01) |
| A61K 31/502 | (2006.01) |
| A61P 29/00 | (2006.01) |
| A61P 25/04 | (2006.01) |
| A61P 25/28 | (2006.01) |
| A61P 25/16 | (2006.01) |
| A61P 25/24 | (2006.01) |
| A61P 25/18 | (2006.01) |

(52) U.S. Cl. ........................ 514/248; 544/234
(58) Field of Classification Search .................. 544/234; 514/248
See application file for complete search history.

(56) References Cited

U.S. PATENT DOCUMENTS

| | | | |
|---|---|---|---|
| 2,857,384 A | 10/1958 | Druey, J. et al. | |
| 3,464,988 A * | 9/1969 | Holava, Jr. et al. ........... | 544/234 |
| 4,169,158 A | 9/1979 | Laborit | |
| 4,508,720 A | 4/1985 | Kan et al. | |
| 4,562,196 A | 12/1985 | Horn et al. | |
| 4,631,286 A | 12/1986 | Shutske et al. | |
| 4,654,343 A | 3/1987 | Albright et al. | |
| 4,710,499 A | 12/1987 | Wermuth et al. | |
| 4,721,711 A | 1/1988 | Chambon et al. | |
| 4,754,050 A | 6/1988 | Shutske et al. | |
| 4,755,511 A * | 7/1988 | Warrington .................... | 514/248 |
| 4,816,456 A | 3/1989 | Summers | |
| 4,835,275 A | 5/1989 | Shutske et al. | |
| 4,839,364 A | 6/1989 | Shutske et al. | |
| 4,895,841 A | 1/1990 | Sugimoto et al. | |
| 4,948,807 A | 8/1990 | Rosin et al. | |
| 4,977,152 A * | 12/1990 | Biziere et al. .............. | 514/232.8 |
| 5,045,541 A * | 9/1991 | Nakao et al. .................. | 514/248 |
| 5,100,901 A | 3/1992 | Sugimoto et al. | |
| 5,104,880 A | 4/1992 | Kozikowski | |
| 5,484,490 A | 1/1996 | Tokita et al. | |
| 5,554,780 A | 9/1996 | Wolf | |
| 5,693,668 A | 12/1997 | Schirlin et al. | |
| 5,760,267 A | 6/1998 | Gandolfi et al. | |
| 5,929,084 A | 7/1999 | Zhu et al. | |
| 6,194,403 B1 | 2/2001 | Hu et al. | |
| 2003/0176437 A1 | 9/2003 | Watterson et al. | |
| 2005/0137397 A1 | 6/2005 | Nelson | |
| 2005/0143381 A1 | 6/2005 | Yu et al. | |
| 2005/0192278 A1 | 9/2005 | Ewing et al. | |
| 2006/0073472 A1 | 4/2006 | Watterson et al. | |
| 2008/0021035 A1 | 1/2008 | Watterson et al. | |

(Continued)

FOREIGN PATENT DOCUMENTS

EP 0072726 A2 2/1983

(Continued)

OTHER PUBLICATIONS

Griesser, in Chapter 8, The Importance of Solvates (pp. 211-230), in the text, Polymorphism: In the Pharmaceutical Industry, Hilfiker, 2006.*

(Continued)

*Primary Examiner* — James O Wilson
*Assistant Examiner* — Cecilia M Jaisle
(74) *Attorney, Agent, or Firm* — Millen, White, Zelano & Branigan, P.C.

(57) ABSTRACT

The invention relates to novel chemical compounds of Formula I

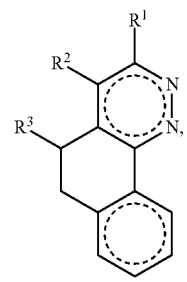

compounds and methods of using the same. In particular, the invention provides pyridazine compounds and/or related heterocyclic derivatives, compositions comprising the same, and methods of using pyridazine compounds and/or related heterocyclic derivatives and compositions comprising the same, for modulation of cellular pathways (e.g., signal transduction pathways), for treatment or prevention of inflammatory diseases (e.g., Alzheimer's disease), for research, drug screening, and therapeutic applications.

13 Claims, 7 Drawing Sheets

U.S. PATENT DOCUMENTS

| | | |
|---|---|---|
| 2008/0318899 A1 | 12/2008 | Watterson et al. |
| 2009/0029985 A1 | 1/2009 | Watterson et al. |

FOREIGN PATENT DOCUMENTS

| | | |
|---|---|---|
| EP | 0 094 038 | 11/1983 |
| EP | 0 211 437 | 2/1987 |
| EP | 0211457 A2 | 2/1987 |
| EP | 0382634 A1 | 8/1990 |
| EP | 0628550 A2 | 12/1994 |
| EP | 1061077 A1 | 12/2000 |
| FR | 2141697 A1 | 1/1973 |
| FR | 2 847 253 | 5/2004 |
| JP | 63295577 | * 12/1988 |
| JP | 04021670 | 1/1992 |
| JP | 04187674 | 7/1992 |
| WO | WO-98 39000 | 9/1998 |
| WO | WO9839000 | 9/1998 |
| WO | 9846574 A1 | 10/1998 |
| WO | 0142241 A1 | 6/2001 |
| WO | WO-02 22605 | 3/2002 |
| WO | 03018563 A1 | 3/2003 |
| WO | PCTEP2003047577 A3 | 6/2003 |
| WO | 2004046117 A1 | 6/2004 |
| WO | WO2004052348 | 6/2004 |
| WO | 2004062652 | 7/2004 |
| WO | 2004100958 | 11/2004 |
| WO | 2004101538 | 11/2004 |
| WO | 2005009976 A1 | 2/2005 |
| WO | 2005030731 | 4/2005 |
| WO | 2005061509 A1 | 7/2005 |
| WO | 2005063761 A1 | 7/2005 |
| WO | WO-2006-026135 | 3/2006 |
| WO | 2006050359 A2 | 5/2006 |
| WO | 2006050389 A2 | 5/2006 |
| WO | WO-2006 050389 | 5/2006 |
| WO | 2007127375 A1 | 4/2007 |
| WO | 2007127475 | 4/2007 |
| WO | 2007130383 | 4/2007 |
| WO | WO-2007 127375 | 4/2007 |
| WO | 2007127448 | 11/2007 |
| WO | 2007127474 | 11/2007 |
| WO | WO-2007-127488 | 11/2007 |
| WO | 2008109437 | 9/2008 |
| WO | WO-2008 109437 | 9/2008 |

OTHER PUBLICATIONS

Wikipedia, Isomers, last modified Aug. 16, 2010, http://en.wikipedia.org/wiki/Isomer, downloaded Aug. 24, 2010.*
Valentza, et al., Bioorg. & Med. Chem. Ltrs. (Oct. 3, 2003), 13(20), 3465-3470.*
Suzuki, et al., Heterocycles (2002), 57(4), 723-731.*
Costantino, et al., II Farmaco (2000), 55(8), 544-552.*
Sotelo, et al., Synthetic Communications (2000), 30(1), 1-7.*
Villa, et al., J. Het. Chem. (1999), 36(2), 485-492.*
Costantino, et al., J. Med. Chem. (1996), 39(22), 4396-4405.*
Cignarella, et al., J. Med. Chem. (1989), 32(10), 2277-82.*
Garcia Mera, et al., Anales de Quimica, Serie C: Quimica Organica y Bioquimica (1985), 81(3), 280-3.*
Bhattacherjee, et al., (1958) Zeitschrift fur Kristallographie, vol. 110, No. 1-6, pp. 472-474.*
Bluhm, J. Het. Chem. (1981), 18, 189-90.*
Partyka, et al., J. Med. Chem. (1971), 14(3), 262-4.*
Allen, et al., J. Am. Chem. Soc. (1951), 73, 5850-6.*
Borsche, et al., Justus Liebigs Annalen der Chemie (1943), 555, 70-7.*
Hu, et al., "Amyloid-B peptide activates cultured astrocytes: morphological alterations, cytokine induction and nitric oxide release," Brain Res. 785-195-206 (1998).
Hu, W., et al., "Pyridazines as a New Chemotype for Alzheimer's Disease Drug Discovery that Targets Disease Progression," 29th National Medicinal Chemistry Symposium, University of Wisconsin—Madison, Jun. 27-Jul. 1, 2004, Abstract and Poster.
Jones, R.G., "Pyrazines and Related Compounds. I. A New Synthesis of Nydroxypyrazines," J. Amer. Chem. Soc. 71: 78-81 (1949).
Karpus, W.J., et al., "Inhibition of experimental autoimmune encaphalomyelitis by a novel small molecular weight proinflammatory cytokine suppressing drug," J. Neuroimmunology 203(1): 73-78 (2008).
LaDu, et al., "Apolipoprotein E receptors Mediate the Effects of beta-Amyloid on Astrocyte Vultures," J. Biol. Chem. 275:33974-33980 (2000).
LaDu, et al., "Apolipoprotein E and apolipoprotein E Receptors Modulate a beta-induced gilal neuroinflammatory responses," Nuerochem Intl. 39:427-434 (2001).
Lam, et al., "Mechanism of glial activation by S100B: involvement of the transcription factor NFxB," Nuerobiol. Aging 22:765-772 (2001).
Melikian, et al., "Condensation of Muscimol or Thiomuscimol with Aminopyridazines Yields GABA-A antagonists," J. Med. Chem. 35, 4092-4097 (1992).
Merck: "The Merck Manual," Merck & Co., U.S.A., p. 1398, col. 2, "prognosis and treatment of Alzheimer's disease," (1999).
Mirzoeva, et al., "Screening in a cell-based assay for inhibitors of microglial nitric oxide production reveals calmodulin-regulated protein kinases as potential drug discovery targets," Brain Res. 844:126-134 (1999).
Mirzoeva, et al., "Discovery of a 3-amino-6-phenyl-pyridazine Derivative as a New Synthetic Antineuroinflammatory Compound," J. of Medicinal Chem. 45(3):563-566 (Watterson) (2002).
Munoz, L., et al., "A novel p38 alpha MAPK inhibitor suppresses btain proinflammatory cytokine up-regulation and attenuates synaptic dysfunction and behavioral deficits in an Alzheimer's disease mouse model," J. Neuroinflammation 4:21 (Sep. 2007).
"Compound holds promise for neurodegenerative diseases," Nelson Lancet Neurology 5(3) 210 (2006).
Hirohaski, et al., Pharmacological Studies with the Alpha2-Adrenoceptor Antagonist Midaglizole, Arzneim.-Forsch./Drug Res 41:9-18 (1991).
Pirvola, U., et al., "Rescue of Hearing, Auditory Hair Cells, and Neurons by CEP-1347/KT7515, an Inhibitor of c-Jun N-Terminal Kinase Activation," J. Neuroscience, 20:43-50 (2000).
Prusiner, S.B., et al. "Shattuck Lecture—Neurodegenerative Diseases and Prions," New Engl. J. Med. 344:1516-1526 (2001).
Ranaivo, H.R., et al., "Glia as a therapeutic target: selective suppression of human amyloid-beta-induced upregulation of brain proinflammatory cytokine production attenuates neurodegeneration," Jrnl. of Neurosc. 26(2) 662-670 (2006).
Ranaivo, H.R., et al., "Development of Orally Bioavailable Pyridazines that Suppress Neuroinflammation," 9th International Symposium on the Chemistry and Pharmacology of Pyridazines, Antwerp, Belgium, Jul. 2004, Abstract & Power.
Saturnino, C., et al., "Heterocyclic Amidines: I. A One-Step Synthesis of New alpha-substituted Imidazolyphenylacetic acids ," Heterocycles 41(7):1491-1501 (1995).
Sheng, J., et al., "In vivo and in vitro evidence supporting a role for the inflammatory cytokine interleukin-1 as a driving force in Alzheimer pathogenesis," Neurobiol. Aging 17:761-766 (1996).
Somera-Molena K.C., et al., "Glial activation links early-life seizures and long-term neurologic dysfunction: evidence using a small molecule inhibitor of pro-inflammatory cytokine upregulation," Epilepsia 48: 1785-1800 (2007).
Sotelo, E., et al., "Efficient aromatization of 4,5-dihydro-3-(2H)-pyridazinones substituted at 5 position by using anhydrous copper (II) chloride," Synthetic Communications 30:1-7 (2000).
Sotelo, E., et al., "Pyridazines. Part 26, Efficient and regioselective Pd-catalyzed arylation of 4-bromo-6-chloro-3-phenylpyridazine," Synless (2) 223-226 (2002).
Sridhar, et al., "Protein Kinases as Therapeutics Targets," Pharm. Res. 17:1345-1353 (2000).
Stahl, P.H., et al., "Handbook of Pharmaceutical Salts, Properties, Selection, and Use," Verlag Helvetica Chimica Acta & Wiley-Vch, Weinheim, International Union of Pure and Applied Chemistry, XP-002459552 (2002).
Toma, L., et al., "6-Chloropyridazin-3-yl Derivatives Active as Nicotinic Agents: Synthesis Binding and Modeling Studies," Jrnl. of Med. Chem. 45(8):4011-4017 (2002).

Van Eldik, et al., "Glia proinflammatory cytokine upregulation as a therapeutic target for neurodegenerative diseases: function-based and target-based discovery approaches," Int. Rev. Neurobiol. 82:277-296 (2007).

Van Eldik, et al., "S100 beta expression in Alzheimer's disease: relation to neuropathology in brain regions," Biochem. Biophys. Acta 1223: 398-403 (1994).

Van Eldik, et al., "Attenuation of Human Abeta-induced Neuroinflammation, Neuronal Death, and Hippocampus-Dependent Bahavioral Deficits by a New Class of Bioavailable Small Molecules," Presentation, CNS Diseases Congress: Advances in Therapeutics, Tools and Trials, Philadelphia, Jun. 28-29, 2004.

Van Niel, M.B., et al., "A New Phridazine Series of GABAA alpha-5 Ligands," J. Med. Chem., 48(19):6004-6011 (Merck) (2005).

Velentza, et al., "A protein kinase associated with apoptosis and tumor suppression: Structure, Activity and Discovery of Peptide Substrates," Jrnl. of Biol. Chem. 276(42):38956-38965 (2001).

Velentza, et al., "Structure, Activity, Regulation and Inhibitor Discovery for a Protein Kinase Associated with Apoptosis and Neuronal Death," Pharmacology & Therapeutics 93:217-224 (Feb. Mar. 2002).

Veleltza, et al., "An aminopyridazine-based inhibitor of a pro-apoptotic protein kinase attenuates hypoxia-ischermia induced acute brain injury," Bioorganic & Medicinal Chem. Ltrs. 13:3465-3470 (Watterson) (2003).

Velentza, et al., "Discovery of Substrates and Small Molecule Inhibitors for a Death Associated Protein Kinase," Cell. Biol. Mol. Lett. 6(2B):484-485 (2001).

Wainwright, M., et al., "Protein kinase involved in lung injury susceptibility: evidence from enzyme isoform genetic knockout and in vivo inhibitor treatment," Proc. Nat. Acad. Sci. USA (May 13, 2003) 100(10):6233-6238, Epub. May 2, 2003.

Watterson, et al., "Ligand modulation of glial activation: cell permeable, small molecule inhibitors of serine-threonine protein kinases can block induction of interleukin 1 beta and nitric oxide synthase II," Neurochem. Intl. 39:459-468 (2001).

Watterson, D.M., et al., "Discovery of a new class of synthetic protein kinase inhibitors that suppress selective aspects of flial activation and protect agains [J-amyloid induced injury. A foundation for future medicinal chemistry efforts focused on targeting Alzheimer's disease progression," J. Mol. Neuroscience 20:411-424 (2003).

Watterson, D.M., "Development of orally bioavailable small molecule modulators of disease progression in new Alzheimer's Disease related mouse models," Institute for the Study of Aging, Investigator's Meeting, New York, Oct. 7, 2004.

Watterson, D.M., "Discovery of new small molecule modulators of disease progression in an Alzheimer's Disease related mouse model," 12th Mainzer Forum in Medicinal Chemistry, Mainz, Germany, Oct. 2004, Presentation.

Vieth, et al., "Characteristic physical properties and structural fragments of marketed oral drugs," J. Med. Chem. 47:224-232. (2004).

Zhou, et al., "HERG-like K+ Channels in Microglia," J. Gen. Physiol. 111(6): 781-94. (1998).

Akiyama, et al., "Inflammation and Alzheimer's Disease," Neurobiol. Aging, 21:383-421 (2002).

Allen and Van Allen, "Some 3,4-Diphenylcinnolines and Related Compounds," J. Amer. Chem. Soc., 73:5854 (1951).

Apter, et al., "Buspirone: Future Directions," J. Clin. Psychopharmacol. 19:86-93 (1999).

Watterson, D.M., et al., "Discovery of New Chemical Classes of Synthetic Ligands that Suppress Neuroinflammatory Responses," Jrnl of Molecular Neuroscience, vol. 19, 89-93, 2002.

Cignarella, G., et al., "Synthesis and biological evaluation of substituted benzo[A]cinnolinones and 3H-benzo[6,7] cyclohepta[1,2-c]pyridazinones: higher homologues of the antihypertensive and antithrombotic 5H-indeno[1,2-c] pyridazinones," J. Med. Chem. 32:2277-2282 (1989).

Contreras, et al., "Aminopyridazines as Acetylcholinesterase Inhibitors," J. of Med. Chem., 42(4):730-741 (1999).

Contreras, et al., "Design, Synthesis, and Structure—Activity Relationships of a Series of 3-[2-(1-Benzylpiperidin-4-yl)ethylamino]pyridazine Derivatives as Acetylcholinesterase Inhibitors," Journ. of Med. Chem., 44(17):2707-2718 (2001).

Constantino, et al., "Synthesis, activity, and molecular modeling of a new series of tricyclic pyridazinones as selective aldose reductase inhibitors," Jrnl. of Med. Chem., 39:4396-4405 (1996).

Constantino, et al., "Synthesis and aldose reductase inhibitory activity of a new series of benzo[h]cinnolinone derivatives," II farmaco 55:544-552 (2000).

Coudert, et al., "A new synthetic route to 4,6-diarylpyridazinones and some of their derivatives," Jrnl. of Hetero. Chem., 25(3):799-802 (1988).

Craft, J.M., et al., "Human amyloid beta-induced neuroinflammation is an early event in neurodegeneration," Glia 53:484-490 (2006).

Craft, J.M., et al., "Aminopyridazines attenuate hippocampus dependent behavioral deficits induced by human (J-amyloid in a murine model of neuroinflammation," J. Mol. Neurosci., 24:115-122 (2004).

Craft, J.M., et al., "Aminopyridazines inhibit B-amyloid induced glial activation and neuronal damage in vivo," Neurobiol. Aging, 25:1283-1292 (2004).

Craft, J.M., et al., "Neuroinflammation: a potential therapeutic target," Expert. Opin. Ther. Targets, 9:887-900 (2005).

Csende, F., et al., "Copper(II) Chloride as an Efficient Reagent for the Dehydrogenation of Pyridazinone Derivatives," Synthesis, 1240-1242 (1995).

Database—Caplus—XP-002515676, AN:2003:775838 (2003).
Database—Beilstein—XP-002515678, RN:4403492 (Apr. 2008).
Database—Caplus—XP-002515675, AN:1989:423528 (1989).
Database—Capkus—XP-002515677, AN:1973:537067 (1973).
Database—Medline—XP-00253989, AN: NLM3950916 (1986).
Database—Medline—XP-00253989, AN: NLM2989499 (1985).

Du, Y., et al., "Association of an interleukin 1 [alpha] polymorphism with Alzheimer's disease," Neurology 55:480-484 (2000).

Eddy, S., et al., "Efficient Aromatization of 4,5-Dihydro-3(2H)-Pyridazinones Substituted at 5 Position by Using Anhydrous Copper(II) Chloride," Synthetic Communications 30(1):1-7 (2000).

Enyedy, I.J. et al., "Pharmacophore-based discovery of substituted pyridines as novel dopamine transporter inhibitors," Bioorganic & Medicinal Chemistry Letters 13(3) 513-517 (2003).

Farlow, M.R., "Utilizing combination therapy in the treatment of Alzheimer's disease," Expert review of Neurotherapeutics 4(5) 799-808 (2004).

Wermuth, C.-G., "Search for New Lead Compounds: The Example of the Chemical and Pharmacological Dissection of Aminopyridazines," Heterocyclic Chem., 35, 1091-1100 (1998).

Garattini, et al., "Notes on Buspirone's Mechanisms of Action," J. Clin. Psych, 43:19-24 (1982).

Griffin, et al., "Glial-Neuronal Interactions in Alzheimer's Disease: The Potential Role of a 'Cytokin cycle' in Disease Progression," Brain Pathol. 8:65-72 (1998).

Wermuth, C.-G., et al., "3-Aminopyridazine Derivatives with Atypical Antidepressant, Serotonergic, and Dipaminergic Activities," J. Med. Chem., 1989, 32, 528-537.

Wermuth, C.-G., et al., "Synthesis and Structure-Activity Relationships of a Series of Aminopyridazine Derivatives of Y-Aminobutyric Acid Acting as Selective GABA-A Antagonists," J. Med. Chem., 1987, 30, 239-249.

Heinisch, G., et al., "Pharmacologically active pyridazine derivatives, Part I," Prog. Med. Chem. 27:1-49 (1990).

Heinisch, G., et al., "Pharmacologically active pyridazine derivatives, Part II," Prog. Med. Chem. 29:141-183 (1992).

Wing, L.K., et al., "De Novo and Molecular Target-Independent Discovery of Orally Bioavailable Lead Compounds for Neurological Disorders," Current Alzheimer Research, 2006, 3, 205-214.

Hu, W., et al., "Validation of the Neuroinflammation Cycle as a Drug Discovery Target Using Integrative Chemical Biology and Lead Compound Development with an Alzheimer's Disease-Related Mouse Model," Current Alzheimer's Research, 2:197-205 (2005).

Hu, W., et al., "Development of a novel therapeutic suppressor of brain pro-inflammatory cytokine up-regulation that attenuates synaptic dysfunction and behavioral deficits," Bioorgan. Med. Chem. Lett. 17:414-418 (Watterson) (1996).

Hu, et al., "Apolipoprotein E Attenuates beta-amyloid-induced Astrocyte Activation," J. Nuerochem. 7:1626-1634 (1998).

Abdel, M et al., "Synthesis of 3-heterocyclic-5,6-diphenylpyridazines," Egyptian Journal of Pharmaceuticals Sciences, 1998, vol. 38, No. 1-3, pp. 87-93.

Adams et al., "Concise Synthesis of 1H-pyrazin-2-ones and 2-Aminopyrazines," Synlett., 2004, vol. 11, pp. 2031-2033.

Akama et al., "Amyloid Beta-peptide stimulates nitric oxide production in astrocytes through an NFκB-dependent mechanism," PNAS, 1998, vol. 95, pp. 5795-5800.

Badger et al., "Pharmacological Profile of SB 203580, a Selective Inhibitor of Cytokine Suppressive Binding Protein/ p38 Kinase, in Animal Models of Arthritis, Born Resorption, Endotoxin Shock and Immune Funtion," J. Pharmacol Exp. Ther., vol. 279, pp. 1453-1461, 1996.

Bhagwat et al., "Gene-regulation protein kinases as important anti-inflammatory targets," Drug Disc. Today, 1999, vol. 4, pp. 472-479.

Bhat et al., "Extracellular Signal-regulated Kinase and p38 Subgroups of Mitogen-Activated Protein Kinases Regulate Nitric Oxide Synthase and Tumor Necrosis Factor-alpha Gene Expression in Endotoxin-Stimulated Primary Gilial Cultures," J. Neurosci., vol. 18, pp. 1633-1641, 1998.

Blasi et al., "Immortalization of murine microglial cells by a v-raf/v-myc carrying retrovirus," J. Neuroimmunol. vol. 27, pp. 229-237 1990.

Brott et al., "Treatment of acute ischemic stroke," N Engl J Med., Sep. 7, 2000, vol. 343, No. 10, pp. 710-722.

Cardona et al., "Control of microglial neurotoxicity by the fractalkine receptor," Nature Neurosci., 2006, vol. 9, pp. 917-924.

Chayer, S. et al., "(3-Pyridazinamin-3-yl) Alpha-Aminoacids : A Facillitated Method of Preparation of Phenylalanine and Proline Representatives," Tetrahedron Letters, 1998, vol. 39, pp. 841-844.

Chen et al., "An Experimental Model of Closed Head Injury in Mice Pathophysiology, Histopathology, and Cognitive Deficits," J. Neurotrauma, 1996, vol. 13, pp. 557-568.

Chitaley, K. et al., "Antagonism of Rho-Kinase Stimulates Rat Penile Erection Via a Nitric Oxide-Independent Pathway," Nature Medicine, Jan. 2001, vol. 7, No. 1, pp. 119-122.

Craft, J. et al., "Enhanced susceptibility of S-100B transgenic mice to neuroinflammation and neuronal dysfunction induced by intracerebroventricular infusion of human Beta-amyloid," GLIA, 2005, vol. 51, pp. 209-216.

D'Ambrosio, R. et al., "Epilepsy after head injury," Curr. Opin. Neurol., 2004, vol. 17, pp. 7431-7735.

De Silva et al., "Blockade of p38 Mitogen-activated Protein Kinases Pathway Inhibits Inducibel Nitric-oxide Synthase Expression in Mouse Astrocytes," J. Biol Chem., vol. 272, pp. 28373-28380, 1997.

Dogan et al., "Effects of MDL 72527, a Specific Inhibitor of Polyamine Oxidase, on Brain Edema, Ischemic Injury Volume, and Tissue Polyamine Levels in Rats After Temporary Middle Cerebral Artery Occlusion," J. Neurochem., 1999, vol. 72, pp. 765.

Donato, R. et al., "Functional roles of S100 proteins, calcium-binding proteins of the EF-hand type," Biochem Biophys Acta, vol. 1450, pp. 191-231, 1999.

Dos Santos, "Invited review: mechanisms of Ventilatoe-induced lung injury: a perspective," Appl. Physiol, Oct. 2000, vol. 89, No. 4, pp. 1645-1655.

Dragunow M. et al., "Clusterin accumulates in dying neurons following status epilepticus," Mol. Brain. Res., 1005, vol. 32, pp. 279-290, 1995.

Dube, C. et al., "Prolonged Febrile Seizures in the immature rat model enhance hippocampal excitability long term," Ann Neurol., 2000, vol. 47, pp. 336-344.

Finlayson et al., "Acquired QT interval prolongation and HERG: implications for drug discovery and development," Eur J. Pharmacol., Oct. 2004, vol. 500, No. 1-3, pp. 129-142.

Frautschy, S. A. et al., "Rodent models of Alzheimer's disease: rat A Beta infusion approaches to amyloid deposits," Neurobiol. Aging., 1996, vol. 17, pp. 311-321.

French, J. et al., "Characteristics of medial temporal lobe epilepsy. I. Results of history and physical examination," Ann Neurol., 1993, vol. 34, pp. 774-780.

Garcia, "Regulation of Endothelial Cell Gap Formation and Barrier Dysfunction: Role of Myosin Light Chain Phosphorylation," J. Cell Physiol, 1995, vol. 163, pp. 510-522.

Gibbs, J. et al., "Mechanism-based target identification and drug discovery in cancer research," Science, 2000, vol. 287, pp. 1969-1973.

Giorgi, F et al., "Effects of status epilepticus early in life on susceptibility to ischemic injury in adulthood," Epilepsia, 2005, vol. 46, pp. 490-498.

Ghajar et al., "Traumatic Brain Injury," Lancet, Sep. 9, 2000, 356(9233), pp. 923-929.

Guo, L. et al., "Similar activation of glial cultures from different rat brain regions by neuroinflammatory stimuli and downregulation of the activation by a new class of small molecule ligands," Neurobiol. Aging. 2001, vol. 22, No. 6, pp. 975-981.

Guo, Z. et al., "Head Injury and the risk of AD in the MIRAGE study," Neurology, 2000, vol. 54, pp. 1316-1323.

Hagberg, H. et al., "Effect of inflammation on central nervous system development and vulnerability," Curr. Opin. Neurol., 2005, vol. 18, pp. 117-123.

Han, B. et al., "Clusterin contributes to caspase-3-independent brain injury following neonatal hypoxia-ischemia," Nature Med., 2001, vol. 7, pp. 338-343.

Hansen, K. B. et al., "First Generation Process for the Prepartion of the DDP-IV Inhibitor Sitagliptin," Organic Process Research & Development, 2005, vol. 9, pp. 634-639.

Hargreaves et al., "A new and sensitive method for measuring thermal nociception in cutaneous hyperalgesia," Pain, 1988, vol. 32, pp. 72-78.

Haut, S. et al., "Susceptibility of immature and adult brains to seizure effects," Lancet Neurol., 2004, vol. 3, pp. 608-617.

Holmes, G. et al., "Effects of seizures on brain development: lessons from the laboratory," Pediatr Neurol., 2005, vol. 33, pp. 1-11.

Holmes, G. et al., "Seizures in the developing brain: perhaps not so benign after all," Neuron, 1998, vol. 21, pp. 1231-1234.

Hu et al., "S 100-Beta Stimulates Inducible Nitric Oxide Synthase Activity and Mrna Levels in Rat Cortical Astrocytes," J. Biol. Chem., 1996, vol. 271, pp. 2543-2547.

Huang, Y et al., "Glutamate transporters bring competition to the synapse," Curr. Opin. Neurobiol., 2004, vol. 14, pp. 346-352.

Igarashi et al., "Exogenous Tumor Necrosis Factor-Alpha Mimics Nucleus Pulposus-Induced Neuropathology," Spine, 2000, vol. 25, pp. 2975-2980.

Jensen, F. et al., "NBQX blocks acute and late epileptogenic effects of perinatal hypoxia," Epilepsia, 1995, vol. 36, pp. 966-972.

Koh, S. et al., "Early-life seizures increase susceptibility to seizure-induced brain injury in adulthood," Neurology, 1999, vol. 53, pp. 915-921.

Kulkarni, V., "Structure-activity relationship in pyridazine and phathalazine series of antihypertensive agents by molecular orbital calculations," Indian Juran of Biochemistry & Biophysics, 1975, vol. 12, No. 4, pp. 367-369.

Kumar et al., "Drugs Targeted Against Protein Kinase," Expert Opinion, 2001, vol. 6, No. 2, pp. 303-315.

Lambert et al., "Diffusible, nonfribrillar ligands derived from Alpha-beta1-42 are potent central nervous system neurotoxins," PNAS, 1998, vol. 95, pp. 6448-6453.

Laskowitz et al., "Downregulation of Microglial Activation by Apolopoprotein E and ApoE-Mimetic Peptides," Exp. Neurol. 2001, vol. 167, pp. 74-85.

Letty, S. et al., "Differential impairments of spatial memory and social behavior in two models of limbic epilepsy," Epilepsia, 1995, vol. 36, pp. 973-982.

Levition, A. et al., "Brain damage markers in children. Neurobiological and clinical aspects," Acta Paediatrica, 2002, vol. 91, pp. 9-13.

Longa et al., "Reversible Middle Cerebral Artery Occlusion Without Craniectomy in Rats," Stroke, 1989, vol. 30, pp. 84-91.

Loscher, W. et al., "New Horizons in the development of antiepileptic drugs," Epilepsy Res., 2002, vol. 50, pp. 3-16.

Maragakis, N. et al., "Glutamate transporters: animal models t neurologic disease," Neurobiol Dis. 2004, vol. 15, pp. 461-473.

Maroney et al., "CEP-1347 (KT7515), a semisynthetic inhibitor of the mixed lineage kinase family," J. Biol Chem., 2001, vol. 276, No. 27, pp. 25302-25308.

Maroney et al., "CEP-1347 (KT7515), an inhibitor of JNK Activation, Rescues Sympathetic Neurons and Neuronally Differentiated PC 12 Cells from Death Evoked by Three Distinct Insults," J. Neurochem., 2001, vol. 73, No. 1901-1912.
Minghetti, L. et al., "Role of Inflammation in neurodegenerative diseases," Curr. Opin. Neurol., 2005, vol. 18, pp. 315-321.
Morris, R. G. M., "Spatial Localization Does Not Require the Presence of Local Cues," Learning and Motivation vol. 12, 1981, pp. 239-260.
Morris, R., "Developments of a Water-Maze Procedure for Studying Spatial Learning in the Rat," Journal of Neuroscience Methods, vol. 11, 1984, pp. 47-60.
Mrak, R. et al., "Glia and cytoknes in progression of neurodogeneration," Neurobiol Aging, 2005, Volo. 26, pp. 349-354.
Namura et al., "Intravenous administration of MEK inhibitor U00126 affords brain protection against forebrain Ischemia and focal cerebral ischemia," Proc Natl Acad Sci USA, Sep. 25, 2001, vol. 98, No. 20, pp. 11569-11574, Epub Aug. 14, 2001.
Ohno et al., "Differential effects of Alpha-CaMKII mutation on hippocampal learning and changes in intrinsic neuronal excitability," Eur. J. Neurosci., 2006, vol. 23, No. 8, pp. 2235-2240.
Ohno et al., "Trace eyeblink conditioning requires the hippocampus but not autophosphorylation of Alpha-CaMKII in mice," Learning & Memory, 2005, vol. 12, No. 3, pp. 211-215.
Parker, J. et al., "Inhibitors of myosin light chain kinase and phosphodiesterase reduce ventilator-induced lung injury," J. Appl. Physiol, Dec. 2000, vol. 89, No. 6, pp. 2241-2248.
Perry, V et al., "Systemic infections and inflammation affect chronic neurodegeneration," Nat Rev Immunol., 2007, doi: 10.1038/nri 2015.
Petrova et al., "Cyclopentenone prostaglandins suppress activation of microglia: Down-regulation of inducible nitric-oxide synthase by 15-deoxy-Δ 12, 14-prostaglandin J2," PNAS, 1999, vol. 96, pp. 4668-4673.
Rao, V. et al., "Antisense Knockdown of the glial glutamate transporter GLT-1 exacerbates hippocampal damage following traumatic injury to rat brain," Eur. J. Neurosci., 2001, vol. 13, pp. 119-128.
Ravizza et al., "Inflammatory response and glia activation in developing rat hippocampus after status epilepticus," Epilepsia, 2005, vol. 46, pp. S113-S117.
Recanatini et al., "QT prolongation through hERG K (+) channel blockade: current knowledge and strategies for the early prediction during drug development," Med Res Rev, Mar. 2005, vol. 25, No. 2, pp. 133-166.
Rizzi et al., "Glia activation and cytokine increase in rat hippocampus by kainic acid-induced status epilepticus during postnatal development," Neurobiol. Dis., 2003, vol. 14, pp. 494-503.
Roden, "Drug-induced prolongation of the QT interval," N. Engl. J. Med., Mar. 4, 2004, vol. 350, No. 10, pp. 1013-1022.
Rothermundt, M. et al., "S100B in brain damage and neurodegeneration," Mircoscopy Research & Technique, 2003, vol. 60, pp. 614-632.
Sanchez et al., "Decreased glutamate receptor 2 expression and enchanced epileptogenesis in immature rat hippocampus after perinatal hypoxia-induced seizures," J. Neurosci., 2001, vol. 21, pp. 8154-8563.
Sayin, U., et al., "Seizures in the developing brain cause adverse long-term effects o spatial learning and anxiety," Epilepsia, 2004, vol. 45, pp. 1539-1548.
Schmid, R. et al., "Effects of neonatal seizures on subsequent seizure-induced brain injury," Neurology, 1999, vol. 53, pp. 1754-1761.
Schmued, L. et al., "Fluoro-Jade B: a high affinity fluorescent marker for the localization of neuronal degeneration," Brain Res., 2000, vol. 874, pp. 123-130.
Schumacher et al., "Death Associated Protein Kinase as a Potential Therapeutic Target," Expert Opin. Ther. Targets, Aug. 2002, vol. 6, No. 4, pp. 497-506.
Selkoe, D. J. et al., "Alzheimer's Disease: Genes, Proteins, and Therapy," Physiol. Rev., 2001, vol. 81, pp. 741-766.
Stevens et al., "NHLBI workshop report: endothelial cell phenotypes in heart, lung, and blood diseases," Am J Physiol Cell Physiol, Nov. 2001, vol. 281, No. 5, pp. 1422-1433.
Strohmeyer, R. et al., "Association of factor H of the alternative pathway of complement with agrin and complement receptor 3 in Alzheimer's disease brain," J. Neuroimmunol., 2002, vol. 131, pp. 135-146.
Strohmeyer, R. et al., "Molecular and cellular mediators of Alzheimer's disease inflammation," J. Alz. Dis., 2001, vol. 3, pp. 131-157.
Tereshko et al., "Crystal structures of the catalytic domain of human protein kinase associated with apoptosis and tumor suppression," Nat Struct Biol., Oct. 2001, vol. 8, No. 10, pp. 899-907.
Tinsley et al., "Myosin light chain kinase transference induces myosin light chain activation and endothelial hyperpermeability," Am J Physiol Cell Physiol, Oct. 2000, vol. 279, No. 4, pp. 1285-1289.
Troy et al., "Beta-amyloid-induced neuronal apoptosis required c-Jun N-terminal kinase activation," J. Neurochem., 2001, vol. 77, pp. 157-164.
Van Eldik et al., "Synthesis and Expression of a Gene Coding for the Calrium-modulated Protein 5100B and designed for cassette-based, Site-directed Mutagenesis," J. Biol. Chem., 1988, vol. 263, pp. 7830-7837.
Van Eldik et al., "The Janus face of glial-derived S100B: beneficial and detrimental functions in the brain," Restorative Neurol Neurosci., 2003, vol. 21, pp. 97-108.
Veber et al., "Molecular 30 properties that influence the oral bioavailability of drug candidates," J. Med. Chem, 2002, vol. 45, pp. 2615-2623.
Verbitsky, M. et al., "Altered hippocampal transcript profile accompanies an age-related spatial memory deficit in mice," 2004, Learning and Memory, vol. 11, pp. 253-260.
Vezzani et al., "Functional role of inflammatory cytokines and anti-inflammatory molecules in seizures and epileptogenesis," Epilepsia, 2002, vol. 43, pp. S30-S35.
Vezzani, A. Epilepsy Currents, vol. 4, No. 2, Feb. 26, 2004, pp. 73-75.
Vezzani, A. et al., "Brain Inflammation in epilepsy: Experimental and clinical evidence," Epilepsia, 2005, vol. 46, pp. 1724-1743.
Wainwright, M et al., "Carnitine treatment inhibits increases in cerebral carnitine esters and glutamate detected by mass spectrometry following hypoxiaischemia in newborn rats," Stroke 37,2005, pp. 524-530.
Wainwright, M. et al., "Increased susceptibility of 5100B transgenic mice to perinatal hypoxia-ischemia," Annals of Neurol., 2004, vol. 56, pp. 61-67.
Weiss, C. et al., "Spatial learning and memory in aging C57BL/b mice," Neurosci. Res. Comm., 1998, vol. 23, No. 2, pp. 77-92.
Weiss, S. et al., "Anatomic studies of DNA fragmentation in rat brain after systemic kainic acid administration," Neuroscience, vol. 74, No. 2, pp. 541-551.
Wermuth, C. G. et al., Selected Procedures for the Preparation of Pharmaceutically accgplable salts, in Stahl. P.H., Wermuth, C.G. (Ed.) Handbook of Pharmaceutical Salts, Wiley-VCH, pp. 249-264, 2002.
Yamamoto et al., "Development changes in distribution of death-associated protein kinase mRNAs," J Neurosci Res., 1999, vol. 58, pp. 674-683.
Yoshinari et al., "Effects of a dual inhibitor of tumor necrosis factor-alpha and interleukin-1 on lipopolysaccharide-induced lung injury in rats: involvement of the p38 mitogen-activated protein kinase pathway," Crit. Care Med., Mar. 2001, vol. 29, No. 3, pp. 628-634.
Zhang, G. et al., "Long-term alterations in glutamate receptor and transporter expression following early-life seizures are associated with increased seizure susceptibility," J. Neurochem., 2004, vol. 88, pp. 91-101.
Thomson Innovation, "3-amino-6-aryl-1,2,4-triazolo(4,3-b) pyridazines, their preparation and use," Retrieved from Patent Record View on Sep. 1, 2010; English Abstracts of EP0094038.
Communication regarding the Extended European Search Report for EP 05823123 dated Mar. 2, 2009.
Supplementary European Search Report for EP05823123 dated Feb. 18, 2009.
Communication pursuant to Article 94(3) EPC for EP05823123 dated Dec. 17, 2009.
Communication pursuant to Article 94(3) EPC for EP 07776351 dated Oct. 9, 2010.
Communication pursuant to Article 94(3) EPC for EP07756162 dated Feb. 11, 2009.
Reply to Communication pursuant to Article 94(3) EPC for EP07756162 of Feb. 11, 2009 dated Nov. 19, 2009.

Communication pursuant to Article 94(3) EPC for EP07756162 dated Feb. 5, 2010.
Office Action for CN 200580037702 dated Sep. 4, 2009 with translation.
Office Action for MX/a/2007/005247 dated Aug. 25, 2009 with translation.
Reply to Office Action for MX/a/2007/005247 of Aug. 25, 2009 dated Mar. 1, 2010.
Office Action regarding POA documents for MX/a/2007/005247 dated Nov. 2, 2005.
Communication regarding the European Search Report for EP 02796459 dated Oct. 29, 2004.
Supplementary European Search Report for EP 02796459 dated Oct. 7, 2004.
Communication pursuant to Article 94(3) EPC for EP 02796459 dated Sep. 30, 2010.
Reply to Communication pursuant to Article 94(3) EPC for EP 02796459 of Sep. 30, 2010 dated Apr. 8, 2009.
Hu, et al., "S 100-Beta Stimulates Inducible Nitric Oxide Synthase Activity and mRNA Levels in Rat Cortical Astrocytes," J. Biol. Chem., vol. 271, pp. 2543-2547 (1996).
Chayer, S. et al., "(3-Pyridazinamin-3-yl) Alpha-Aminoacids : A Facillitated Method of Preparation of Phenylalanine and Proline Representatives, " Tetrahedron Letters, vol. 39, pp. 841-844 (1998).
Badger, et al., "Pharmacological Profile of SB 203580, a Selective Inhibitor of Cytokine Suppressive Binding Protein/ p38 Kinase, in Animal Models of Arthritis, Bone Resorption, Endotoxin Shock and Immune Funtion," J. Pharmacol Exp. Ther., vol. 279, pp. 1453-1461 (1996).
Bhat, et al., "Extracellular Signal-regulated Kinase and p38 Subgroups of Mitogen-Activated Protein Kinases Regulate Nitric Oxide Synthase and Tumor Necrosis Factor-alpha Gene Expression in Endotoxin-Stimulated Primary Gilial Cultures," J. Neurosci., vol. 18, pp. 1633-1641 (1998).
Blasi, et al., "Immortalization of murine microglial cells by a v-raf/ v-myc carrying retrovirus," J. Neuroimmunol. vol. 27, pp. 229-237 (1990).
De Silva, et al., "Blockade of p38 Mitogen-activated Protein Kinases Pathway Inhibits Inducibel Nitric-oxide Synthase Expression in Mouse Astrocytes," J. Biol Chem., vol. 272, pp. 28373-28380 (1997).
Donato, R. et al., "Functional roles of S100 proteins, calcium-binding proteins of the EF-hand type," Biochem Biophys Acta, vol. 1450, pp. 191-231 (1999).
Dragunow, M. et al., "Clusterin accumulates in dying neurons following status epilepticus," Mol. Brain. Res., 1005, vol. 32 (2), pp. 279-290 (1995).
Stahl. PH, et al., "Handook of pharmaceutical salts. Properties, selection and use." Verlag Helvetica Chimica Acta & Wiley-VCH, Weinheim. (2002).
Weiss, S. et al., "Anatomic studies of DNA fragmentation in rat brain after systemic kainate acid administration," Neuroscience, vol. 74, No. 2, pp. 541-551 (1996).

* cited by examiner

MW01-2-151WH, X = N, Y = N

MW01-3-173WH, X = CH, Y = CH

MW01-3-202WH, X = N, Y = CH

PYRIDAZINE COMPOUNDS AND METHODS

RELATED APPLICATIONS

This application is a continuation application of U.S. application Ser. No. 11/666,872 filed on May 1, 2007 now abandoned which claims priority benefit from prior U.S. Provisional Application Ser. No. 60/624,346 filed Nov. 2, 2004 and U.S. Provisional Application Ser. No. 60/723,376 filed Oct. 4, 2005, all of which are incorporated in their entirety by reference.

This invention was made with government support under Grant Numbers P01 AG021184 and R01 NS047586 awarded by the National Institute of Health (NIH). The government has certain rights in the invention.

FIELD OF INVENTION

The invention relates to novel chemical compounds and methods of making and using the same. In particular, the invention provides pyridazine compounds and/or related heterocyclic derivatives, in particular cinnoline compounds, compositions comprising the same, and methods of using pyridazine compounds and/or related heterocyclic derivatives, in particular cinnoline compounds, and compositions comprising the same, for modulation of cellular pathways (e.g., signal transduction pathways), for treatment or prevention of inflammatory diseases (e.g., Alzheimer's disease), for research, drug screening, and therapeutic applications.

BACKGROUND OF INVENTION

The majority of inflammatory conditions and diseases result from a disruption in the homeostatic balance between beneficial and detrimental responses of the organism. For example, there may be a decrease in the production of trophic molecules that mediate cell survival and other beneficial cellular processes, or there may be an overproduction of pro-inflammatory or other detrimental molecules that mediate toxic cellular responses. Disregulation of signal transduction pathways involving protein kinases are often involved in the generation or progression of these diseases. For example, neuroinflammation is a process that results primarily from an abnormally high or chronic activation of glia (microglia and astrocytes). This overactive state of glia results in increased levels of inflammatory and oxidative stress molecules, which can lead to neuron damage or death. Neuronal damage/death can also induce glial activation, facilitating the propagation of a localized, detrimental cycle of neuroinflammation [7].

The inflammation (e.g., neuroinflammation) cycle has been proposed as a potential therapeutic target in the development of new approaches to treat inflammatory disease (e.g., Alzheimer's disease). However, the efficacy and lexicological profile of compounds that focus only on classical non-steroidal anti-inflammatory drug targets have been disappointing to date, for example, most anti-inflammatory therapeutics are palliative, providing minimal, short-lived, symptomatic relief with limited effects on inflammatory disease (e.g., neuroinflammatory diseases such as Alzheimer's disease) progression. Because the major societal impact from inflammatory diseases (e.g., neuroinflammatory diseases such as Alzheimer's disease) is expected to increase greatly in coming decades, there is an urgent need for anti-inflammatory therapeutics that impact disease progression when administered soon after diagnosis (e.g., diagnosis of cognitive decline), or in a chemo-preventive paradigm as combinations of risk factors with prognostic value are identified. In either therapeutic paradigm, new drugs must have a good therapeutic index, especially in regard to potential toxicology in the elderly.

Despite an overwhelming need, and the presence of well-defined molecular targets, the current anti-inflammatory drug development pipeline is lacking chemically diverse compounds that work within the relevant therapeutic window and treatment paradigm needed for altering disease progression, an area of comparative neglect that fits this therapeutic window is neuroinflammation [1]. Thus, the development of new classes of anti-inflammatory compounds that can modulate inflammatory disease-relevant pathways is urgently needed.

SUMMARY OF INVENTION

The present invention relates to novel chemical compounds and methods of making and using the same. In particular, the present invention provides cinnoline compounds and/or related heterocyclic derivatives, compositions comprising the same, and methods of using pyridazine compounds and/or related heterocyclic derivatives, and compositions comprising the same, for modulation of cellular pathways (e.g., signal transduction pathways), for treatment or prevention of inflammatory diseases (e.g., Alzheimer's disease), for research, drug screening, and therapeutic applications.

Broadly stated, the invention provides a method for treating a disease disclosed herein, in particular an inflammatory disease, in a subject comprising administering to the subject a compound of the Formula I, comprising Formulas Ia, Ib, Ic and Id:

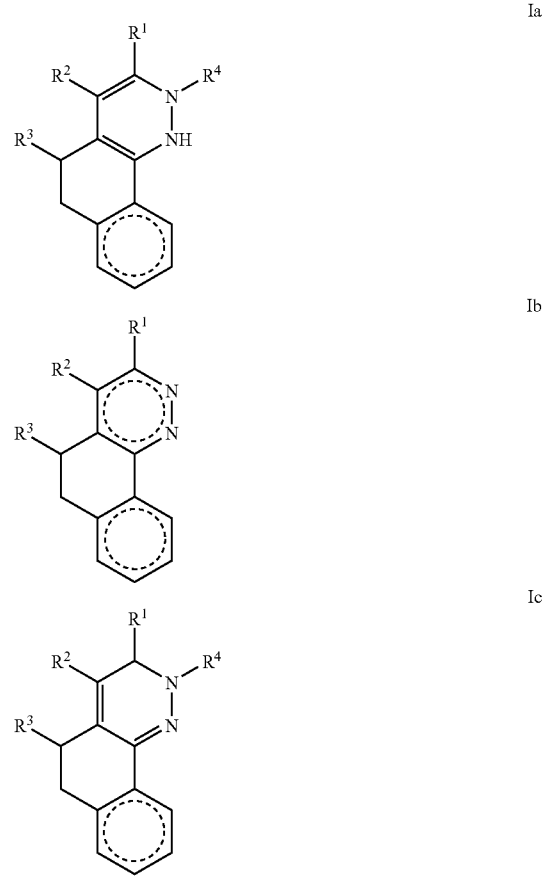

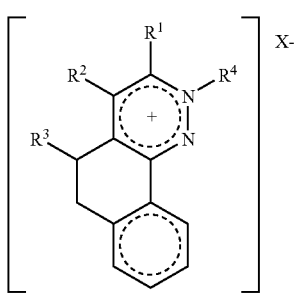

wherein $R^1$, $R^2$, $R^3$, and $R^4$ are independently substituted or unsubstituted hydrogen, hydroxyl, alkyl, alkenyl, alkynyl, alkylene, alkenylene, alkoxy, alkenyloxy, cycloalkyl, cycloalkenyl, aryl, aryloxy, arylalkoxy, aroyl, heteroaryl, heterocyclic, acyl, acyloxy, sulfonyl, sulfinyl, sulfenyl, amino, imino, azido, thiol, thioalkyl, thioalkoxy, thioaryl, nitro, ureido, cyano, halo, silyl, silyloxy, silylthio, carboxyl, carbonyl, carbamoyl, or carboxamide, or a tautomer, an isomer, a conjugate base, or a pharmaceutically acceptable salt thereof.

In an aspect, a method is provided for treating a disease disclosed herein in a subject comprising administering a compound of the Formula I as defined herein with the proviso that compounds depicted in Table 3 are excluded.

The invention relates to a method for treating diseases disclosed herein in a subject comprising administering to the subject a therapeutically effective amount of one or more compound of the Formula I, or an isomer or a pharmaceutically acceptable salt thereof, or a composition comprising a compound of the Formula I and a pharmaceutically acceptable carrier, excipient, or vehicle. In an aspect the invention provides beneficial effects following treatment.

In another aspect of the invention, a method is provided for treating in a subject a disease involving or characterized by inflammation, in particular neuroinflammation, comprising administering to the subject a therapeutically effective amount of a compound of the Formula I, or an isomer or a pharmaceutically acceptable salt thereof. In a further aspect, a method is provided for treating in a subject a condition involving inflammation, in particular neuroflammation, comprising administering to the subject a therapeutically effective amount of a composition comprising a compound of the Formula I or an isomer or a pharmaceutically acceptable salt thereof, and a pharmaceutically acceptable carrier, excipient, or vehicle.

In a further aspect, the invention provides a method involving administering to a subject a therapeutic compound of the Formula I, or an isomer, or a pharmaceutically acceptable salt thereof, or a composition comprising a compound of the Formula I, or an isomer, or a pharmaceutically acceptable salt thereof, and a pharmaceutically acceptable carrier, excipient, or vehicle which inhibit or reduce neuroflammation, activation of glia, proimflammatory cytokines, oxidative stress-related enzymes, acute phase proteins and/or components of the complement cascade.

In another aspect, the invention provides a method for treating in a subject a disease associated with neuroinflammation that can be decreased or inhibited with a compound disclosed herein comprising administering to the subject a therapeutically effective amount of a compound of the Formula I, or an isomer or a pharmaceutically acceptable salt thereof, or a composition comprising a compound of the Formula I, and a pharmaceutically acceptable carrier, excipient, or vehicle.

Methods of the invention may be used to prevent or inhibit activation of protein kinases, in particular death associated protein kinase (DAPK); reduce or inhibit kinase activity, glial activation, neuronal cell damage, and/or neuronal cell death; inhibit cell signaling molecule production (e.g., IL-1β and TNFα), ameliorate progression of a disease or obtain a less severe stage of a disease in a subject suffering from such disease; delay the progression of a disease in a subject; increase survival of a subject suffering from a disease; and/or treat or prevent a neurodegenerative disease in a subject.

In particular aspects of the methods of the invention, a compound of the formula I is a compound depicted in the Figures and Tables, in particular Table 4.

A method of the invention can be used therapeutically or prophylactically in a subject susceptible to or having a genetic predisposition to a disease disclosed herein. Therefore, the invention provides a method of preventing a disease disclosed herein in a subject with a genetic predisposition to such disease by administering an effective amount of one or more of a compound of the Formula I, or an isomer or a pharmaceutically acceptable salt thereof, or a composition comprising a compound of the Formula I and a pharmaceutically acceptable carrier, excipient, or vehicle.

The invention has particular applications in treating or preventing a neurodegenerative disease, in particular Alzheimer's disease. Thus, the invention relates to a method of treatment comprising administering a therapeutically effective amount of one or more compound of the formula I, an isomer or a pharmaceutically acceptable salt thereof, or a composition comprising a compound of the formula I and a pharmaceutically acceptable carrier, excipient, or vehicle, which upon administration to a subject with symptoms of a neurodegenerative disease, in particular Alzheimer's disease, produces one or more therapeutic effect, in particular a beneficial effect, more particularly a sustained beneficial effect.

The invention relates to a method of improving the lifespan of a subject suffering from Alzheimer's disease comprising administering a therapeutically effective amount of one or more of a compound of the formula I, an isomer or a pharmaceutically acceptable salt thereof, or a composition comprising one or more of a compound of the formula I and a pharmaceutically acceptable carrier, excipient, or vehicle.

The invention relates to a compound of the formula I as defined herein with the proviso that compounds depicted in Table 3 are excluded.

A compound of the formula I may be in the form of a prodrug that is converted in vivo to an active compound. In addition, a compound of the formula I may optionally comprise a carrier interacting with one or more of $R^1$, $R^2$, $R^3$, and $R^4$. A carrier may be a polymer, carbohydrate, or peptide, or combinations thereof, and it may be optionally substituted, for example, with one or more alkyl, halo, hydroxyl, halo, or amino.

In accordance with aspects of the invention pyridazine compounds and/or related heterocyclic derivatives thereof, in particular cinnoline compounds (See, for e.g., the Figures and Tables herein, in particular the compounds depicted in Table 4 or derivatives thereof) are provided for use in research, drug screening, for modulation of cellular pathways (e.g., signal transduction pathways), and for treatment or prevention of inflammatory diseases (e.g., Alzheimer's disease). In some embodiments, the present invention provides new classes of chemical compounds capable of modulating pro-inflammatory and oxidative stress related cellular signaling pathways (e.g., in activated glial cells). In some embodiments, one or more compounds of the Figures and Tables herein, in particular Table 4, are used to modulate kinase activity alone or in combination with other compounds or therapies. In some embodiments, the compounds encompassed by the present invention include triazine compounds comprising the structure 3-chloro-5,6-dihydrobenzo[h]cinnoline (FIG. 1, compound 7). In some embodiments, compounds, and methods of using the compounds, provided by the invention are those depicted in the Figures and Tables herein, in particular Table 4. In some embodiments, the present invention also provides methods of making the compounds of the Figures and Tables herein, comprising the steps provided (See, e.g., FIG. 1 and Materials and Methods). In preferred embodiments, the common precursor, 3-chloro-5,6-dihydrobenzo[h]cinnoline (FIG. 1 compound 7) is used in the synthesis of MW01-2-151WH, MW01-3-202WH, and/or MW01-3-173WH.

In some embodiments, the invention provides MW01-2-151WH, MW01-3-202WH and MW01-3-173WH, and/or related heterocyclic derivatives of these compounds and methods of making and using the same for modulating cellular pathways (e.g., signal transduction pathways) for use in research, drug screening, and therapeutic applications.

In an aspect, the invention provides compositions for prevention and/or treatment of a disease disclosed herein. Thus, the invention provides a pharmaceutical composition comprising a compound of the Formula I, or an isomer or pharmaceutically acceptable salt thereof, in particular a therapeutically effective amount of a compound of the Formula I, or an isomer or pharmaceutically acceptable salt thereof, for treating a disease. More particularly, the invention provides a pharmaceutical composition in a form adapted for administration to a subject to provide therapeutic effects, in particular beneficial effects to treat a disease disclosed herein.

In another aspect, the composition is in a form that results in a decrease or reversal in a subject of one or more of the following, or in a form such that administration to a subject suffering from a disease results in a decrease or reversal of one or more of the following: inflammation (e.g. neuroinflammation), activation of signaling pathways involved in inflammation (e.g., neuroinflammation), cell signaling molecule production, activation of glia or glial activation pathways and responses, proinflammatory cytokines or chemokines [e.g., interleukin (IL) or tumor necrosis factor (TNF)], oxidative stress-related responses such as nitric oxide synthase production and nitric oxide accumulation, acute phase proteins, components of the complement cascade, protein kinase activity (e.g., death associated protein kinase activity), cell damage (e.g., neuronal cell damage), and/or cell death (e.g., neuronal cell death).

In an aspect, the invention features a composition comprising a compound of the invention in a therapeutically effective amount for decreasing or reversing of one or more of the following: inflammation (e.g. neuroinflammation), activation of signaling pathways involved in inflammation (e.g., neuroinflammation), cell signaling molecule production, activation of glia or glial activation pathways and responses, proinflammatory cytokines or chemokines (e.g., interleukin (IL) or tumor necrosis factor (TNF), oxidative stress-related responses such as nitric oxide synthase production and nitric oxide accumulation, acute phase proteins, components of the complement cascade, protein kinase activity (e.g., death associated protein kinase activity), cell damage (e.g., neuronal cell damage), and/or cell death (e.g., neuronal cell death) in a subject. The composition can be in a pharmaceutically acceptable carrier, excipient, or vehicle.

Additionally the invention contemplates a method of preparing a stable pharmaceutical composition comprising one or more compound of the Formula I or an isomer or pharmaceutically acceptable salt thereof. After the composition is prepared, it can be placed in an appropriate container and labeled for treatment of an indicated disease. For administration of a composition of the invention, such labeling would include amount, frequency, and method of administration.

In some aspects the invention provides methods to make commercially available pills, tablets, caplets, soft and hard gelatin capsules, lozenges, sachets, cachets, vegicaps, liquid drops, elixirs, suspensions, emulsions, solutions, syrups, aerosols (as a solid or in a liquid medium) suppositories, sterile injectable solutions, and/or sterile packaged powders, which contain a compound of the Formula I of the invention.

In an aspect, compounds and compositions of the invention may be administered therapeutically or prophylactically to treat a disease disclosed herein. While not wishing to be bound by any particular theory, the compounds and compositions may act to ameliorate the course of a disease using without limitation one or more of the following mechanisms: preventing, reducing and/or inhibiting inflammation (e.g. neuroinflammation), activation of signaling pathways involved in inflammation (e.g., neuroinflammation), cell signaling molecule production, activation of glia or glial activation pathways and responses, proinflammatory cytokines or chemokines [e.g., interleukin (IL) or tumor necrosis factor (TNF)], oxidative stress-related responses such as nitric oxide synthase production and nitric oxide accumulation, acute phase proteins, components of the complement cascade, protein kinase activity (e.g., death associated protein kinase activity), cell damage (e.g., neuronal cell damage), and/or cell death (e.g., neuronal cell death).

The invention relates to the use of a composition comprising at least one compound of the Formula I or an isomer or pharmaceutically acceptable salt thereof, for the preparation of a medicament for treating a disease disclosed herein. The invention additionally relates to use of a pharmaceutical composition of the invention in the preparation of a medicament for the prevention and/or treatment of a disease disclosed herein. The medicament may be in a form suitable for consumption by a subject, for example, a pill, tablet, caplet, soft and hard gelatin capsule, lozenge, sachet, cachet, vegicap, liquid drop, elixir, suspension, emulsion, solution, syrup, aerosol (as a solid or in a liquid medium) suppository, sterile injectable solution, and/or sterile packaged powder.

The invention further relates to a kit comprising one or more compound of the Formula I, or an isomer or pharmaceutically acceptable salt thereof, or a composition comprising one or more compound of the Formula I, or an isomer or pharmaceutically acceptable salt thereof. In an aspect, the invention provides a kit for preventing and/or treating a disease disclosed herein comprising one or more compound of the Formula I or an isomer or pharmaceutically acceptable salt thereof, a container, and instructions for use. The composition of a kit of the invention can further comprise a pharmaceutically acceptable carrier, excipient, or vehicle.

The compounds of the Formula I (in particular the compounds depicted in Table 4) provide a structural scaffold on which to base compositions for decreasing or reversing one or more of the following: inflammation (e.g. neuroinflammation), activation of signaling pathways involved in inflammation (e.g., neuroinflammation), cell signaling molecule production, activation of glia or glial activation pathways and responses, proinflammatory cytokines or chemokines (e.g., interleukin (IL) or tumor necrosis factor (TNF), oxidative stress-related responses such as nitric oxide synthase production and nitric oxide accumulation, acute phase proteins, components of the complement cascade, protein kinase activ- ity (e.g., death associated protein kinase activity), cell damage (e.g., neuronal cell damage), and/or cell death (e.g., neuronal cell death), wherein the compounds comprise a structure of Formula I.

Thus, the invention also contemplates libraries or collections of compounds all of which are represented by a compound of the Formula I, in particular a compound depicted in Table 4. In aspects, the invention contemplates a combinatorial library comprising compounds for decreasing or reversing one or more of the following: inflammation (e.g. neuroinflammation), activation of signaling pathways involved in inflammation (e.g., neuroinflammation), cell signaling molecule production, activation of glia or glial activation pathways and responses, proinflammatory cytokines or chemokines (e.g., interleukin (IL) or tumor necrosis factor (TNF), oxidative stress-related responses such as nitric oxide synthase production and nitric oxide accumulation, acute phase proteins, components of the complement cascade, protein kinase activity (e.g., death associated protein kinase activity), cell damage (e.g., neuronal cell damage), and/or cell death (e.g., neuronal cell death), wherein the compounds comprise a structure of Formula I.

These and other aspects, features, and advantages of the present invention should be apparent to those skilled in the art from the following detailed description.

DETAILED DESCRIPTION OF EMBODIMENTS

Figure 1:
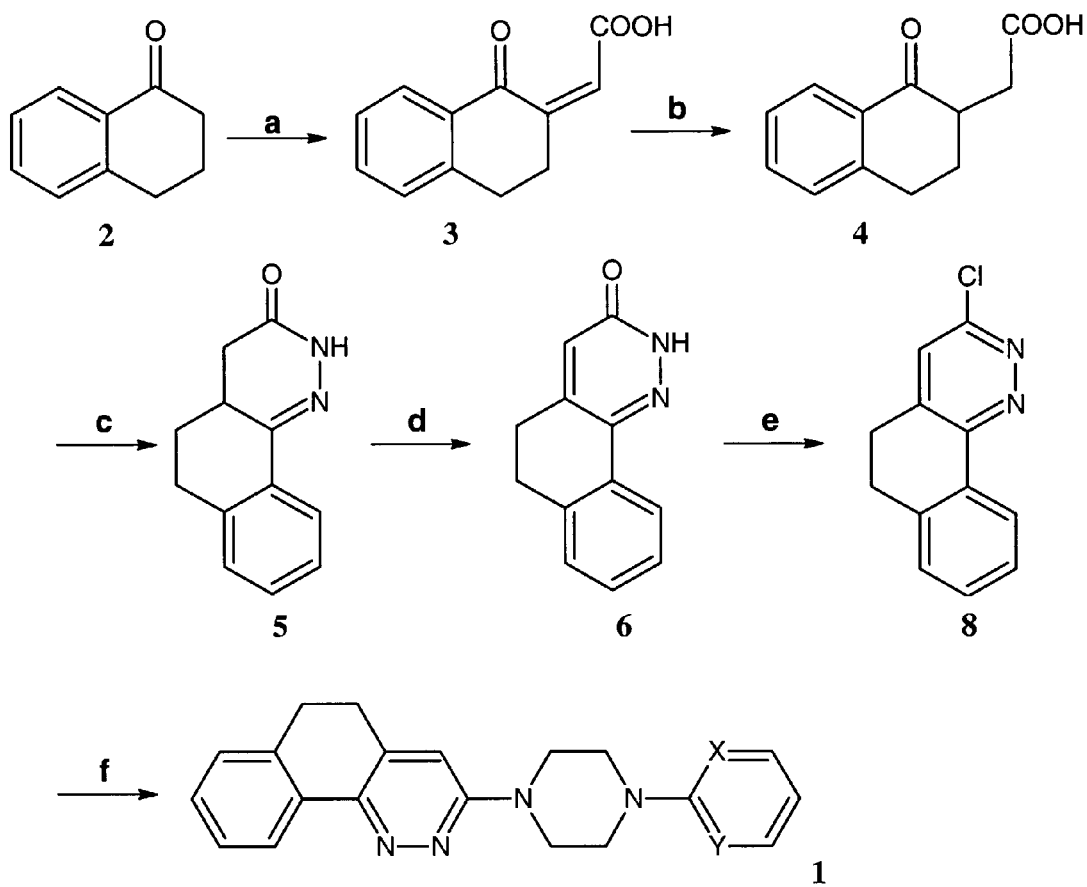
FIG. 1 depicts a synthetic scheme for synthesis of MW01-2-151WH and analogs with position 5 of the pyridazine ring linked to the aromatic ring at position 6. Reactions and conditions: (a) Glyoxylic acid, NaOH solution, EtOH, reflux; (b) Zn, HOAc, 110° C.; (c) NrfcNHi, EtOH, reflux; (d) CuCk, $CH_3CN$, reflux; (e) $POCl_3$, 95° C.; (f) 1-BuOH, NFL,C1,2-substituted-piperazine. 30

For convenience, certain terms employed in the specification, examples, and appended claims are collected here.

Numerical ranges recited herein by endpoints include all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about." The term "about" means plus or minus 0.1 to 50%, 5-50%, or 10-40%, preferably 10-20%, more preferably 10% or 15%, of the number to which reference is being made. Further, it is to be understood that "a," "an," and "the" include plural referents unless the content clearly dictates otherwise. Thus, for example, reference to a composition comprising "a compound" includes a mixture of two or more compounds.

As used herein the terms "administering" and "administration" refer to a process by which a therapeutically effective amount of a compound or composition contemplated herein is delivered to a subject for prevention and/or treatment purposes. Compositions are administered in accordance with good medical practices taking into account the subject's clinical condition, the site and method of administration, dosage, patient age, sex, body weight, and other factors known to physicians.

As used herein, the term "co-administration" refers to the administration of at least two compounds or agent(s) (e.g., compound of the Formula I or pyridazines) or therapies to a subject. In some embodiments, the co-administration of two or more agents/therapies is concurrent. In other embodiments, a first agent/therapy is administered prior to a second agent/therapy. Those of skill in the art understand that the formulations and/or routes of administration of the various agents/therapies used may vary. The appropriate dosage for co-administration can be readily determined by one skilled in the art. In some embodiments, when agents/therapies are co-administered, the respective agents/therapies are administered at lower dosages than appropriate for their administration alone. Thus, co-administration is especially desirable in embodiments where the co-administration of the agents/therapies lowers the requisite dosage of a known potentially harmful (e.g., toxic) agent(s).

The term "treating" refers to reversing, alleviating, or inhibiting the progress of a disease, or one or more symptoms of such disease, to which such term applies. Depending on the condition of the subject, the term also refers to preventing a disease, and includes preventing the onset of a disease, or preventing the symptoms associated with a disease. A treatment may be either performed in an acute or chronic way. The term also refers to reducing the severity of a disease or symptoms associated with such disease prior to affliction with the disease. Such prevention or reduction of the severity of a disease prior to affliction refers to administration of a compound or composition of the present invention to a subject that is not at the time of administration afflicted with the disease. "Preventing" also refers to preventing the recurrence of a disease or of one or more symptoms associated with such disease. "Treatment" and "therapeutically," refer to the act of treating, as "treating" is defined above.

The terms "subject", "individual", or "patient" are used interchangeably herein and refer to an animal preferably a warm-blooded animal such as a mammal. Mammal includes without limitation any members of the Mammalia. In general, the terms refer to a human. The terms also include domestic animals bred for food or as pets, including equines, bovines, sheep, poultry, fish, porcines, canines, felines, and zoo animals, goats, apes (e.g. gorilla or chimpanzee), and rodents such as rats and mice.

In aspects of the invention, the terms refer to organisms to be treated by the methods of the present invention. Such organisms preferably include, but are not limited to, mammals (e.g., murines, simians, equines, bovines, porcines, canines, felines, and the like), and most preferably includes humans. In the context of particular aspects of the invention, the term "subject" generally refers to an individual who will receive or who has received treatment (e.g., administration of a compound of the Formula I or a pyridazine compound(s), and optionally one or more other agents) for a condition characterized by inflammation, the dysregulation of protein kinase activity, and/or dysregulation of apototic processes.

Typical subjects for treatment include persons afflicted with or suspected of having or being pre-disposed to a disease disclosed herein, or persons susceptible to, suffering from or that have suffered a disease disclosed herein. A subject may or may not have a genetic predisposition for a disease disclosed herein such as Alzheimer's disease. In particular aspects, a subject shows signs of cognitive deficits and Alzheimer's disease neuropathology. In embodiments of the invention the subjects are susceptible to, or suffer from Alzheimer's disease.

As utilized herein, the term "healthy subject" means a subject, in particular a mammal, having no diagnosed disease, disorder, infirmity, or ailment, more particularly a disease, disorder, infirmity or ailment known to impair or otherwise diminish memory.

The term "diagnosed," as used herein, refers to the recognition of a disease by its signs and symptoms (e.g., resistance to conventional therapies), or genetic analysis, pathological analysis, histological analysis, and the like.

As used herein, the term "modulate" refers to the activity of a compound (e.g., a compound of the Formula I, or a pyridazine compound herein) to affect (e.g., to promote or retard) an aspect of cellular function, including, but not limited to, cell growth, proliferation, apoptosis, and the like.

A "beneficial effect" refers to an effect of a compound of the invention or composition thereof in certain aspects of the invention, including favorable pharmacological and/or therapeutic effects, and improved biological activity. In aspects of the invention, the beneficial effects include without limitation prevention, reduction, reversal, or inhibition of one or more of the following: inflammation (e.g. neuroinflammation), activation of signaling pathways involved in inflammation (e.g., neuroinflammation), cell signaling molecule production, activation of glia or glial activation pathways and responses, proinflammatory cytokines or chemokines (e.g., interleukin (IL) or tumor necrosis factor (TNF), oxidative stress-related responses such as nitric oxide synthase production and nitric oxide accumulation, acute phase proteins, components of the complement cascade, protein kinase activity (e.g., death associated protein kinase activity), cell damage (e.g., neuronal cell damage), and/or cell death (e.g., neuronal cell death). In some aspects, a beneficial effect is a favourable characteristic of a composition comprising a compound of the Formula I including without limitation enhanced stability, a longer half life, and/or enhanced uptake and transport across the blood brain barrier.

The beneficial effect can be a statistically significant effect in terms of statistical analysis of an effect of a compound of the Formula I versus the effects without the compound or compound that is not within the scope of the invention. Statistically significant" or "significantly different" effects or levels may represent levels that are higher or lower than a standard. In aspects of the invention, the difference may be 1.5, 2, 3, 4, 5, or 6 times higher or lower compared with the effect obtained without a compound of the Formula I.

The term "pharmaceutically acceptable carrier, excipient, or vehicle" refers to a medium which does not interfere with the effectiveness or activity of an active ingredient and which is not toxic to the hosts to which it is administered. A carrier, excipient, or vehicle includes diluents, binders, adhesives, lubricants, disintegrates, bulking agents, wetting or emulsifying agents, pH buffering agents, and miscellaneous materials such as absorbants that may be needed in order to prepare a particular composition. Examples of carriers etc. include but are not limited to saline, buffered saline, dextrose, water, glycerol, ethanol, and combinations thereof. The use of such media and agents for an active substance is well known in the art.

The compounds of the formula I disclosed herein also include "pharmaceutically acceptable salt(s)". By pharmaceutically acceptable salts is meant those salts which are suitable for use in contact with the tissues of a subject or patient without undue toxicity, irritation, allergic response and the like, and are commensurate with a reasonable benefit/risk ratio. Pharmaceutically acceptable salts are described for example, in S. M. Berge, et al., J. Pharmaceutical Sciences, 1977, 66:1

A compound of the Formula I can contain one or more asymmetric centers and may give rise to enantiomers, diastereomers, and other stereoisomeric forms which may be defined in terms of absolute stereochemistry as (R)- or (S)-. Thus, compounds of the formula I include all possible diastereomers and enantiomers as well as their racemic and optically pure forms. Optically active (R)- and (S)-isomers may be prepared using chiral synthons or chiral reagents, or resolved using conventional techniques.

When a compound of the formula I contains centers of geometric asymmetry, and unless specified otherwise, it is intended that the compounds include both E and A geometric isomers.

All tautomeric forms are also included within the scope of a compound of the Formula I.

A compound of the Formula I can exist in unsolvated as well as solvated forms with pharmaceutically acceptable solvents such as water, ethanol, and the like. The solvated forms may be considered equivalent to the unsolvated forms for the purposes of the present invention.

"Therapeutically effective amount" relates to the amount or dose of an active compound of the Formula I or composition comprising the same, that will lead to one or more desired effects, in particular, one or more therapeutic effects, more particularly beneficial effects. A therapeutically effective amount of a substance can vary according to factors such as the disease state, age, sex, and weight of the subject, and the ability of the substance to elicit a desired response in the subject. A dosage regimen may be adjusted to provide the optimum therapeutic response (e.g. sustained beneficial effects). For example, several divided doses may be administered daily or the dose may be proportionally reduced as indicated by the exigencies of the therapeutic situation.

As used herein, the term "pure" in general means better than 95% pure, and "substantially pure" means a compound synthesized such that the compound, as made or as available for consideration into a composition or therapeutic dosage described herein, has only those impurities that can not readily nor reasonably be removed by conventional purification processes.

The term "derivative" of a compound, as used herein, refers to a chemically modified compound wherein the chemical modification takes place either at a functional group of the compound or on the aromatic ring. Non-limiting examples of derivatives of compounds of the Formula I (e.g., pyridazine derivatives of the present invention) may include N-acetyl, N-methyl, N-hydroxy groups at any of the available nitrogens in the compound.

A "polymer" refers to molecules comprising two or more monomer subunits that may be identical repeating subunits or different repeating subunits. A monomer generally comprises a simple structure, low-molecular weight molecule containing carbon. Polymers may optionally be substituted. Polymers that can be used in the present invention include without limitation vinyl, acryl, styrene, carbohydrate derived polymers, polyethylene glycol (PEG), polyoxyethylene, polymethylene glycol, poly-trimethylene glycols, polyvinylpyrrolidone, polyoxyethylene-polyoxypropylene block polymers, and copolymers, salts, and derivatives thereof. In aspects of the invention, the polymer is poly(2-acrylamido-2-methyl-1-propanesulfonic acid); poly(2-acrylamido-2-methyl,-1-propanesulfonic acid-coacrylonitrile, poly(2-acrylamido-2-methyl-1-propanesulfonic acid-co-styrene), poly(vinylsulfonic acid); poly(sodium 4-styrenesulfonic acid); and sulfates and sulfonates derived therefrom; poly(acrylic acid), poly(methylacrylate), poly(methyl methacrylate), and poly(vinyl alcohol).

A "carbohydrate" as used herein refers to a polyhydroxy-aldehyde, or polyhydroxyketone and derivatives thereof. The term includes monosaccharides such as erythrose, arabinose, allose, altrose, glucose, mannose, threose, xylose, gulose, idose, galactose, talose, aldohexose, fructose, ketohexose, ribose, and aldopentose. The term also includes carbohydrates composed of monosaccharide units, including disaccharides, oligosaccharides, or polysaccharides. Examples of disaccharides are sucrose, lactose, and maltose. Oligosaccharides generally contain between 3 and 9 monosaccharide units and polysaccharides contain greater than 10 monosaccharide units. A carbohydrate group may be substituted at one two, three or four positions, other than the position of linkage to a compound of the Formula I. For example, a carbohydrate may be substituted with one or more alkyl, amino, nitro, halo, thiol, carboxyl, or hydroxyl groups, which are optionally substituted. Illustrative substituted carbohydrates are glucosamine, or galactosamine. In aspects of the invention, the carbohydrate is a sugar, in particular a hexose or pentose and may be an aldose or a ketose. A sugar may be a member of the D or L series and can include amino sugars, deoxy sugars, and their uronic acid derivatives. In embodiments of the invention where the carbohydrate is a hexose, the hexose is glucose, galactose, or mannose, or substituted hexose sugar residues such as an amino sugar residue such as hexosamine, galactosamine, glucosamine, in particular D-glucosamine (2-amino-2-doexy-D-glucose) or D-galactosamine (2-amino-2-deoxy-D-galactose). Illustrative pentose sugars include arabinose, fucose, and ribose.

A sugar residue may be linked to a compound of the Formula I from a 1,1 linkage, 1,2 linkage, 1,4 linkage, 1,5 linkage, or 1,6 linkage. A linkage may be via an oxygen atom of a compound of the Formula I. An oxygen atom can be replaced one or more times by —$CH_2$— or —S— groups.

The term "carbohydrate" also includes glycoproteins such as lectins (e.g. concanavalin A, wheat germ agglutinin, peanutagglutinin, seromucoid, and orosomucoid) and glycolipids such as cerebroside and ganglioside.

A "peptide" carrier for use in the practice of the present invention includes one, two, three, four, or five or more amino acids covalently linked through a peptide bond. A peptide can comprise one or more naturally occurring amino acids, and analogs, derivatives, and congeners thereof. A peptide can be modified to increase its stability, bioavailability, solubility, etc. "Peptide analogue" and "peptide derivative" as used herein include molecules which mimic the chemical structure of a peptide and retain the functional properties of the peptide. A carrier for use in the present invention can be an amino acid such as alanine, glycine, proline, methionine, serine, threonine, histidine, asparagine, alanyl-alanyl, prolyl-methionyl, or glycyl-glycyl. A carrier can be a polypeptide such as albumin, antitrypsin, macroglobulin, haptoglobin, caeruloplasm, transferring, $\alpha$- or $\beta$-lipoprotein, $\beta$- or $\gamma$-globulin or fibrinogen.

Approaches to designing peptide analogues, derivatives and mimetics are known in the art. For example, see Farmer, P. S. in Drug Design (E. J. Ariens, ed.) Academic Press, New York, 1980, vol. 10, pp. 119-143; Ball. J. B. and Alewood, P. F. (1990) J Mol. Recognition 3:55; Morgan, B. A. and Gainor, J. A. (1989) Ann. Rep. Med. Chem. 24:243; and Freidinger, R. M. (1989) Trends Pharmacol. Sci. 10:270. See also Sawyer, T. K. (1995) "Peptidomimetic Design and Chemical Approaches to Peptide Metabolism" in Taylor, M. D. and Amidon, G. L. (eds.) Peptide-Based Drug Design: Controlling Transport and Metabolism, Chapter 17; Smith, A. B. 3rd, et al. (1995) J. Am. Chem. Soc. 117:11113-11123; Smith, A. B. 3rd, et al. (1994) J. Am. Chem. Soc. 116:9947-9962; and Hirschman, R., et al. (1993) J. Am. Chem. Soc. 115:12550-12568.

A peptide can be attached to a compound of the Formula I through a functional group on the side chain of certain amino acids (e.g. serine) or other suitable functional groups. A carrier may comprise four or more amino acids with groups attached to three or more of the amino acids through functional groups on side chains. In an aspect, the carrier is one amino acid, in particular a sulfonate derivative of an amino acid, for example cysteic acid.

The term "alkyl", either alone or within other terms such as "thioalkyl" and "arylalkyl", means a monovalent, saturated hydrocarbon radical which may be a straight chain (i.e. linear) or a branched chain. An alkyl radical for use in the present invention generally comprises from about 1 to 20 carbon atoms, particularly from about 1 to 10, 1 to 8 or 1 to 7, more particularly about 1 to 6 or 3 to 6 carbon atoms. Illustrative alkyl radicals include methyl, ethyl, n-propyl, n-butyl, n-pentyl, n-hexyl, isopropyl, isobutyl, isopentyl, amyl, sec-butyl, tert-butyl, tert-pentyl, n-heptyl, n-octyl, n-nonyl, n-decyl, undecyl, n-dodecyl, n-tetradecyl, pentadecyl, n-hexadecyl, heptadecyl, n-octadecyl, nonadecyl, eicosyl, dosyl, n-tetracosyl, and the like, along with branched variations thereof. In certain aspects of the invention an alkyl radical is a $C_1$-$C_6$ lower alkyl comprising or selected from the group consisting of methyl, ethyl, n-propyl, n-butyl, n-pentyl, n-hexyl, isopropyl, isobutyl, isopentyl, amyl, tributyl, sec-butyl, tert-butyl, tert-pentyl, and n-hexyl. An alkyl radical may be optionally substituted with substituents as defined herein at positions that do not significantly interfere with the preparation of compounds of the formula I and do not significantly reduce the efficacy of the compounds. In certain aspects of the invention, an alkyl radical is substituted with one to five substituents including halo, lower alkoxy, lower aliphatic, a substituted lower aliphatic, hydroxy, cyano, nitro, thio, amino, keto, aldehyde, ester, amide, substituted amino, carboxyl, sulfonyl, sulfinyl, sulfenyl, sulfate, sulfoxide, substituted carboxyl, halogenated lower alkyl (e.g. $CF_3$), halogenated lower alkoxy, hydroxycarbonyl, lower alkoxycarbonyl, lower alkylcarbonyloxy, lower alkylcarbonylamino, cycloaliphatic, substituted cycloaliphatic, or aryl (e.g., phenylmethyl (i.e. benzyl)). Substituents on an alkyl group may themselves be substituted.

As used herein in respect of certain aspects of the invention, the term "substituted aliphatic" refers to an alkyl or an alkane possessing less than 10 carbons where at least one of the aliphatic hydrogen atoms has been replaced by a halogen, an amino, a hydroxy, a nitro, a thio, a ketone, an aldehyde, an ester, an amide, a lower aliphatic, a substituted lower aliphatic, or a ring (aryl, substituted aryl, cycloaliphatic, or substituted cycloaliphatic, etc.). Examples of such groups include, but are not limited to, 1-chloroethyl and the like.

As used herein in respect to certain aspects of the invention, the term "lower-alkyl-substituted-amino" refers to any alkyl unit containing up to and including eight carbon atoms where one of the aliphatic hydrogen atoms is replaced by an amino group. Examples of such include, but are not limited to, ethylamino and the like.

As used herein in respect to certain aspects of the invention, the term "lower-alkyl-substituted-halogen" refers to any alkyl chain containing up to and including eight carbon atoms where one of the aliphatic hydrogen atoms is replaced by a halogen. Examples of such include, but are not limited to, chlorethyl and the like.

As used herein, the term "acetylamino" shall mean any primary or secondary amino that is acetylated. Examples of such include, but are not limited to, acetamide and the like.

As used herein the term "alkenyl" refers to an unsaturated, acyclic branched or straight-chain hydrocarbon radical comprising at least one double bond. An alkenyl radical may contain from about 2 to 10 carbon atoms, in particular from about 3 to 8 carbon atoms and more particularly about 3 to 6 carbon atoms. Suitable alkenyl radicals include without limitation ethenyl, propenyl (e.g., prop-1-en-1-yl, prop-1-en-2-yl, prop-2-en-1-yl (allyl), prop-2-en-2-yl), buten-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, hexen-1-yl, 3-hydroxyhexen-1-yl, hepten-1-yl, and octen-1-yl, and the like. An alkenyl radical may be optionally substituted similar to alkyl.

As used herein, the term "alkynyl" refers to an unsaturated, branched or straight-chain hydrocarbon radical comprising one or more triple bonds. An alkynyl radical may contain about 1 to 20, 1 to 15, or 2-10 carbon atoms, particularly about 3 to 8 carbon atoms and more particularly about 3 to 6 carbon atoms. Suitable alkynyl radicals include without limitation ethynyl, such as prop-1-yn-1-yl, prop-2-yn-1-yl, butynyls such as but-1-yn-1-yl, but-1-yn-3-yl, but-3-yn-1-yl, pentynyls such as pentyn-1-yl, pentyn-2-yl, 4-methoxypentyn-2-yl, 3-methylbutyn-1-yl, hexynyls such as hexyn-1-yl, hexyn-2-yl, hexyn-3-yl, and 3,3-dimethylbutyn-1-yl radicals and the like. An alkenyl may be optionally substituted similar to alkyl. The term "cycloalkynyl" refers to cyclic alkynyl groups.

As used herein the term "alkylene" refers to a linear or branched radical having from about 1 to 10 carbon atoms and having attachment points for two or more covalent bonds. Examples of such radicals are methylene, ethylene, propylene, butylene, pentylene, hexylene, ethylidene, methylethylene, and isopropylidene. When an alkenylene radical is present as a substituent on another radical it is typically considered to be a single substituent rather than a radical formed by two substituents.

As used herein the term "alkenylene" refers to a linear or branched radical having from about 2 to 10 carbon atoms, at least one double bond, and having attachment points for two or more covalent bonds. Examples of alkenylene radicals include 1,1-vinylidene (—$CH_2$=C—), 1,2-vinylidene (—CH=CH—), and 1,4-butadienyl (—CH=CH—CH=CH—).

As used herein the term "halo" refers to a halogen such as fluorine, chlorine, bromine or iodine atoms.

As used herein the term "hydroxyl" or "hydroxy" refers to an —OH group.

As used herein the term "cyano" refers to a carbon radical having three of four covalent bonds shared by a nitrogen atom, in particular —C≡N. A cyano group may be substituted with substituents described herein.

As used herein the term "alkoxy" refers to a linear or branched oxy-containing radical having an alkyl portion of one to about ten carbon atoms, such as a methoxy radical, which may be substituted. In aspects of the invention an alkoxy radical may comprise about 1-10, 1-8 or 1-6 carbon atoms. In embodiments of the invention, an alkoxy radical comprises about 1-6 carbon atoms and includes a $C_1$-$C_6$ alkyl-O-radical wherein $C_1$-$C_6$ alkyl has the meaning set out herein. Examples of alkoxy radicals include without limitation methoxy, ethoxy, propoxy, butoxy, isopropoxy and tert-butoxy alkyls. An "alkoxy" radical may optionally be substituted with one or more substitutents disclosed herein including alkyl atoms to provide "alkylalkoxy" radicals; halo atoms, such as fluoro, chloro or bromo, to provide "haloalkoxy" radicals (e.g. fluoromethoxy, chloromethoxy, trifluoromethoxy, difluoromethoxy, trifluoroethoxy, fluoroethoxy, tetrafluoroethoxy, pentafluoroethoxy, and fluoropropox) and "haloalkoxyalkyl" radicals (e.g. fluoromethoxymethyl, chloromethoxyethyl, trifluoromethoxymethyl, difluoromethoxyethyl, and trifluoroethoxymethyl).

As used herein the term "alkenyloxy" refers to linear or branched oxy-containing radicals having an alkenyl portion of about 2 to 10 ten carbon atoms, such as an ethenyloxy or propenyloxy radical. An alkenyloxy radical may be a "lower alkenyloxy" radical having about 2 to 6 carbon atoms. Examples of alkenyloxy radicals include without limitation ethenyloxy, propenyloxy, butenyloxy, and isopropenyloxy alkyls. An "alkenyloxy" radical may be substituted with one or more substitutents disclosed herein including halo atoms, such as fluoro, chloro or bromo, to provide "haloalkenyloxy" radicals (e.g. trifluoroethenyloxy, fluoroethenyloxy, difluoroethenyhloxy, and fluoropropenyloxy).

A "carbocylic" includes radicals derived from a saturated or unsaturated, substituted or unsubstituted 5 to 14 member organic nucleus whose ring forming atoms (other than hydrogen) are solely carbon. Examples of carbocyclic radicals are cycloalkyl, cycloalkenyl, aryl, in particular phenyl, naphthyl, norbornanyl, bicycloheptadienyl, toluoyl, xylenyl, indenyl, stilbenzyl, terphenylyl, diphenylethylenyl, phenylcyclohexyl, acenapthylenyl, anthracenyl, biphenyl, bibenzylyl, and related bibenzylyl homologs, octahydronaphthyl, tetrahydronaphthyl, octahydroquinolinyl, dimethoxytetrahydronaphthyl and the like.

As used herein, the term "cycloalkyl" refers to radicals having from about 3 to 15 carbon atoms and containing one, two, three, or four rings wherein such rings may be attached in a pendant manner or may be fused, in particular cyclopropyl, cyclobutyl, cyclopentyl, cyclohexyl, cycloheptyl, cyclooctyl, cyclononyl, adamantyl, and the like. In certain aspects of the invention the cycloalkyl radicals are "lower cycloalkyl" radicals having from about 3 to 8 carbon atoms, in particular cyclopropyl, cyclobutyl, cyclopentyl, cyclohexyl and cycloheptyl. In some aspects of the invention the term "cycloalkyl" embraces radicals where cycloalkyl radicals are fused with aryl radicals or heterocyclyl radicals. A cycloalkyl radical may be optionally substituted with groups as disclosed herein.

As used herein in respect to certain aspects of the invention, the term "cycloaliphatic" refers to a cycloalkane possessing less than 8 carbons or a fused ring system consisting of no more than three fused cycloaliphatic rings. Examples of such include, but are not limited to, decalin and the like.

As used herein in respect to certain aspects of the invention, the term "substituted cycloaliphatic" refers to a cycloalkane possessing less than 8 carbons or a fused ring system consisting of no more than three fused rings, and where at least one of the aliphatic hydrogen atoms has been replaced by a halogen, a nitro, a thio, an amino, a hydroxy, a ketone, an aldehyde, an ester, an amide, a lower aliphatic, a substituted lower aliphatic, or a ring (aryl, substituted aryl, cycloaliphatic, or substituted cycloaliphatic). Examples of such include, but are not limited to, 1-chlorodecalyl and the like.

A used herein, the term "cycloalkenyl" refers to radicals comprising about 2 to 15 carbon atoms, one or more carbon-carbon double bonds, and one, two, three, or four rings wherein such rings may be attached in a pendant manner or may be fused. In certain aspects of the invention the cycloalkenyl radicals are "lower cycloalkenyl" radicals having three to seven carbon atoms. Examples of cycloalkenyl radicals include without limitation cyclobutenyl, cyclopentenyl, cyclohexenyl and cycloheptenyl. A cycloalkenyl radical may be optionally substituted with groups as disclosed herein, in particular 1, 2, or 3 substituents which may be the same or different.

As used herein the term "cycloalkoxy" refers to cycloalkyl radicals attached to an oxy radical. Examples of cycloalkoxy radicals include cyclohexoxy and cyclopentoxy. A cycloalkoxy radical may be optionally substituted with groups as disclosed herein.

As used herein, the term "aryl", alone or in combination, refers to a carbocyclic aromatic system containing one, two or three rings wherein such rings may be attached together in a pendant manner or may be fused. The term "fused" means that a second ring is present (i.e, attached or formed) by having two adjacent atoms in common or shared with the first ring. An aryl radical may be optionally substituted with groups as disclosed herein, in particular hydroxyl, alkyl, carbonyl, carboxyl, thiol, amino, and/or halo, in particular a substituted aryl includes without limitation arylamine and arylalkylamine. Illustrative "aryl" radicals includes without limitation aromatic radicals such as phenyl, benzyl, naphthyl, indenyl, benzocyclooctenyl, benzocycloheptenyl, pentalenyl, azulenyl, tetrahydronaphthyl, indanyl, biphenyl, acephthylenyl, fluorenyl, phenalenyl, phenanthrenyl, and anthracenyl.

As used herein in respect to certain aspects of the invention, the term "substituted aryl" refers to an aromatic ring, or fused aromatic ring system consisting of no more than three fused rings at least one of which is aromatic, and where at least one of the hydrogen atoms on a ring carbon has been replaced by a halogen, an amino, a hydroxy, a nitro, a thio, an alkyl, a ketone, an aldehyde, an ester, an amide, a lower aliphatic, a substituted lower aliphatic, or a ring (aryl, substituted aryl, cycloaliphatic, or substituted cycloaliphatic). Examples of such include, but are not limited to, hydroxyphenyl, chlorophenyl and the like.

As used herein, the term "aryloxy" refers to aryl radicals, as defined above, attached to an oxygen atom. Exemplary aryloxy groups include napthyloxy, quinolyloxy, isoquinolizinyloxy, and the like.

As used herein the term "arylalkoxy," refers to an aryl group attached to an alkoxy group. Representative examples of arylalkoxy include, but are not limited to, 2-phenylethoxy, 3-naphth-2-ylpropoxy, and 5-phenylpentyloxy.

As used herein, the term "aroyl" refers to aryl radicals, as defined above, attached to a carbonyl radical as defined herein, including without limitation benzoyl and toluoyl. An aroyl radical may be optionally substituted with groups as disclosed herein.

As used herein the term "heteroaryl" refers to fully unsaturated heteroatom-containing ring-shaped aromatic radicals having at least one heteroatom selected from carbon, nitrogen, sulfur and oxygen. A heteroaryl radical may contain one, two or three rings and the rings may be attached in a pendant manner or may be fused. Examples of "heteroaryl" radicals, include without limitation, an unsaturated 5 to 6 membered heteromonocyclyl group containing 1 to 4 nitrogen atoms, in particular, pyrrolyl, pyrrolinyl, imidazolyl, pyrazolyl, 2-pyridyl, 3-pyridyl, 4-pyridyl, pyridinyl, pyrimidinyl, pyrazinyl, pyridazinyl, triazolyl, tetrazolyl and the like; an unsaturated condensed heterocyclic group containing 1 to 5 nitrogen atoms, in particular, indolyl, isoindolyl, indolizinyl, indazolyl, quinazolinyl, pteridinyl, quinolizidinyl, phthalazinyl, naphthyridinyl, quinoxalinyl, cinnolinyl, phenanthridinyl, acridinyl, phenanthrolinyl, phenazinyl, carbazolyl, purinyl, benzimidazolyl, quinolyl, isoquinolyl, quinolinyl, isoquinolinyl, indazolyl, benzotriazolyl, tetrazolopyridazinyl and the like; an unsaturated 3 to 6-membered heteromonocyclic group containing an oxygen atom, in particular, 2-furyl, 3-furyl, pyranyl, and the like; an unsaturated 5 to 6-membered heteromonocyclic group containing a sulfur atom, in particular, thienyl, 2-thienyl, 3-thienyl, and the like; unsaturated 5 to 6-membered heteromonocyclic group containing 1 to 2 oxygen atoms and 1 to 3 nitrogen atoms, in particular, furazanyl, benzofurazanyl, oxazolyl, isoxazolyl, and oxadiazolyl; an unsaturated condensed heterocyclic group containing 1 to 2 oxygen atoms and 1 to 3 nitrogen atoms, in particular benzoxazolyl, benzoxadiazolyl and the like; an unsaturated 5 to 6-membered heteromonocyclic group containing 1 to 2 sulfur atoms and 1 to 3 nitrogen atoms, for example, thiazolyl, isothiazolyl, thiadiazolyl and the like; an unsaturated condensed heterocyclic group containing 1 to 2 sulfur atoms and 1 to 3 nitrogen atoms such as benzothiazolyl, benzothiadiazolyl and the like. The term also includes radicals where heterocyclic radicals are fused with aryl radicals, in particular bicyclic radicals such as benzofuranyl, benzothiophenyl, phthalazinyl, chromenyl, xanthenyl, and the like. A heteroaryl radical may be optionally substituted with groups as disclosed herein, for example with an alkyl, amino, halogen, etc., in particular a heteroarylamine.

The term "heterocyclic" refers to saturated and partially saturated heteroatom-containing ring-shaped radicals having at least one heteroatom selected from carbon, nitrogen, sulfur and oxygen. A heterocylic radical may contain one, two or three rings wherein such rings may be attached in a pendant manner or may be fused. Exemplary saturated heterocyclic radicals include without limitation a saturated 3 to 6-membered heteromonocylic group containing 1 to 4 nitrogen atoms [e.g. pyrrolidinyl, imidazolidinyl, piperidinyl, and piperazinyl]; a saturated 3 to 6-membered heteromonocyclic group containing 1 to 2 oxygen atoms and 1 to 3 nitrogen atoms [e.g. morpholinyl; sydnonyl]; and, a saturated 3 to 6-membered heteromonocyclic group containing 1 to 2 sulfur atoms and 1 to 3 nitrogen atoms [e.g., thiazolidinyl] etc. Examples of partially saturated heterocyclyl radicals include without limitation dihydrothiophene, dihydropyranyl, dihydrofuranyl and dihydrothiazolyl. Illustrative heterocyclic radicals include without limitation aziridinyl, azetidinyl, 2-pyrrolinyl, 3-pyrrolinyl, pyrrolidinyl, azepinyl, 1,3-dioxolanyl, 2H-pyranyl, 4H-pyranyl, piperidinyl, 1,4-dioxanyl, morpholinyl, pyrazolinyl, 1,4-dithianyl, thiomorpholinyl, 1,2,3,6-tetrahydropyridinyl, oxiranyl, oxetanyl, tetrahydrofuranyl, tetrahydropyranyl, tetrahydropyridinyl, tetrahydrothiopyranyl, thioxanyl, indolinyl, 2H-pyranyl, 4H-pyranyl, dioxanyl, 1,3-dioxolanyl, pyrazolinyl, dihydropyranyl, dihydrothienyl, dihydrofuranyl, pyrazolidinyl, imidazolinyl, imidazolidinyl, 3H-indolyl, quinuclidinyl, quinolizinyl, and the like.

As used herein in respect to certain aspects of the invention, the term "heterocyclic" refers to a cycloalkane and/or an aryl ring system, possessing less than 8 carbons, or a fused ring system consisting of no more than three fused rings, where at least one of the ring carbon atoms is replaced by oxygen, nitrogen or sulfur. Examples of such include, but are not limited to, morpholino and the like.

As used herein in respect to certain aspects of the invention, the term "substituted heterocyclic" refers to a cycloalkane and/or an aryl ring system, possessing less than 8 carbons, or a fused ring system consisting of no more than three fused rings, where at least one of the ring carbon atoms is replaced by oxygen, nitrogen or sulfur, and where at least one of the aliphatic hydrogen atoms has been replaced by a halogen, hydroxy, a thio, nitro, an amino, a ketone, an aldehyde, an ester, an amide, a lower aliphatic, a substituted lower aliphatic, or a ring (aryl, substituted aryl, cycloaliphatic, or substituted cycloaliphatic). Examples of such include, but are not limited to 2-chloropyranyl.

The foregoing heteroaryl and heterocyclic groups may be C-attached or N-attached (where such is possible).

As used herein the term "sulfonyl", used alone or linked to other terms such as alkylsulfonyl or arylsulfonyl, refers to the divalent radicals —$SO_2$—. In aspects of the invention a sulfonyl group, the sulfonyl group may be attached to a substituted or unsubstituted hydroxyl, alkyl group, ether group, alkenyl group, alkynyl group, aryl group, cycloalkyl group, cycloalkenyl group, cycloalkynyl group, heterocyclic group, carbohydrate, peptide, or peptide derivative.

The term "sulfinyl", used alone or linked to other terms such as alkylsulfinyl (i.e. —S(O)— alkyl) or arylsulfinyl, refers to the divalent radicals —S(O)—.

As used herein he term "amino", alone or in combination, refers to a radical where a nitrogen atom (N) is bonded to three substituents being any combination of hydrogen, hydroxyl, alkyl, cycloalkyl, alkenyl, alkynyl, aryl, silyl, heterocyclic, or heteroaryl with the general chemical formula —$NR^{21}R^{22}$ where $R^{21}$ and $R^{22}$ can be any combination of hydrogen, hydroxyl, alkyl, cycloalkyl, alkoxy, alkenyl, alkynyl, aryl, carbonyl carboxyl, amino, silyl, heteroaryl, or heterocyclic which may or may not be substituted. Optionally one substituent on the nitrogen atom may be a hydroxyl group (—OH) to provide an amine known as a hydroxylamine. Illustrative examples of amino groups are amino (—$NH_2$), alkylamino, acylamino, cycloamino, acycloalkylamino, arylamino, arylalkylamino, and lower alkylsilylamino, in particular methylamino, ethylamiino, dimethylamino, 2-propylamino, butylamino, isobutylamino, cyclopropylamino, benzylamino, allylamino, hydroxylamino, cyclohexylamino, piperidinyl, hydrazinyl, benzylamino, diphenylmethylamino, tritylamino, trimethylsilylamino, and dimethyl-tert.-butylsilylamino, which may or may not be substituted.

As used herein the term "thiol" means —SH. A thiol may be substituted with a substituent disclosed herein, in particular alkyl (thioalkyl), aryl (thioaryl), alkoxy (thioalkoxy) or carboxyl.

The term "sulfenyl" used alone or linked to other terms such as alkylsulfenyl, refers to the radical —$SR^{24}$ wherein $R^{24}$ is not hydrogen. In aspects of the invention R is substituted or unsubstituted alkyl, cycloalkyl, alkenyl, alkynyl, aryl, silyl, heterocyclic, heteroaryl, carbonyl, or carboxyl.

As used herein, the term "thioalkyl", alone or in combination, refers to a chemical functional group where a sulfur atom (S) is bonded to an alkyl, which may be substituted. Examples of thioalkyl groups are thiomethyl, thioethyl, and thiopropyl. A thioalkyl may be substituted with a substituted or unsubstituted carboxyl, aryl, heterocyclic, or carbonyl.

As used herein the term "thioaryl", alone or in combination, refers to a chemical functional group where a sulfur atom (S) is bonded to an aryl group with the general chemical formula —$SR^{25}$ where $R^{25}$ is an aryl group which may be substituted. Illustrative examples of thioaryl groups and substituted thioaryl groups are thiophenyl, para-chlorothiophenyl, thiobenzyl, 4-methoxy-thiophenyl, 4-nitro-thiophenyl, and para-nitrothiobenzyl.

As used herein the term "thioalkoxy", alone or in combination, refers to a chemical functional group where a sulfur atom (S) is bonded to an alkoxy group with the general chemical formula —$SR^{30}$ where $R^{30}$ is an alkoxy group which may be substituted. A "thioalkoxy group" may have 1-6 carbon atoms i.e. a —S—(O)—$C_1$-$C_6$ alkyl group wherein $C_1$-$C_6$ alkyl have the meaning as defined above. Illustrative examples of a straight or branched thioalkoxy group or radical having from 1 to 6 carbon atoms, also known as a $C_1$-$C_6$ thioalkoxy, include thiomethoxy and thioethoxy.

As used herein, the term "carbonyl" refers to a carbon radical having two of the four covalent bonds shared with an oxygen atom.

As used herein, the term "carboxyl", alone or in combination, refers to —C(O)$OR^{14}$ or —C(=O)$OR^{14}$ wherein $R^{14}$ is hydrogen, alkyl, alkenyl, alkynyl, cycloalkyl, cycloalkenyl, amino, thiol, aryl, heteroaryl, thioalkyl, thioaryl, thioalkoxy, a heteroaryl, or a heterocyclic, which may optionally be substituted. Examples of carboxyl groups are methoxycarbonyl, butoxycarbonyl, tert.alkoxycarbonyl such as tert.butoxycarbonyl, arylmethyoxycarbonyl having one or two aryl radicals including without limitation phenyl optionally substituted by for example lower alkyl, lower alkoxy, hydroxyl, halo, and/or nitro, such as benzyloxycarbonyl, methoxybenxyloxycarbonyl, diphenylmethoxycarbonyl, 2-bromoethoxycarbonyl, 2-iodoethoxycarbonyltert.butylcarbonyl, 4-nitrobenzyloxycarbonyl, diphenylmethoxy-carbonyl, benzhydroxycarbonyl, di-(4-methoxyphenyl-methoxycarbonyl, 2-bromoethoxycarbonyl, 2-iodoethoxycarbonyl, 2-trimethylsilylethoxycarbonyl, or 2-triphenylsilylethoxycarbonyl. Additional carboxyl groups in esterified form are silyloxycarbonyl groups including organic silyloxycarbonyl. In aspects of the invention, the carboxyl group may be an alkoxy carbonyl, in particular methoxy carbonyl, ethoxy carbonyl, isopropoxy carbonyl, t-butoxycarbonyl, t-pentyloxycarbonyl, or heptyloxy carbonyl, especially methoxy carbonyl or ethoxy carbonyl.

As used herein, the term "carbamoyl", alone or in combination, refers to amino, monoalkylamino, dialkylamino, monocycloalkylamino, alkylcycloalkylamino, and dicycloalkylamino radicals, attached to one of two unshared bonds in a carbonyl group.

As used herein, the term "carboxamide" refers to the group —CONH—.

As used herein, the term "nitro" means —$NO_2$—.

As used herein, the term "acyl", alone or in combination, means a carbonyl or thiocarbonyl group bonded to a radical selected from, for example, optionally substituted, hydrido, alkyl (e.g. haloalkyl), alkenyl, alkynyl, alkoxy ("acyloxy" including acetyloxy, butyryloxy, iso-valeryloxy, phenylacetyloxy, benzoyloxy, p-methoxybenzoyloxy, and substituted acyloxy such as alkoxyalkyl and haloalkoxy), aryl, halo, heterocyclyl, heteroaryl, sulfinyl (e.g. alkylsulfinylalkyl), sulfonyl (e.g. alkylsulfonylalkyl), cycloalkyl, cycloalkenyl, thioalkyl, thioaryl, amino (e.g alkylamino or dialkylamino), and aralkoxy. Illustrative examples of "acyl" radicals are formyl, acetyl, 2-chloroacetyl, 2-bromacetyl, benzoyl, trifluoroacetyl, phthaloyl, malonyl, nicotinyl, and the like.

As used herein, "ureido" refers to the group "—NH-CONH—". A ureido radical includes an alkylureido comprising a ureido substituted with an alkyl, in particular a lower alkyl attached to the terminal nitrogen of the ureido group. Examples of an alkylureido include without limitation N'-methylureido, N'-ethylureido, N'-n-propylureido, N'-i-propylureido and the like. A ureido radical also includes a N',N'-dialkylureido group containing a radical —NHCON where the terminal nitrogen is attached to two optionally substituted radicals including alkyl, aryl, heterocylic, and heteroaryl.

The terms used herein for radicals including "alkyl", "alkoxy", "alkenyl", "alkynyl", "hydroxyl" etc. refer to both unsubstituted and substituted radicals. The term "substituted," as used herein, means that any one or more moiety on a designated atom (e.g., hydrogen) is replaced with a selection from a group disclosed herein, provided that the designated atom's normal valency is not exceeded, and that the substitution results in a stable compound. Combinations of substituents and/or radicals are permissible only if such combinations result in stable compounds. "Stable compound" refers to a compound that is sufficiently robust to survive isolation to a useful degree of purity from a reaction mixture, and formulation into an efficacious therapeutic agent.

A radical in a compound of the Formula I may be substituted with one or more substituents apparent to a person skilled in the art including without limitation alkyl, alkenyl, alkynyl, alkanoyl, alkylene, alkenylene, hydroxyalkyl, alkoxy, haloalkyl, haloalkylene, haloalkenyl, alkoxy, alkenyloxy, alkenyloxyalkyl, alkoxyalkyl, aryl, alkylaryl, haloalkoxy, haloalkenyloxy, heterocyclic, heteroaryl, sulfonyl, alkylsulfonyl, sulfinyl, sulfonyl, sulfenyl, alkylsulfinyl, aralkyl, heteroaralkyl, cycloalkyl, cycloalkenyl, cycloalkoxy, cycloalkenyloxy, amino, oxy, halo, azido, thio, cyano, hydroxyl, phosphonato, phosphinato, thioalkyl, alkylamino, arylamino, arylsulfonyl, alkylcarbonyl, arylcarbonyl, heteroarylcarbonyl, heteroarylsulfinyl, heteroarylsulfony, heteroarylamino, heteroaryloxy, heteroaryloxylalkyl, arylacetamidoyl, aryloxy, aroyl, aralkanoyl, aralkoxy, aryloxyalkyl, haloaryloxyalkyl, heteroaroyl, heteroaralkanoyl, heteroaralkoxy, heteroaralkoxyalkyl, thioaryl, arylthioalkyl, alkoxyalkyl, and acyl groups. These substituents may themselves be substituted.

A "disease" that can be treated and/or prevented using a compound, composition, or method of the invention includes a condition associated with or requiring modulation of one or more of inflammation (e.g. neuroinflammation), signaling pathways involved in inflammation (e.g., neuroinflammation), cell signaling molecule production, activation of glia or glial activation pathways and responses, proinflammatory cytokines or chemokines (e.g., interleukin (IL) or tumor necrosis factor (TNF), oxidative stress-related responses such as nitric oxide synthase production and nitric oxide accumulation, acute phase proteins, components of the complement cascade, protein kinase activity (e.g., death associated protein kinase (DAPK) activity), cell damage (e.g., neuronal cell damage), and cell death (e.g., neuronal cell death). In particular a disease is a dementing disorder, a neurodegenerative disorder, a CNS demyelinating disorder, an autoimmune disorder, or a peripheral inflammatory disease.

A disease may be characterized by an inflammatory process due to the presence of macrophages activated by an amyloidogenic protein or peptide. Thus, a method of the invention may involve inhibiting macrophage activation and/or inhibiting an inflammatory process. A method may comprise decreasing, slowing, ameliorating, or reversing the course or degree of macrophage invasion or inflammation in a patient.

Examples of diseases that can be treated and/or prevented using the compounds, compositions and methods of the invention include Alzheimer's disease and related disorders, presenile and senile forms; amyloid angiopathy; mild cognitive impairment; Alzheimer's disease-related dementia (e.g., vascular dementia or Alzheimer dementia); AIDS related dementia, tauopathies (e.g., argyrophilic grain dementia, corticobasal degeneration, dementia pugilistica, diffuse neurofibrillary tangles with calcification, frontotemporal dementia with parkinsonism, Prion-related disease, Hallervorden-Spatz disease, myotonic dystrophy, Niemann-Pick disease type C, non-Guamanian Motor Neuron disease with neurofibrillary tangles, Pick's disease, postencephalitic parkinsonism, cerebral amyloid angiopathy, progressive subcortical gliosis, progressive supranuclear palsy, subacute sclerosing panencephalitis, and tangle only dementia), alpha-synucleinopathy (e.g., dementia with Lewy bodies, multiple system atrophy with glial cytoplasmic inclusions), multiple system atrophies, Shy-Drager syndrome, spinocerebellar ataxia (e.g., DRPLA or Machado-Joseph Disease); striatonigral degeneration, olivopontocerebellar atrophy, neurodegeneration with brain iron accumulation type I, olfactory dysfunction, and amyotrophic lateral sclerosis); Parkinson's disease (e.g., familial or non-familial); Amyotrophic Lateral Sclerosis; Spastic paraplegia (e.g., associated with defective function of chaperones and/or triple A proteins); Huntington's Disease, spinocerebellar ataxia, Freidrich's Ataxia; cerebrovascular diseases including stroke, hypoxia, ischemia, infarction, intracerebral hemorrhage; traumatic brain injury; Down's syndrome; head trauma with post-traumatic accumulation of amyloid beta peptide; Familial British Dementia; Familial Danish Dementia; Presenile Dementia with Spastic Ataxia; Cerebral Amyloid Angiopathy, British Type; Presenile Dementia With Spastic Ataxia Cerebral Amyloid Angiopathy, Danish Type; Familial encephalopathy with neuroserpin inclusion bodies (FENIB); Amyloid Polyneuropathy (e.g., senile amyloid polyneuropathy or systemic Amyloidosis); Inclusion Body myositis due to amyloid beta peptide;

Familial and Finnish Type Amyloidosis; Systemic amyloidosis associated with multiple myeloma; Familial Mediterranean Fever; multiple sclerosis; optic neuritis; Guillain-Barre Syndrome; chronic inflammatory demyelinating polyneuropathy; chronic infections and inflammations; acute disseminated encephalomyelitis (ADEM); autoimmune inner ear disease (AIED); diabetes; myocardial ischemia and other cardiovascular disorders; pancreatitis; gout; inflammatory bowel disease; ulcerative colitis; Crohn's disease; rheumatoid arthritis; osteoarthritis; artheriosclerosis; inflammatory aortic aneurysm; asthma; adult respiratory distress syndrome; restenosis; ischemia/reperfusion injury; glomerulonephritis; sacoidosis cancer; restenosis; rheumatic fever; systemic lupus erythematosus; Reiter's syndrome; psoriatic arthritis; ankylosing spondylitis; coxarthritis; pelvic inflammatory disease; osteomyelitis; adhesive capsulitis; oligoarthritis; periarthritis; polyarthritis; psoriasis; Still's disease; synovitis; inflammatory dermatosis; and, wound healing.

In aspects of the invention, a compound, composition, or method disclosed herein may be utilized to prevent and/or treat a disease involving neuroinflammation (i.e., neuroinflammatory disease). Neuroinflammation is a characteristic feature of disease pathology and progression in a diverse array of neurodegenerative disorders that are increasing in their societal impact (for a recent review, see, e.g., Prusiner, S. B. (2001) New Engl. J. Med. 344, 1516-1526). These neuroinflammation-related disorders include Alzheimer's disease (AD), amyotrophic lateral sclerosis, autoimmune disorders, priori diseases, stroke and traumatic brain injury. Neuroinflammation is brought about by glial cell (e.g., astrocytes and microglia) activation, which normally serves a beneficial role as part of an organism's homeostatic response to injury or developmental change. However, disregulation of this process through chronic or excessive activation of glia contributes to the disease process through the increased production of proinflammatory cytokines and chemokines, oxidative stress-related enzymes, acute phase proteins, and various components of the complement cascades. (See, e.g., Akiyama et al., (2000) Neurobiol. Aging 21, 383-421). The direct linkage of glial activation to pathology that is a hallmark of disease underscores the importance of understanding the signal transduction pathways that mediate these critical glial cellular responses and the discovery of cell permeable ligands that can modulate these disease relevant pathways.

For Alzheimer's disease (AD) in particular, the deposition of β-amyloid (Aβ) and neurofibrillary tangles are associated with glial activation, neuronal loss and cognitive decline. On a molecular level, Alzheimer's disease is characterized by; increased expression of nitric oxide synthase (NOS) in glial cells surrounding amyloid plaques; neuropathological evidence of peroxynitrite-mediated neuronal damage; and nitric oxide (NO) overproduction involved in Aβ-induced brain dysfunction. NOS (iNOS) is induced as part of the glial activation response and is an oxidative stress-related enzyme that generates NO. When NO is present in high levels along with superoxide, the highly reactive NO-derived molecule peroxynitrite is generated, leading to neuronal cell death. The pro-inflammatory cytokine IL-1β is also overexpressed in activated glia in AD brain and polymorphisms in IL-1β genes are associated with an increased risk of early onset sporadic AD (See, e.g., Du et al., (2000) Neurology 55, 480-483). IL-1β can also influence amyloid plaque development and is involved in additional glial inflammatory and neuronal dysfunction responses (See, e.g., Griffin, et al., (1998) Brain Pathol. 8, 65-72; and Sheng, et al., (1996) Neurobiol. Aging 17, 761-766). Therefore, because glial activation and specific glial products are associated with neurodegenerative disorders (e.g., Alzheimer's disease), the compounds and compositions disclosed herein that are capable of modulating cell signaling pathways (e.g., glial activation pathways) will have particular application in the treatment and prevention of inflammatory disease.

In aspects of the invention, a compound, composition, or method disclosed herein may be utilized to prevent and/or treat a disease involving disregulation of protein kinase signaling. Disregulation of protein kinase signaling often accompanies disregulation of cell signaling pathways (e.g., glial cell activation pathways). Protein kinases are a large family of proteins that play a central role in regulating a number of cellular functions including cell growth, differentiation and death. There are thought to be more than 500 protein kinases and 130 protein phosphatases exerting tight control on protein phosphorylation. Each protein kinase transfers the γ-phosphate of ATP to a specific residue(s) of a protein substrate. Protein kinases can be further categorized as tyrosine, serine/threonine or dual specific based on acceptor residue. Examples of serine/threonine kinases include MAP kinase, MAPK kinase (MEK), Akt/PKB, Jun kinase (INK), CDKs, protein kinase A (PRA), protein kinase C (PKC), and calmodulin (CaM)-dependent kinases (CaMKs). Disregulated protein kinase activity (e.g., hyper- or hypoactive) leads to abnormal protein phosphorylation, underlying a great number of diseases including diabetes, rheumatoid arthritis, inflammation, hypertension, and proliferative diseases such as cancer. Therefore, because aberrant kinase activity is associated with inflammatory disease (e.g., neurodegenerative disorders like Alzheimer's disease), the compounds and compositions that are disclosed herein that are capable of modulating kinases involved in cell signaling pathways will have particular application for treatment and prevention of inflammatory disease.

Compounds

The invention provides an isolated and pure, in particular, substantially pure, compound of the Formula I, wherein $R^1$, $R^2$, $R^3$ and $R^4$ are independently substituted or unsubstituted hydrogen, hydroxyl, alkyl, alkenyl, alkynyl, alkylene, alkenylene, alkoxy, alkenyloxy, cycloalkyl, cycloalkenyl, aryl, aryloxy, arylalkoxy, aroyl, heteroaryl, heterocyclic, acyl, acyloxy, sulfonyl, sulfinyl, sulfenyl, amino, imino, azido, thiol, thioalkyl, thioalkoxy, thioaryl, nitro, ureido, cyano, halo, silyl, silyloxy, silylthio, carboxyl, carboxamide, carbonyl, or carbamoyl; or $R^4$ may be absent and there is a double bond between N at position 2 and C at position 3, or an isomer or a pharmaceutically acceptable salt thereof.

In aspects of the invention, a compound of the Formula I does not include compounds depicted in Table 3.

In another aspect of the invention, a compound of the Formula I is contemplated wherein $R^1$, $R^2$, $R^3$ and $R^4$ are independently substituted or unsubstituted hydrogen, hydroxyl, alkyl, alkenyl, alkynyl, alkylene, alkenylene, alkoxy, alkenyloxy, cycloalkyl, cycloalkenyl, aryl, aryloxy, arylalkoxy, aroyl, heteroaryl, heterocyclic, acyl, acyloxy, sulfonyl, sulfinyl, sulfenyl, amino, imino, azido, thiol, thioalkyl, thioalkoxy, thioaryl, nitro, ureido, cyano, halo, silyl, silyloxy, silylthio, carboxyl, carboxamide, carbonyl, or carbamoyl or $R^4$ may be absent and there is a double bond between N at position 2 and C at position 3; provided that (i) when $R^2$ and $R^3$ are hydrogen and $R^4$ is absent, then $R^1$ is not chloro, —$SCH_2CH_2N(CH_2CH_3)_2$, or —$NR^{21}R^{22}$ wherein $R^{21}$ is ethyl and $R^{22}$ is morpholinyl, piperidinyl substituted with benzyl, —$CH_2N(CH_2CH_3)_2$ or —$N(CH_2CH_3)_2$, or $R^{21}$ is hydrogen and $R^{22}$ is —$NH_2$ or hydrogen; (ii) when $R^3$ is hydrogen, $R^4$ is absent, and $R^1$ is =O, then $R^2$ is not —COOH or —C(=O)—OCH$_2$CH$_3$; and (iii) when R$^3$ is hydrogen, R$^4$ is absent, and R$^1$ is chloro, then R$^2$ is not methyl.

In an embodiment, a compound of the Formula I does not include a compound wherein R$^1$ is a substituted heteromonocyclic group containing 1-4 nitrogen atoms, in particular piperazinyl substituted with pyrimidinyl, R$^2$ and R$^3$ are hydrogen, and R$^4$ is absent.

In an embodiment, a compound of the Formula I does not include a compound wherein R$^1$ is piperazinyl substituted with pyrimidinyl, R$^2$ and R$^3$ are hydrogen, and R$^4$ is absent.

In another aspect, a compound of the Formula I is contemplated wherein R$^1$ is a heterocyclic group which may have one or more suitable substitutents, and optionally R$^2$ is hydrogen, an alkoxy carbonyl, in particular methoxy carbonyl, ethoxy carbonyl, isopropoxy carbonyl, t-butoxycarbonyl, t-pentyloxycarbonyl, or heptyloxy carbonyl, especially methoxy carbonyl or ethoxy carbonyl, or an alkylamino carbonyl, R$^3$ is hydrogen or alkyl, and R$^4$ is hydrogen or absent. In a particular aspect, R$^1$ is a substituted or unsubstituted heteromonocyclic group containing 1-4 nitrogen atoms, in particular pyrrolidinyl, imidazolidinyl, piperidinyl, or piperazinyl, more particularly piperazinyl. In an embodiment, a heteromonocyclic group containing 1-4 nitrogen atoms may be substituted with heteroaryl, aryl, alkyl, or a heterocyclic each of which may be substituted. In a particular embodiment, R$^1$ is piperazinyl substituted with a substituted or unsubstituted unsaturated 5-6 membered heteromonocyclyl group containing 1-4 nitrogen atoms such as pyrimidinyl, pyridyl or pyridinyl especially pyrimidinyl; aryl or substituted aryl especially phenyl or phenylalkyl, in particular benzyl; or alkyl such as C$_1$-C$_6$ alkyl. In another particular embodiment, R$^1$ is piperidinyl substituted with a heterocyclicoxy such as an unsaturated 5-6 membered heteromonocyclyl group containing 1-4 nitrogen atoms and substituted with oxy, in particular —O-pyrimidinyl, —O-pyridyl, or O-pyridinyl, especially —O-pyrimidinyl.

In an embodiment, a compound of the Formula I is contemplated wherein R$^1$ is a heterocyclic group which may have one or more suitable substitutents, in particular piperazinyl substituted with pyrimidinyl, and R$^2$ is hydrogen, an alkoxy carbonyl, in particular methoxy carbonyl, ethoxy carbonyl, isopropoxy carbonyl, t-butoxycarbonyl, t-pentyloxycarbonyl, or heptyloxy carbonyl, especially methoxy carbonyl or ethoxy carbonyl, or alkylamino carbonyl, R$^3$ is hydrogen, and R$^4$ is hydrogen.

In an embodiment, a compound of the Formula I is contemplated wherein R$^1$ is a heterocyclic group which may have one or more suitable substitutents, in particular piperazinyl substituted with pyrimidinyl, and R$^2$ is carboxyamidyl or substituted carboxyamidyl, R$^3$ is hydrogen, and R$^4$ is hydrogen or absent.

In another aspect, a compound of the Formula I is contemplated wherein R$^1$ is a 3-6 membered heteromonocyclic group containing 1-2 oxygen atoms and 1-3 nitrogen atoms which may have one or more suitable substitutents, and optionally R$^2$ is hydrogen or an alkoxy carbonyl, in particular methoxy carbonyl, ethoxy carbonyl, isopropoxy carbonyl, t-butoxycarbonyl, t-pentyloxycarbonyl, or heptyloxy carbonyl, especially methoxy carbonyl or ethoxy carbonyl, R$^3$ is hydrogen or alkyl, and R$^4$ is hydrogen. In an embodiment, R$^1$ is substituted or unsubstituted morpholinyl or sydnonyl, especially morpholinyl.

In another aspect, a compound of the Formula I is contemplated wherein R$^1$ is aryl which may have one or more suitable substitutents, and optionally R$^2$ is an alkoxy carbonyl, in particular methoxy carbonyl, ethoxy carbonyl, isopropoxy carbonyl, t-butoxycarbonyl, t-pentyloxycarbonyl, or heptyloxy carbonyl, especially methoxy carbonyl or ethoxy carbonyl, or a 3-6 membered heteromonocyclic group containing 1-2 oxygen atoms and 1-3 nitrogen atoms which may have one or more suitable substitutents, in particular morpholinyl, R$^3$ is hydrogen or alkyl, and R$^4$ is hydrogen. In an embodiment, R$^1$ is phenyl, benzyl, napthyl, indenyl, benzocyclooctenyl, benzocycloheptenyl, or pentalenyl, especially phenyl, benzyl, or napthyl which may be substituted.

In another aspect, a compound of the Formula I is contemplated wherein R$^1$ is an unsaturated condensed heterocyclic containing 1 to 5 nitrogen atoms which may have one or more suitable substitutents, and optionally R$^2$ is an alkoxy carbonyl, in particular methoxy carbonyl, ethoxy carbonyl, isopropoxy carbonyl, t-butoxycarbonyl, t-pentyloxycarbonyl, or heptyloxy carbonyl, especially methoxy carbonyl or ethoxy carbonyl, or a 3-6 membered heteromonocyclic group containing 1-2 oxygen atoms and 1-3 nitrogen atoms which may have one or more suitable substitutents, in particular morpholinyl, R$^3$ is hydrogen or alkyl, and R$^4$ is hydrogen. In an embodiment, R$^1$ is indolyl, isoindolyl, indolizinyl, purinyl, or benzimidazolyl which may be substituted with halo or alkyl.

In another aspect, a compound of the Formula I is contemplated wherein R$^1$ is halo especially chloro, and optionally R$^2$ is hydrogen, halo, an alkoxy carbonyl, in particular methoxy carbonyl, ethoxy carbonyl, isopropoxy carbonyl, t-butoxycarbonyl, t-pentyloxycarbonyl, or heptyloxy carbonyl, especially methoxy carbonyl or ethoxy carbonyl, a 3-6 membered heteromonocyclic group containing 1-2 oxygen atoms and 1-3 nitrogen atoms which may have one or more suitable substitutents, in particular morpholinyl, carboxyl which may be substituted with a substituted or unsubstituted heterocyclic in particular a 3-6 membered heteromonocyclic group containing 1-2 oxygen atoms and 1-3 nitrogen atoms which may have one or more suitable substitutents, in particular morpholinyl or morpholinyl substituted with halo, alkyl, carboxy, or an alkoxy carbonyl, or —NR$^{21}$R$^{22}$ wherein R$^{21}$ is hydrogen and R$^{22}$ is substituted alkyl, especially methyl substituted with one or more alkyl or cycloalkyl, in particular methyl, dimethyl, cyclopropyl or cyclobutyl, R$^3$ is hydrogen or alkyl, and R$^4$ is hydrogen.

In another aspect, a compound of the Formula I is contemplated wherein R$^1$ is amino which may have one or more suitable substitutents, and optionally R$^2$ is hydrogen or an alkoxy carbonyl, in particular methoxy carbonyl, ethoxy carbonyl, isopropoxy carbonyl, t-butoxycarbonyl, t-pentyloxycarbonyl, or heptyloxy carbonyl, especially methoxy carbonyl or ethoxy carbonyl, R$^3$ is hydrogen or alkyl, and R$^4$ is hydrogen or alkyl, especially C$_1$-C$_6$ or C$_1$-C$_3$ alkyl which may be substituted for example with an alkoxy carbonyl, in particular methoxy carbonyl, ethoxy carbonyl, isopropoxy carbonyl, t-butoxycarbonyl, t-pentyloxycarbonyl, or heptyloxy carbonyl, especially methoxy carbonyl or ethoxy carbonyl.

In an embodiment, R$^1$ is —NR$^{21}$R$^{22}$ wherein R$^{21}$ is hydrogen and R$^{22}$ is hydrogen, C$_1$-C$_6$ alkyl in particular methyl, ethyl or butyl, aryl in particular phenyl, benzyl, or napthyl, substituted aryl in particular aryl substituted with alkyl or halo, substituted alkyl in particular C$_1$-C$_6$ alkyl substituted with a heterocyclic more particularly a substituted or unsubstituted unsaturated condensed heterocyclic group containing 1 to 5 nitrogen atoms.

In a particular embodiment, R$^1$ is —NR$^{21}$R$^{22}$ wherein R$^{21}$ is hydrogen and R$^{22}$ is hydrogen, R$^2$ and R$^3$ are hydrogen, and R$^4$ is alkyl, in particular C$_1$-C$_6$ alkyl which may be substituted with an alkoxy carbonyl, in particular methoxy carbonyl, ethoxy carbonyl, or isopropoxy carbonyl.

In another particular embodiment, $R^1$ is —$NR^{21}R^{22}$ wherein $R^{21}$ is hydrogen and $R^{22}$ is aryl, in particular phenyl or benzyl, which may be substituted with alkyl or halo.

In a further particular embodiment, $R^1$ is —$NR^{21}R^{22}$ wherein $R^{21}$ is hydrogen and $R^{22}$ is aryl, in particular phenyl or benzyl, which may be substituted with halo, and $R^2$, $R^3$, and $R^4$ are hydrogen.

In a still further particular embodiment, $R^1$ is —$NR^{21}R^{22}$ wherein $R^{21}$ is hydrogen and $R^{22}$ is alkyl substituted with a heterocylic more particularly a substituted or unsubstituted saturated 3 to 6-membered heteromonocylic group containing 1 to 4 nitrogen atoms more particularly pyrrolidinyl, imidazolidinyl, piperidinyl, and piperazinyl, which heterocyclic may be substituted with alkyl, substituted alkyl, halo, aryl, or substituted aryl, more particularly aryl (e.g., phenyl or benzyl) which may be substituted with halo or alkyl, and $R^2$, $R^3$, and $R^4$ are hydrogen.

In a still further embodiment, $R^1$ is =O, and $R^2$ is —C(=O)$R^{40}$ wherein $R^{40}$ is a 3-6 membered heteromonocyclic group containing 1-2 oxygen atoms and 1-3 nitrogen atoms which may have one or more suitable substitutents, in particular morpholinyl or $NR^{21}R^{22}$ wherein $R^{21}$ is hydrogen and $R^{22}$ is alkyl substituted with an unsaturated condensed heterocyclic containing 1 to 5 nitrogen atoms which may have one or more suitable substituents, more particularly indolyl, isoindolyl, indolizinyl, purinyl, or benzimidazolyl which may be substituted.

In an aspect of the invention, a compound of the Formula I is provided wherein $R^1$ is hydrogen, halo, carbonyl, substituted carbonyl, piperazinyl, substituted piperazinyl, piperidinyl, substituted piperidinyl, naphthyl, indolyl, morpholinyl, substituted purinyl, amino, substituted amino, thioalkyl or substituted thioalkyl. In an embodiment of the invention $R^1$ is piperazinyl substituted with one or more of alkyl, phenyl, substituted phenyl, pyrimidinyl, substituted pyrimidinyl, or pyridinyl. In another embodiment of the invention $R^1$ is —$NHR^{21}$ wherein $R^{21}$ is hydrogen, alkyl, substituted alkyl, phenyl, substituted phenyl, in particular a —$NH_2$, —$NHCH_2$-purinyl, —NH-chlorophenyl, NH-benzimidazolyl, or —$NHCH_2CH_2$-piperazinyl-benzyl.

In an aspect of the invention, a compound of the Formula I is provided wherein $R^2$ is hydrogen, halo, or optionally substituted carboxyl, carbonyl, piperazinyl, morpholinyl, or amino. In an embodiment, $R^2$ is —$COR^6$ wherein $R^6$ is hydroxyl, amino, substituted amino, morpholinyl, substituted morpholinyl, or alkoxy, in particular —$CONHCH_2$— benzimidazolyl, piperazinyl substituted with pyrimidinyl, —CO-morpholinyl substituted with carboxyl or substituted carboxyl, —$COOCH_2CH_3$, or —$NHCH(CH_3)_2$.

In aspects of the invention, a compound of the Formula I is provided wherein $R^3$ is hydrogen or alkyl, in particular $C_1$-$C_6$ alkyl, more particularly methyl or ethyl.

In aspects of the invention, a compound of the Formula I is provided wherein $R^4$ is alkyl substituted with a carboxyl or substituted carboxyl (e.g., $CH_2CH_2CH_2COOCH_2CH_3$).

In an aspect of the invention a compound of the Formula I is provided wherein $R^1$ is halo, =O; indolyl, amino, or piperazinyl which may be substituted; $R^2$ is —$COR^6$ wherein $R^6$ is hydroxyl, alkoxy or morpholinyl which may be substituted; and $R^3$ is hydrogen or alkyl, or a pharmaceutically acceptable salt thereof.

In an aspect, the invention provides a compound of the following Formula I wherein $R^1$ is piperinzinyl substituted with pyrimidinyl which may be substituted with one or more of hydrogen, alkyl, substituted alkyl, phenyl, substituted phenyl, arylalkyl, substituted arylalkyl, halogen, amino, heterocyclic, substituted heterocyclic, cycloalkyls, hydroxy, amine, substituted amine, arylamine, heteroarylamine, arylalkylamine, hydrazinyl, substituted hydrazinyl, pyrimidinyl and substituted pyrimidinyl, pyridinyl and substituted pyridinyl, pyrazinyl and substituted pyrazinyl, thienyl and substituted thienyl, thiazolyl and substituted thiazolyl, pyrazolyl and substituted pyrazolyl, stilbenzyl and substituted stilbenzyl, imidazolyl and substituted imidazolyl, phthalazine and substituted phthalazine, piperazinyl and/or substituted piperazinyl moieties.

In particular aspects of the invention, a compound of the Formula I is provided wherein
a) $R^1$ is halide and $R^3$ is alkyl, in particular lower alkyl;
b) $R^1$ is =O, $R^2$ is —$CONHCH_2$— benzimidazolyl, and $R^3$ is hydrogen;
c) $R^1$ is =O or halo, $R^2$ is —$COR^6$ wherein $R^6$ is substituted morpholinyl and R3 is hydrogen;
d) $R^1$ is indolyl, $R^2$ is —$COR^6$ wherein $R^6$ is alkoxy, in particular lower alkoxy, and $R^3$ is hydrogen;
e) $R^1$ is substituted piperazinyl, in particular piperazinyl substituted with optionally substituted alkyl or phenyl, $R^2$ is —$COR^6$ wherein $R^6$ is alkoxy, and $R^3$ is hydrogen;
f) $R^1$ is piperazinyl substituted with optionally substituted pyrimidinyl, $R^2$ is —$COR^6$ wherein $R^6$ is alkoxy, and $R^3$ is hydrogen;
g) $R^1$ is piperidinyl which may be substituted, in particular —O-pyrimidinyl, $R^2$ is hydrogen, and $R^3$ is hydrogen;
h) $R^1$ is substituted piperazinyl, $R^2$ is hydrogen, and $R^3$ is hydrogen;
i) $R^1$ is halo, $R^2$ is piperazinyl substituted with pyrimidinyl, and $R^3$ is hydrogen;
j) $R^1$ and $R^2$ are halo, in particular —Cl, and $R^3$ is hydrogen;
k) $R^1$ is halo, $R^2$ is alkylamino substituted with cyclopropyl, and $R^3$ is hydrogen;
l) $R^1$ is halo, $R^2$ is morpholinyl, and $R^3$ is hydrogen;
m) $R^1$ is halo, $R^2$ is —$NHC(CH_3)_2$ and $R^3$ is hydrogen;
n) $R^1$ is naphthy or indolyl; $R^2$ is morpholinyl, and $R^3$ is hydrogen;
o) $R^1$ is halo, $R^2$ is carboxyl or substituted carboxyl (e.g., —$COOCH_2CH_3$), and $R^3$ is hydrogen;
p) $R^1$ is piperazinyl substituted with pyridinyl, $R^2$ is hydrogen, carboxyl or substituted carboxyl (e.g., —$COOCH_2CH_3$ or a carboxamide such as —$CONHC(CH_3)_2$), and $R^3$ is hydrogen;
q) $R^1$ is morpholinyl, $R^2$ is hydrogen, and $R^3$ is hydrogen;
r) $R^1$ is halo, $R^2$ is hydrogen, and $R^3$ is alkyl, in particular lower alkyl.
s) $R^1$ is amino, $R^2$ and $R^3$ are hydrogen, and $R^4$ is alkyl substituted with a carboxyl or substituted carboxyl (e.g., $CH_2CH_2CH_2COOCH_2CH_3$); or
t) $R^1$ is halo, $R^2$ is hydrogen, and $R^3$ is alkyl, in particular lower alkyl.

In embodiments of the invention, compounds of the Formula I are provided wherein $R^1$, $R^2$, and/or $R^3$ are as defined above, and in particular are defined as in (a) to (t) above, and $R^4$ is absent and there is a double bond between N at position 2 and C at position 3.

In some embodiments, the present invention provides novel organic compounds, and/or heterocyclic derivatives thereof, represented in the Figures and Tables, in particular Table 4. In some embodiments, compounds encompassed by the present invention include triazine compounds comprising the structures 3-chloro-5,6-dihydrobenzo[h]cinnoline (FIG. 1, compound 7).

Derivative groups that may be used to modify the compounds of the present invention can be found in U.S. Patent Application No. 20030176437 (herein incorporated by reference in its entirety for all purposes).

A compound of the formula I may be in the form of a prodrug that is converted in vivo to an active compound. For example, in a compound of the formula I one or more of $R^1$, $R^2$, $R^3$, and $R^4$ may comprise a cleavable group that is cleaved after administration to a subject to provide an active (e.g., therapeutically active) compound, or an intermediate compound that subsequently yields the active compound. A cleavable group can be an ester that is removed either enzymatically or non-enzymatically.

A compound of the Formula I may comprise a carrier, such as one or more of a polymer, carbohydrate, peptide or derivative thereof, which may be directly or indirectly covalently attached to the compound. A carrier may be substituted with substituents described herein including without limitation one or more alkyl, amino, nitro, halogen, thiol, thioalkyl, sulfate, sulfonyl, sulfinyl, sulfoxide, hydroxyl groups. In aspects of the invention the carrier is an amino acid including alanine, glycine, praline, methionine, serine, threonine, asparagines, alanyl-alanyl, prolyl-methionyl, or glycyl-glycyl. A carrier can also include a molecule that targets a compound of the formula I to a particular tissue or organ. Thus, a carrier may facilitate or enhance transport of a compound of the formula I to the brain.

Process

Compounds of the formula I can be prepared using reactions and methods generally known to the person of ordinary skill in the art, having regard to that knowledge and the disclosure of this application including the Examples. The reactions are performed in a solvent appropriate to the reagents and materials used and suitable for the reactions being effected. It will be understood by those skilled in the art of organic synthesis that the functionality present on the compounds should be consistent with the proposed reaction steps. This will sometimes require modification of the order of the synthetic steps or selection of one particular process scheme over another in order to obtain a desired compound of the invention. It will also be recognized that another major consideration in the development of a synthetic route is the selection of the protecting group used for protection of the reactive functional groups present in the compounds described in this invention. An authoritative account describing the many alternatives to the skilled artisan is Greene and Wuts (Protective Groups In Organic Synthesis, Wiley and Sons, 1991).

The starting materials and reagents used in preparing compounds or the invention are either available from commercial suppliers or are prepared by methods well known to a person of ordinary skill in the art, following procedures described in such references as Fieser and Fieser's *Reagents for Organic Synthesis*, vols. 1-17, John Wiley and Sons, New York, N.Y., 1991; *Rodd's Chemistry of Carbon Compounds*, vols. 1-5 and supps., Elsevier Science Publishers, 1989; Organic Reactions, vols. 1-40, John Wiley and Sons, New York, N.Y., 1991; March J.: *Advanced Organic Chemistry*, 4th ed., John Wiley and Sons, New York, N.Y.; and Larock: *Comprehensive Organic Transformations*, VCH Publishers, New York, 1989.

The starting materials, intermediates, and compounds of the formula I may be isolated and purified using conventional techniques, such as precipitation, filtration, distillation, crystallization, chromatography, and the like. The compounds of the formula I may be characterized using conventional methods, including physical constants and spectroscopic methods, in particular HPLC.

The compounds of the Formula I which are basic in nature can form a wide variety of different salts with various inorganic and organic acids. In practice is it desirable to first isolate a compound of the Formula I from the reaction mixture as a pharmaceutically unacceptable salt and then convert the latter to the free base compound by treatment with an alkaline reagent and subsequently convert the free base to a pharmaceutically acceptable acid addition salt. The acid addition salts of the base compounds of the Formula I are readily prepared by treating the base compound with a substantially equivalent amount of the chosen mineral or organic acid in an aqueous solvent medium or in a suitable organic solvent such as methanol or ethanol. Upon careful evaporation of the solvent, the desired solid salt is obtained.

Compounds of the Formula I which are acidic in nature are capable of forming base salts with various pharmacologically acceptable cations. These salts may be prepared by conventional techniques by treating the corresponding acidic compounds with an aqueous solution containing the desired pharmacologically acceptable cations and then evaporating the resulting solution to dryness, preferably under reduced pressure. Alternatively, they may be prepared by mixing lower alkanolic solutions of the acidic compounds and the desired alkali metal alkoxide together and then evaporating the resulting solution to dryness in the same manner as before. In either case, stoichiometric quantities of reagents are typically employed to ensure completeness of reaction and maximum product yields.

In particular aspects, the present invention provides methods of making the compounds depicted in the Table 2, comprising the steps provided (See, e.g., FIG. 1 and Materials and Methods).

As part of the synthetic scheme used to generate the compounds of the formula I, diversification of position 3 of the pyridazine ring was done by reaction of common halogenated pyridazine precursor. The common precursor, 3-chloro-5,6-dihydrobenzo[h]cinnoline (FIG. 1, compound 7), prepared using a combination of previously reported methods [12-16], was used to make multiple compounds (See, e.g., MW01-2-151WH, MW01-3-202WH, and MW01-3-173WH). As detailed in Materials and Methods below, compounds were synthesized with yields of 81-96%. All purified compounds were characterized by HPLC, mass spectrometry and NMR in order to confirm syntheses.

Therefore the invention provides a process for preparing a compound of the formula I comprising reacting a compound of the formula II

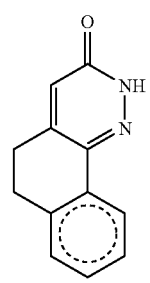

under suitable conditions and with suitable reagents to introduce the radicals $R^1$, $R^2$, $R^3$ and $R^4$ which are independently substituted or unsubstituted hydrogen, hydroxyl, alkyl, alkenyl, alkynyl, alkylene, alkenylene, alkoxy, alkenyloxy, cycloalkyl, cycloalkenyl, aryl, aryloxy, arylalkoxy, aroyl, heteroaryl, heterocyclic, acyl, acyloxy, sulfonyl, sulfinyl, sulfenyl, amino, imino, azido, thiol, thioalkyl, thioalkoxy, thioaryl, nitro, ureido, cyano, halo, silyl, silyloxy, silylthio, carboxyl, carboxamide, carbonyl, or carbamoyl; or a pharmaceutically acceptable salt thereof.

In an aspect, a compound of the formula II is reacted under suitable conditions and with suitable reagents to introduce at $R^2$ an alkoxy carbonyl, in particular methoxy carbonyl or ethoxy carbonyl, or carboxyl in particular —C(=O)$R^{40}$ wherein $R^{40}$ is a 3-6 membered heteromonocyclic group containing 1-2 oxygen atoms and 1-3 nitrogen atoms which may have one or more suitable substitutents, in particular morpholinyl or $NR^{21}R^{22}$ wherein $R^{21}$ is hydrogen and $R^{22}$ is alkyl substituted with an unsaturated condensed heterocyclic containing 1 to 5 nitrogen atoms which may have one or more suitable substitutents, more particularly indolyl, isoindolyl, indolizinyl, purinyl, or benzimidazolyl which may be substituted.

A compound of the formula II may be reacted with a chloride to provide a compound of the formula III chlorinated at the pyriazone:

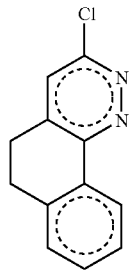

III

A compound of the formula III may be reacted under suitable conditions and with suitable reagents to introduce a halo, carboxyl, substituted carboxyl, amino, aryl, substituted aryl, heterocyclic, or substituted heterocyclic at $R^2$ and/or optionally an alkyl at $R^3$. In aspects of this process of the invention, $R^2$ is a piperazinyl, substituted piperazinyl, piperadinyl, substituted piperadinyl, indolyl, morpholinyl, napthyl or —$NR^{21}R^{22}$ wherein $R^{21}$ is hydrogen and $R^{22}$ is hydrogen, $C_1$-$C_6$ alkyl in particular methyl, ethyl or butyl; aryl, in particular phenyl, benzyl, or napthyl; substituted aryl in particular aryl substituted with alkyl or halo; substituted alky, in particular $C_1$-$C_6$ alkyl substituted with a heterocyclic more particularly a substituted or unsubstituted unsaturated condensed heterocyclic group containing 1 to 5 nitrogen atoms or unsubstituted saturated 3 to 6-membered heteromonocylic group containing 1 to 4 nitrogen atoms which heterocyclic may be substituted with alkyl, substituted alkyl, halo, aryl, or substituted aryl.

In an aspect, the invention provides a process for preparing a compound of the formula I wherein $R^2$, $R^3$ and $R^4$ are hydrogen and $R^1$ is an amino, substituted amino, heterocyclic, or substituted heterocyclic, in particular a piperazinyl or substituted piperazinyl more particular piperazinyl substituted with alkyl, phenyl, substituted phenyl, pyrimidinyl, or pyridinyl, comprising reacting a compound of the formula III under amination conditions with amino, substituted amino, heterocyclic, or substituted heterocyclic, in particular a piperazinyl or substituted piperazinyl to produce a compound of the formula I, and optionally reacting the compound of the formula I under suitable conditions to introduce an alkoxy carbonyl group or carboamidyl group at $R^1$. The resulting compound may be reacted under suitable conditions and reagents to introduce an alkoxy carbonyl, especially methoxy carbonyl or ethoxy carbonyl at $R^2$.

Figure 6:
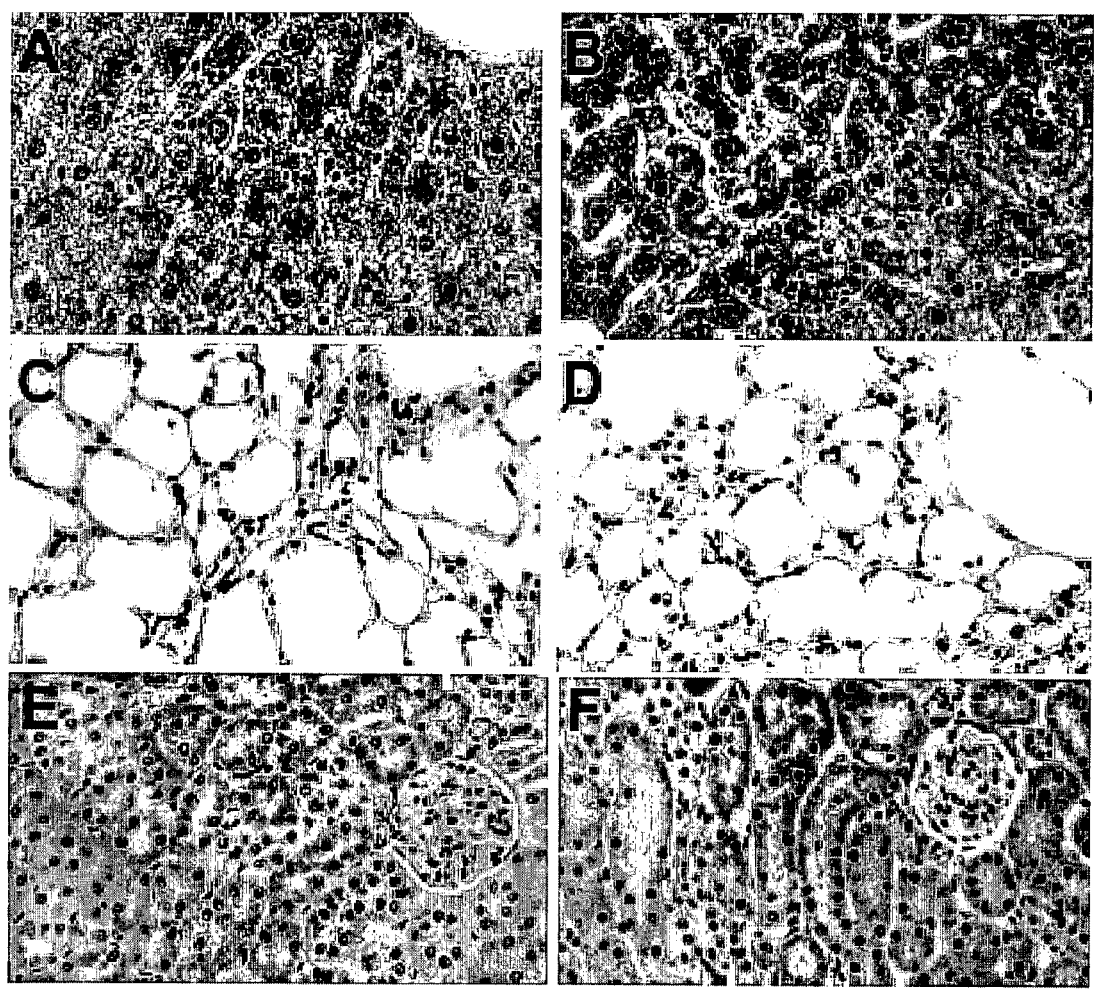
FIG. 6 A-F shows micrographs showing lack of tissue toxicity by orally administered MW01-2-151 WH at increasing doses up to 20-fold higher than a therapeutically effective dose. Vehicle (panels A,C,E) or MW01-2-151 WH (panels B,D,F) was orally administered (gavage) to mice daily for three days at 50 mg/kg (20-fold greater than a therapeutic dose, described in Materials and Methods). There was no histological evidence of toxicity in liver (A,B), lung (C,D), or kidney (E,F).

In an aspect, a compound of the formula I wherein $R^2$ is a carboxyl, a substituted carboxyl, a carboxamidyl or substituted carboxamidyl is prepared by a process comprising reacting a 3-chloro-5,6-dihydrobenzo[h]cinnoline substituted with a substituted carboxyl at $R^2$ (e.g., MW01-1-084B-WH in FIG. 6) with a pyrimidinyl substituted with piperazinyl under suitable conditions to produce a 3-(4-(pyrimidin-2yl) piperazin-1-yl)benzo[h]cinnoline substituted with a substituted carboxyl at $R^2$ (e.g., MW01-5-149WH in FIG. 6), and optionally reacting the resulting compound with suitable reagents to prepare a compound wherein $R^2$ is a carboxyl, carboxamidyl or substituted carboxamidyl.

In an embodiment, a compound of the Formula I wherein $R^1$ is a piperazinyl substituted with pyrimidinyl and $R^2$ is a substituted carboxamidyl, in particular a carboxamidyl substituted with an alkyl, in particular a dimethyl group, is prepared by a process comprising reacting a compound of the formula I wherein $R^1$ is a piperazinyl substituted with pyrimidinyl and $R^2$ is a carboxyl under suitable conditions with thionyl chloride and isopropylamine to produce a compound of the Formula I wherein $R^1$ is a piperazinyl substituted with pyrimidinyl and $R^2$ is a substituted carboxamidyl, in particular a carboxamidyl substituted with an alkyl, in particular a dimethyl group.

Therapeutic efficacy and toxicity of compounds, compositions and methods of the invention may be determined by standard pharmaceutical procedures in cell cultures or with experimental animals such as by calculating a statistical parameter such as the $ED_{50}$ (the dose that is therapeutically effective in 50% of the population) or $LD_{50}$ (the dose lethal to 50% of the population) statistics. The therapeutic index is the dose ratio of therapeutic to toxic effects and it can be expressed as the $ED_{50}/LD_{50}$ ratio. Pharmaceutical compositions which exhibit large therapeutic indices are preferred. By way of example, one or more of the therapeutic effects, in particular beneficial effects disclosed herein, can be demonstrated in a subject or disease model, for example, a TgCRND8 mouse with symptoms of Alzheimer's disease.

Biological investigations were done with compounds disclosed herein that were >95% homogenous as determined by HPLC/MS analysis. As part of a hierarchal, cell-based screening protocol, the compounds were screened for their ability to block IL-1β and TNFα production by BV-2 mouse microglial cells stimulated with LPS. The data for MW01-2-1-151WH and the three structurally related analogs (MW01-3-202WH and MW01-3-173WH,) is shown (See, e.g., FIG. 2). Derivative groups that may be used to modify the compounds of the present invention can be found in U.S. Patent Application No. 20030176437 (herein incorporated by reference in its entirety for all purposes).

The compounds disclosed herein can be tested for liver toxicity which is an important initial consideration for orally administered compounds since the liver is the major site of initial drug metabolism and is critical to overall metabolism and homeostasis of an animal. Compounds disclosed herein may also be tested for cardiac safety by testing for hERG channel inhibition.

Compositions and Kits

A compound of the Formula I of the invention may be formulated into a pharmaceutical composition for administration to a subject. Pharmaceutical compositions of the present invention or fractions thereof comprise suitable pharmaceutically acceptable carriers, excipients, and vehicles selected based on the intended form of administration, and consistent with conventional pharmaceutical practices. Suitable pharmaceutical carriers, excipients, and vehicles are described in the standard text, Remington's Pharmaceutical Sciences, Mack Publishing Company (Remington's Pharmaceutical Sciences, Mack Publishing Company, Easton, Pa., USA 1985). By way of example for oral administration in the form of a capsule or tablet, the active components can be combined with an oral, non-toxic pharmaceutically acceptable inert carrier such as lactose, starch, sucrose, methyl cellulose, magnesium stearate, glucose, calcium sulfate, dicalcium phosphate, mannitol, sorbital, and the like. For oral administration in a liquid form, the drug components may be combined with any oral, non-toxic, pharmaceutically acceptable inert carrier such as ethanol, glycerol, water, and the like. Suitable binders (e.g. gelatin, starch, corn sweeteners, natural sugars including glucose; natural and synthetic gums, and waxes), lubricants (e.g. sodium oleate, sodium stearate, magnesium stearate, sodium benzoate, sodium acetate, and sodium chloride), disintegrating agents (e.g. starch, methyl cellulose, agar, bentonite, and xanthan gum), flavoring agents, and coloring agents may also be combined in the compositions or components thereof. Compositions as described herein can further comprise wetting or emulsifying agents, or pH buffering agents.

A composition of the invention can be a liquid solution, suspension, emulsion, tablet, pill, capsule, sustained release formulation, or powder. The compositions can be formulated as a suppository, with traditional binders and carriers such as triglycerides. Oral formulations can include standard carriers such as pharmaceutical grades of mannitol, lactose, starch, magnesium stearate, sodium saccharine, cellulose, magnesium carbonate, etc. Various delivery systems are known and can be used to administer a composition of the invention, e.g. encapsulation in liposomes, microparticles, microcapsules, and the like.

Formulations for parenteral administration may include aqueous solutions, syrups, aqueous or oil suspensions and emulsions with edible oil such as cottonseed oil, coconut oil or peanut oil. Dispersing or suspending agents that can be used for aqueous suspensions include synthetic or natural gums, such as tragacanth, alginate, acacia, dextran, sodium carboxymethylcellulose, gelatin, methylcellulose, and polyvinylpyrrolidone.

Compositions for parenteral administration may include sterile aqueous or non-aqueous solvents, such as water, isotonic saline, isotonic glucose solution, buffer solution, or other solvents conveniently used for parenteral administration of therapeutically active agents. A composition intended for parenteral administration may also include conventional additives such as stabilizers, buffers, or preservatives, e.g. antioxidants such as methylhydroxybenzoate or similar additives.

Compositions of the invention can be formulated as pharmaceutically acceptable salts as described herein.

A composition of the invention may be sterilized by, for example, filtration through a bacteria retaining filter, addition of sterilizing agents to the composition, irradiation of the composition, or heating the composition. Alternatively, the compounds or compositions of the present invention may be provided as sterile solid preparations e.g. lyophilized powder, which are readily dissolved in sterile solvent immediately prior to use.

After pharmaceutical compositions have been prepared, they can be placed in an appropriate container and labeled for treatment of an indicated condition. For administration of a composition of the invention, such labeling would include amount, frequency, and method of administration.

The invention also provides a pharmaceutical pack or kit comprising one or more containers filled with one or more of the ingredients of a pharmaceutical composition of the invention to provide a beneficial effect, in particular a sustained beneficial effect. Associated with such container(s) can be various written materials such as instructions for use, or a notice in the form prescribed by a governmental agency regulating the labeling, manufacture, use or sale of pharmaceuticals or biological products, which notice reflects approval by the agency of manufacture, use, or sale for human administration.

The invention also provides a kit comprising a compound or a pharmaceutical composition of the invention. The kit can be a package which houses a container which contains a composition of the invention and also houses instructions for administering the composition to a subject.

Applications

The invention contemplates the use of compounds of the Formula I and compositions comprising the same for treating a disease disclosed herein, in particular preventing, and/or ameliorating disease severity, disease symptoms, and/or periodicity of recurrence of a disease disclosed herein. The invention also contemplates treating in mammals, diseases using the compounds, compositions or treatments of the invention. The present invention in embodiments may provide a composition comprising a compound that provides beneficial effects including greater solubility, stability, efficacy, potency, and/or utility, in particular greater solubility and stability.

Novel compounds and methods for new therapeutic interventions are needed for many areas of medicine and disease treatment. For example, chronic and acute inflammatory conditions form the basis for diseases affecting all organ systems including, but not limited to, asthma, acute inflammatory diseases, vascular inflammatory disease, chronic inflammation, atherosclerosis, angiopathy, myocarditis, nephritis, Crohn's disease, arthritis, type I and II diabetes and associated vascular pathologies. The incidence of these inflammatory conditions is on the rise and the expense is large. For example, for just one form of inflammatory disease, Alzheimer's disease, the direct costs (such as medications, doctors' fees, and nursing home care) and indirect costs (loss of productivity of those suffering Alzheimer's disease and loss of productivity of those caring for these individuals) are estimated to exceed one-hundred billion dollars per year.

With reference to the following examples and related discussions, the present invention provides various methods relating to the modulation of inflammation, glial activation or phosphorylation pathways and/or new therapeutic routes relating thereto. As illustrated more fully elsewhere herein, such methods include but are not limited to use of the compounds and compositions of this invention, preferably in a dose dependent fashion, to selectively inhibit protein kinase activity, glial activation response, oxidative stress-related responses such as nitric oxide synthase production and nitric oxide accumulation, cellular apoptosis and/or death associated protein kinase activity, and/or proinflammatory cytokine responses such as interleukin or tumor necrosis factor production. Such methods can include the preparation and/or formulation of a composition with subsequent administration and/or delivery to activated glial cells, tissue, culture or a related physiological system or medium, such administration/delivery in a dose or at a compositional concentration sufficient to effect the desired regulation and/or inhibition, without substantially inhibiting other desired endogenous anti-inflammatory response.

In an aspect, the present invention relates to the inhibition of neuronal cell death. Selective neuronal cell death is a characteristic feature of the pathology of a number of neurodegenerative diseases, including Alzheimer's disease (AD), and traumatic brain injury, and stroke. Selected compounds and compositions of the present invention may be used to reduce or inhibit Aβ-induced neuronal cell death and in particular to reduce or inhibit calmodulin regulated protein kinases, such as death associated protein kinase (DAPK).

In some embodiments, the present invention provides methods of inhibiting cell signaling molecule production (e.g., IL-1β and TNFα), comprising administering compositions comprising one or more of the compounds of the Formula I, in particular one or more compounds depicted in the Figures and Tables herein, in particular the compounds depicted in Table 4, or derivatives of these compounds.

The present invention also provides compounds (e.g., compounds listed in the Figures and Tables for use in 1) lowering amounts of pro-inflammatory cytokines (e.g., TNFα or IL-1p) and/or 2) maintaining normal levels or preventing reduction of presynaptic proteins (e.g. synaptophysin) and/or postsynaptic proteins (e.g., PSD-95). In some embodiments, the reduction of pro-inflammatory cytokines is to levels found in a normal, healthy individual. In some embodiments, the compounds are provided to an individual displaying characteristics of an inflammatory disease (e.g., Alzheimer's disease), such that treatment with the compounds reduces aberrantly high pro-inflammatory cytokine production caused by the disease (e.g., Aβ-induced increase in pro-inflammatory cytokines).

In another aspect, selected compounds and compositions of the invention may be used to modulate cytokine-mediated neuronal cell death, in particular modulate cytokine-induced generation of NO, TNFα signaling through the Fas/TNFR family of death receptors, and/or DAPK, in Alzheimer's disease and other neurodegenerative disorders, and brain injury, and stroke. The evidence for the involvement of pro-inflammatory cytokines and NO in neuronal cell death has been reviewed in Akiyama, H., et al., (2000) Neurobiol. Agri g 21, 383-421; Prusiner, S. B. (2001) New Engl. J. Med. 344, 1516-1526). cytokine-induced neuronal death could involve DAPK.

In part, the present invention also relates to the inhibition of cell death or tissue loss and cell activation in addition to brain glia and neurons. For example, cell activation and tissue damage is a characteristic of other diseases such as acute lung injury (ALI). ALI due to sepsis, trauma or mechanical ventilation is associated with high mortality and morbidity, yet there are few effective therapies for the treatment of ALI. ALI is common during sepsis, which itself has an annual mortality equal to acute myocardial infarction. Endothelial cell (EC) dysfunction and activation has been implicated in the in vivo responses linked to ALI, and EC protein kinases, such as myosin light chain kinase (MLCK), have been shown to be critical to EC barrier function and activation. Similarly, the response of the heart to stress and acute injury results in acute and chronic injuries in which protein phosphorylation regulated pathways and cell activation has been linked to cell death and tissue damage. MLCK and related enzymes such as Rho kinase have been implicated in these processes and may be targets for new therapeutics. Accordingly, compounds of the Formula I can be used to reduce injury from hypoxia-ischemia, acute lung injury and/or endothelial cell dysfunction in lung or vascular tissue.

In another aspect of the invention, a method is provided for treating in a subject a disease involving or characterized by inflammation, in particular neuroinflammation, comprising administering to the subject a therapeutically effective amount of a compound of the Formula I, or a pharmaceutically acceptable salt thereof. In a further aspect, a method is provided for treating in a subject a condition involving inflammation, in particular neuroflammation, comprising administering to the subject a therapeutically effective amount of a composition comprising a compound of the Formula I and a pharmaceutically acceptable carrier, excipient, or vehicle.

In a still further aspect, the invention provides a method involving administering to a subject a therapeutic compound of the formula I, or a pharmaceutically acceptable salt thereof, or a composition comprising a compound of the formula I, and a pharmaceutically acceptable carrier, excipient, or vehicle which inhibit or reduce neuroflammation, activation of glia, proimflammatory cytokines, oxidative stress-related enzymes, acute phase proteins and/or components of the complement cascade.

In another aspect, the invention provides a method for treating in a subject a disease associated with neuroinflammation that can be decreased or inhibited with a compound disclosed herein comprising administering to the subject a therapeutically effective amount of a compound of the formula I, a pharmaceutically acceptable salt thereof, or a composition comprising a compound of the formula I and a pharmaceutically acceptable carrier, excipient, or vehicle.

In another aspect, the invention provides a method for preventing or inhibiting activation of protein kinases, in particular DAPK, in a subject comprising administering a therapeutically effective amount of a compound of the formula I a pharmaceutically acceptable salt thereof, or a composition comprising a compound of the formula I and a pharmaceutically acceptable carrier, excipient, or vehicle.

In a further aspect, the invention provides a method for reducing or inhibiting kinase activity, glial activation, neuronal cell damage, and/or neuronal cell death in a subject comprising administering to the subject a therapeutically effective amount of a compound of the formula I a pharmaceutically acceptable salt thereof, or a composition comprising a compound of the formula I and a pharmaceutically acceptable carrier, excipient, or vehicle.

In some embodiments, the invention provides methods of inhibiting cell signaling molecule production (e.g., IL-1β and TNFα), comprising administering compositions comprising one or more compounds of the Formula I, in particular the compounds depicted in the Figures and Tables 3 and 4, or derivatives of these compounds. In some embodiments, one or more of the compounds, in particular the compounds depicted in the Figures and Tables 3 and 4, or derivatives of these compounds, are co-administered with other recognized therapeutics to treat inflammatory disease (e.g., neuroinflammatory disease, in particular Alzheimer's disease). In some embodiments, the invention provides compounds (e.g., compounds depicted in the Figures and Tables 3 and 4) for use in 1) lowering amounts of pro-inflammatory cytokines (e.g., TNFα or IL-1β) and/or 2) maintaining normal levels of presynaptic proteins (e.g., synaptophysin) or postsynaptic proteins (e.g., PSD-95) for research, drug screening, or therapeutic purposes. In some embodiments, the reduction of pro-inflammatory cytokines reduces cytokines to levels found in a normal, healthy individual. In some embodiments, the compounds are provided to an individual displaying characteristics of an inflammatory disease (e.g., neuroinflammatory disease, in particular Alzheimer's disease), such that treatment with the compounds reduces aberrantly high pro-inflammatory cytokine production caused by the disease (e.g., Aβ-induced increase in pro-inflammatory cytokines).

In an aspect, the invention provides a method for ameliorating progression of a disease or obtaining a less severe stage of a disease in a subject suffering from such disease (e.g., neuroinflammatory disease, in particular a neurodegenerative disease, more particularly Alzheimer's disease) comprising administering a therapeutically effective amount of a compound of the Formula I, a pharmaceutically acceptable salt thereof, or a composition comprising a compound of the Formula I and a pharmaceutically acceptable carrier, excipient, or vehicle.

The invention relates to a method of delaying the progression of a disease (e.g. neuroinflammatory disease, in particular a neurodegenerative disease, more particularly Alzheimer's disease) comprising administering a therapeutically effective amount of a compound of the Formula I, a pharmaceutically acceptable salt thereof, or a composition comprising a compound of the Formula I and a pharmaceutically acceptable carrier, excipient, or vehicle.

The invention also relates to a method of increasing survival of a subject suffering from a disease (e.g. neuroinflammatory disease, in particular a neurodegenerative disease, more particularly Alzheimer's disease) comprising administering a therapeutically effective amount of a compound of the Formula I, a pharmaceutically acceptable salt thereof, or a composition comprising a compound of the Formula I and a pharmaceutically acceptable carrier, excipient, or vehicle.

The invention has particular applications in treating or preventing a neurodegenerative disease, in particular Alzheimer's disease. In an aspect of the invention a compound of the Formula I is utilized in the treatment of Alzheimer's disease. Alzheimer's disease may be treated by administering a therapeutically effective amount of a compound of the Formula I. Such treatment may be effective for retarding the degenerative effects of Alzheimer's disease, including specifically, but not exclusively, neuroinflammation, deterioration of the central nervous system, loss of mental facilities, loss of short term memory, and disorientation.

In another aspect, the invention provides a method for treating Alzheimer's disease by providing a composition comprising a compound of the invention in an amount sufficient to reverse or inhibit neuroinflammation, activation of signaling pathways involved in inflammation (e.g., neuroinflammation), cell signaling molecule production, activation of glia or glial activation pathways and responses, proinflammatory cytokines or chemokines (e.g., interleukin (IL) or tumor necrosis factor (TNF), oxidative stress-related responses such as nitric oxide synthase production and nitric oxide accumulation, acute phase proteins, components of the complement cascade, protein kinase activity (e.g., death associated protein kinase activity), neuronal cell damage, and/or neuronal cell death for a prolonged period following administration.

In a further aspect, the invention provides a method for treating Alzheimer's disease in a patient in need thereof which includes administering to the individual a composition that provides a compound of the invention in a dose sufficient to reverse or inhibit neuroinflammation, activation of signaling pathways involved in inflammation (e.g., neuroinflammation), cell signaling molecule production, activation of glia or glial activation pathways and responses, proinflammatory cytokines or chemokines (e.g., interleukin (IL) or tumor necrosis factor (TNF), oxidative stress-related responses such as nitric oxide synthase production and nitric oxide accumulation, acute phase proteins, components of the complement cascade, protein kinase activity (e.g., death associated protein kinase activity), neuronal cell damage, and/or neuronal cell death for a prolonged period following administration.

The invention in an embodiment provides a method for treating Alzheimer's disease, the method comprising administering to a mammal in need thereof a composition comprising a compound of the invention in an amount sufficient to reduce cognitive decline for a prolonged period following administration, thereby treating the Alzheimer's disease.

In as aspect, the invention relates to a method of treatment comprising administering a therapeutically effective amount of one or more compound of the Formula I, a pharmaceutically acceptable salt thereof, or a composition comprising a compound of the Formula I and a pharmaceutically acceptable carrier, excipient, or vehicle, which upon administration to a subject with symptoms of a neurodegenerative disease, in particular Alzheimer's disease, produces one or more therapeutic effect, in particular a beneficial effect, more particularly a sustained beneficial effect. In an embodiment, a beneficial effect is evidenced by a decrease or inhibition of one or more of the following: inflammation (e.g. neuroinflammation), activation of signaling pathways involved in inflammation (e.g., neuroinflammation), cell signaling molecule production, activation of glia or glial activation pathways and responses, proinflammatory cytokines or chemokines (e.g., interleukin (IL) or tumor necrosis factor (TNF), oxidative stress-related responses such as nitric oxide synthase production and nitric oxide accumulation, acute phase proteins, components of the complement cascade, protein kinase activity (e.g., death associated protein kinase activity), cell damage (e.g., neuronal cell damage), and/or cell death (e.g., neuronal cell death).

In an embodiment, where the disease is Alzheimer's disease, beneficial effects of a compound or composition or treatment of the invention can manifest as one, two, three, four, five, six, seven, eight, or all of the following, in particular five or more, more particularly 7 or more of the following:

a) A reduction in protein kinase activity (e.g. DAPK), in particular at least about a 0.05%, 0.1%, 0.5%, 1%, 2%, 5%, 10%, 15%, 20%, 30%, 33%, 35%, 40%, 45%, 50%, 60%, 70%, 80%, 90%, 95%, or 99% decrease in protein kinase activity.

b) A reduction in glial activation response, in particular, at least about a 0.05%, 0.1%, 0.5%, 1%, 2%, 5%, 10%, 15%, 20%, 30%, 33%, 35%, 40%, 45%, 50%, 60%, 70%, 80%, 90%, 95%, or 99% reduction in glial activation.

c) A reduction in glial activity in the brain, relative to the levels determined in the absence of a compound of the Formula I in subjects with symptoms of Alzheimer's disease. In particular, the compounds induce at least about a 2%, 5%, 10%, 15%, 20%, 30%, 40%, 50%, 60%, 70%, 80%, or 90% decrease in glial activity d) A reduction in oxidative stress-related responses (e.g., nitric oxide synthase production and/or nitric oxide accumulation), in particular at least about a 0.05%, 0.1%, 0.5%, 1%, 2%, 5%, 10%, 15%, 20%, 30%, 33%, 35%, 40%, 45%, 50%, 60%, 70%, 80%, 90%, 95%, or 99% reduction in oxidative stress-related responses such as nitric oxide synthase production and nitric oxide accumulation.

e) A reduction in cellular apoptosis and/or death associated protein kinase activity, in particular a 0.05%, 0.1%, 0.5%, 1%, 2%, 5%, 10%, 15%, 20%, 30%, 33%, 35%, 40%, 45%, 50%, 60%, 70%, 80%, 90%, 95%, or 99% reduction in cellular apoptosis and/or death associated protein kinase activity.

f) A reduction in proinflammatory cytokine responses in particular a 0.05%, 0.1%, 0.5%, 1%, 2%, 5%, 10%, 15%, 20%, 30%, 33%, 35%, 40%, 45%, 50%, 60%, 70%, 80%, 90%, 95%, or 99% reduction in proinflammatory cytokine responses.

g) A reduction in interleukin-1β and/or tumor necrosis factorα production in particular a 0.05%, 0.1%, 0.5%, 1%, 2%, 5%, 10%, 15%, 20%, 30%, 33%, 35%, 40%, 45%, 50%, 60%, 70%, 80%, 90%, 95%, or 99% reduction in interleukin-1β and/or tumor necrosis factorα production.

h) Preventing loss of presynaptic proteins (e.g., synaptophysin) and/or postsynaptic proteins.

i) A slowing of the rate of disease progression in a subject with Alzheimer's disease.

j) Increase in survival in a subject with symptoms of Alzheimer's disease.

In particular aspects of the invention beneficial effects of compounds, compositions or treatments of the invention can manifest as (a) and (b); (a), (b) and (c); (a) through (d); (a) through (e); (a) through (f); (a) through (g); (a) through (h); (a) through (i), or (a) through (j).

Compounds, pharmaceutical compositions and methods of the invention can be selected that have sustained beneficial effects. In an embodiment, a pharmaceutical composition with statistically significant sustained beneficial effects is provided comprising a therapeutically effective amount of a compound of the invention.

The invention provides a method for treating mild cognitive impairment (MCI) comprising administering a therapeutically effective amount of a compound of the Formula I, a pharmaceutically acceptable salt thereof, or a composition comprising a compound of the Formula I and a pharmaceutically acceptable carrier, excipient, or vehicle.

In an embodiment, the invention provides a method of reversing or inhibiting neuroinflammation, activation of signaling pathways involved in inflammation (e.g., neuroinflammation), cell signaling molecule production, activation of glia or glial activation pathways and responses, proinflammatory cytokines or chemokines (e.g., interleukin (IL) or tumor necrosis factor (TNF), oxidative stress-related responses such as nitric oxide synthase production and nitric oxide accumulation, acute phase proteins, components of the complement cascade, protein kinase activity (e.g., death associated protein kinase activity), neuronal cell damage, and/or neuronal cell death, after the onset of cognitive deficits and Alzheimer's disease neuropathology in a subject comprising administering to the subject a therapeutically effective amount of a compound of the Formula I, a pharmaceutically acceptable salt thereof, or a composition comprising a compound of the Formula I and a pharmaceutically acceptable carrier, excipient, or vehicle.

The invention provides a method of preventing a disease disclosed herein in a subject with a genetic predisposition to such disease by administering an effective amount of a compound of the Formula I, or a pharmaceutically acceptable salt thereof, or a composition comprising a compound of the Formula I and a pharmaceutically acceptable carrier, excipient, or vehicle.

The invention provides a method of improving memory of a healthy subject or the memory of a subject with age impaired memory by administering an effective amount of a compound of the Formula I, or a pharmaceutically acceptable salt thereof, or a composition comprising a compound of the Formula I and a pharmaceutically acceptable carrier, excipient, or vehicle.

The further provides to a method for improving memory, especially short-term memory and other mental dysfunction associated with the aging process comprising administering an effective amount of a compound of the Formula I, or a pharmaceutically acceptable salt thereof, or a composition comprising a compound of the Formula I and a pharmaceutically acceptable carrier, excipient, or vehicle.

In an embodiment, a method is provided for treating a mammal in need of improved memory, wherein the mammal has no diagnosed disease, disorder, infirmity or ailment known to impair or otherwise diminish memory, comprising the step of administering to the mammal an effective memory-improving amount of a compound of the Formula I, a pharmaceutically acceptable salt thereof, or a composition comprising a compound of the Formula I and a pharmaceutically acceptable carrier, excipient, or vehicle.

In an aspect, the invention relates to a method of improving the lifespan of a subject suffering from Alzheimer's disease comprising administering a therapeutically effective amount of a compound of the Formula I, a pharmaceutically acceptable salt thereof, or a composition comprising a compound of the Formula I and a pharmaceutically acceptable carrier, excipient, or vehicle.

In some aspects, greater efficacy and potency of a treatment of the invention may improve the therapeutic ratio of treatment, reducing untoward side effects and toxicity. Selected methods of the invention may also improve long-standing disease even when treatment is begun long after the appearance of symptoms.

The compositions and methods described herein are indicated as therapeutic agents or methods either alone or in conjunction with other therapeutic agents or other forms of treatment. They may be combined or formulated with one or more therapies or agents used to treat a condition described herein. Compositions of the invention may be administered concurrently, separately, or sequentially with other therapeutic agents or therapies. Therefore, the compounds of the Formula I may be co-administered with one or more additional therapeutic agents including without limitation beta-secretase inhibitors, alpha-secretase inhibitors, and epsilon-secretase inhibitors, agents that are used for the treatment of complications resulting from or associated with a disease, or general medications that treat or prevent side effects.

The invention also contemplates the use of a composition comprising at least one compound of the invention for the preparation of a medicament in treating a disease disclosed herein. In an embodiment, the invention relates to the use of a therapeutically effective amount of at least one compound of the invention for preparation of a medicament for providing therapeutic effects, in particular beneficial effects, more particularly sustained beneficial effects, in treating a disorder or disease. In a still further embodiment the invention provides the use of a compound of the invention for the preparation of a medicament for prolonged or sustained treatment of a disease.

Administration

Compounds and compositions of the present invention can be administered by any means that produce contact of the active agent(s) with the agent's sites of action in the body of a subject or patient to produce a therapeutic effect, in particular a beneficial effect, in particular a sustained beneficial effect. The active ingredients can be administered simultaneously or sequentially and in any order at different points in time to provide the desired beneficial effects. A compound and composition of the invention can be formulated for sustained release, for delivery locally or systemically. It lies within the capability of a skilled physician or veterinarian to select a form and route of administration that optimizes the effects of the compositions and treatments of the present invention to provide therapeutic effects, in particular beneficial effects, more particularly sustained beneficial effects.

The compositions may be administered in oral dosage forms such as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular forms, all utilizing dosage forms well known to those of ordinary skill in the pharmaceutical arts. The compositions of the invention may be administered by intranasal route via topical use of suitable intranasal vehicles, or via a transdermal route, for example using conventional transdermal skin patches. A dosage protocol for administration using a transdermal delivery system may be continuous rather than intermittent throughout the dosage regimen. A sustained release formulation can also be used for the therapeutic agents.

An amount of a therapeutic of the invention which will be effective in the treatment of a particular disorder or disease to provide effects, in particular beneficial effects, more particularly sustained beneficial effects, will depend on the nature of the condition or disorder, and can be determined by standard clinical techniques. The precise dose to be employed in the formulation will also depend on the route of administration, and the seriousness of the disease, and should be decided according to the judgement of the practitioner and each patient's circumstances.

Thus, the dosage regimen of the invention will vary depending upon known factors such as the pharmacodynamic characteristics of the agents and their mode and route of administration; the species, age, sex, health, medical condition, and weight of the patient, the nature and extent of the symptoms, the kind of concurrent treatment, the frequency of treatment, the route of administration, the renal and hepatic function of the patient, and the desired effect.

Suitable dosage ranges for administration are particularly selected to provide therapeutic effects, in particular beneficial effects, more particularly sustained beneficial effects. A dosage range is generally effective for triggering the desired biological responses. The dosage ranges are generally about 0.5 mg to about 2 g per kg, about 1 mg to about 1 g per kg, about 1 mg to about 200 mg per kg, about 1 mg to about 100 mg per kg, about 1 mg to about 50 mg per kg, about 10 mg to about 100 mg per kg, or about 30 mg to 70 mg per kg of the weight of a subject.

A composition or treatment of the invention may comprise a unit dosage of at least one compound of the invention to provide beneficial effects. A "unit dosage" or "dosage unit" refers to a unitary i.e. a single dose which is capable of being administered to a patient, and which may be readily handled and packed, remaining as a physically and chemically stable unit dose comprising either the active agents as such or a mixture with one or more solid or liquid pharmaceutical excipients, carriers, or vehicles.

A subject may be treated with a compound of the Formula I or composition or formulation thereof on substantially any desired schedule. A composition of the invention may be administered one or more times per day, in particular 1 or 2 times per day, once per week, once a month or continuously. However, a subject may be treated less frequently, such as every other day or once a week, or more frequently. A compound, composition or formulation of the invention may be administered to a subject for about or at least about 1 week, 2 weeks to 4 weeks, 2 weeks to 6 weeks, 2 weeks to 8 weeks, 2 weeks to 10 weeks, 2 weeks to 12 weeks, 2 weeks to 14 weeks, 2 weeks to 16 weeks, 2 weeks to 6 months, 2 weeks to 12 months, 2 weeks to 18 months, or 2 weeks to 24 months, periodically or continuously.

The invention will be described in greater detail by way of specific examples. The following examples are offered for illustrative purposes, and are not intended to limit the invention in any manner.

EXAMPLES

Example 1

General Materials and Methods

Synthetic Chemistry. All reagents and solvents were used as purchased without further purification. Syntheses were done using variations of established methods and in-parallel synthetic schemes. Removal of solvent was followed by recrystallization from 95% ethanol. Reactions were monitored by analytical HPLC (Rainin Instruments System Woburn, Mass.), done on a reverse phase column CIS (25 cm×4.6 mm, 5 um, Supelco, Bellefonte, Pa.) with two different UV wavelengths (X=260 nm and X=220 nm or 300 nm). Eluents were (A): 0.1% (v/v) TFA in water and (B) 80% (v/v) acetonitrile/water containing 0.08% TFA. A linear gradient of 100/0 to 0/100 A/B over 34 min at 1mL/min was used. 1H-NMR spectra were obtained using Varian INOVA (500 MHz) spectrometer. High resolution mass spectra were obtained on a VG70-250SE mass spectrometer.

Cell Culture Assays. BV-2 mouse microglial cells (5×10³ cells/well in a 48-well plate) were cultured and treated for 16 hrs with the standard glial activating stimulus lipopolysaccharide (LPS, from *Salmonella typhimurium;* 100 ng/ml final concentration) in the presence or absence of aminopyridazine compounds, as described previously [4,17]. EL-1/3 and TNFa levels in cell lysates were determined by electrochemiluminescent detection in a Meso-Scale Discovery (MSD) kit, as per the manufacturer's instructions.

In vivo Assays. Aβ-42 infusions and treatment of C57B1/6 mice with MW01-2-151WH were performed as previously described [5]. Briefly, oligomeric A/31-42 was infused ICV for 28 days with a micro-osmotic pump. At post-operative day 21 and continuing for 14 days thereafter, mice were injected intraperitoneally once daily with either MW01-2-151WH (2.5 mg/kg per day) or solvent control (10% DMSO in saline). At post-operative day 60, mice were perfused and sacrificed, and hippocampal endpoints measured as previously described [5]. Endpoint assays included immunohistochemical detection of activated astrocytes and microglia by glial fibrillary acidic protein (GFAP) and F4/80 staining, measurement of the levels of the pro-inflammatory cytokines IL-1lS, TNFa, and S100B by ELISA, and determination of synaptic damage by analysis of the levels of postsynaptic density protein-95 (PSD-95).

Brain Uptake Assays. MW01-2-151WH was administered to mice (25-30 g) by oral gavage using 2.5 mg/kg compound in 0.5% carboxymethylcellulose vehicle. At various times (0-60 min) after administration, mice were sacrificed, blood removed by cardiac puncture, and brains immediately harvested, weighed, quick-frozen in liquid nitrogen, and stored at −80° C. until assayed. Brain tissue was homogenized in 1.5 ml of 0.1 M perchloric acid. After centrifugation (12,000×g for 10 min), the supernatant was neutralized with 1 M NaOH and then extracted three times with 2 ml of dichloromethane by centrifugation at 3,000×g for 5 min. The organic phases from the three successive extractions were pooled and then vaporated to dryness under reduced pressure. The dried sample was reconstituted in 100 μl of HPLC mobile phase (80% acetonitrile, 0.08% formic acid, 20% $H_2O$), and 20 μl of the reconstituted material was injected into the HPLC system. The HPLC system for detection of MWO1-2-151WH was a Luna 5 μmCIS, 250 mm×2 mm internal diameter column together with a guard column (Phenomenex, Torrance, Calif., USA), with HPLC solvent delivered at 0.2 ml/min (Dionex, model P680 pump) and absorbance monitored at 282 run (Dionex, model UVD 170U detector). Under these experimental conditions, the retention time of the MW01-2-151WH compound was 15.3 min. A standard curve of MWO 1-2-151 WH was prepared by adding increasing concentrations of the compound to brain tissue from untreated mice, then extracting the brains and performing HPLC analysis as described above. The area under the curve increased linearly with MW01-2-151WH concentration over the range of concentrations investigated, with a correlation coefficient of 0.99. Under our experimental conditions, the compound was extracted reproducibly, with mean recoveries of 29+/−2%.

Graded dose, acute toxicity assays Vehicle (30% DMSO) or MW01-2-151WH (3.1, 12.5 or 50 mg/kg) in 0.5% carboxymethylcellulose was administered by oral gavage once daily for 3 days. On the 4th day, mice were anesthetized with pentobarbital, intubated and the lungs were inflated with an air containing syringe. The mice were perfused through the right ventricle and the lungs, liver and kidneys were then harvested and fixed in 4% paraformaldehyde for histology. Paraffin embedded hematoxylin & eosin stained sections of each organ were prepared by standard techniques. A pathologist blinded to the treatment groups performed microscopic assessment of the tissue for injury.

Figure 2:
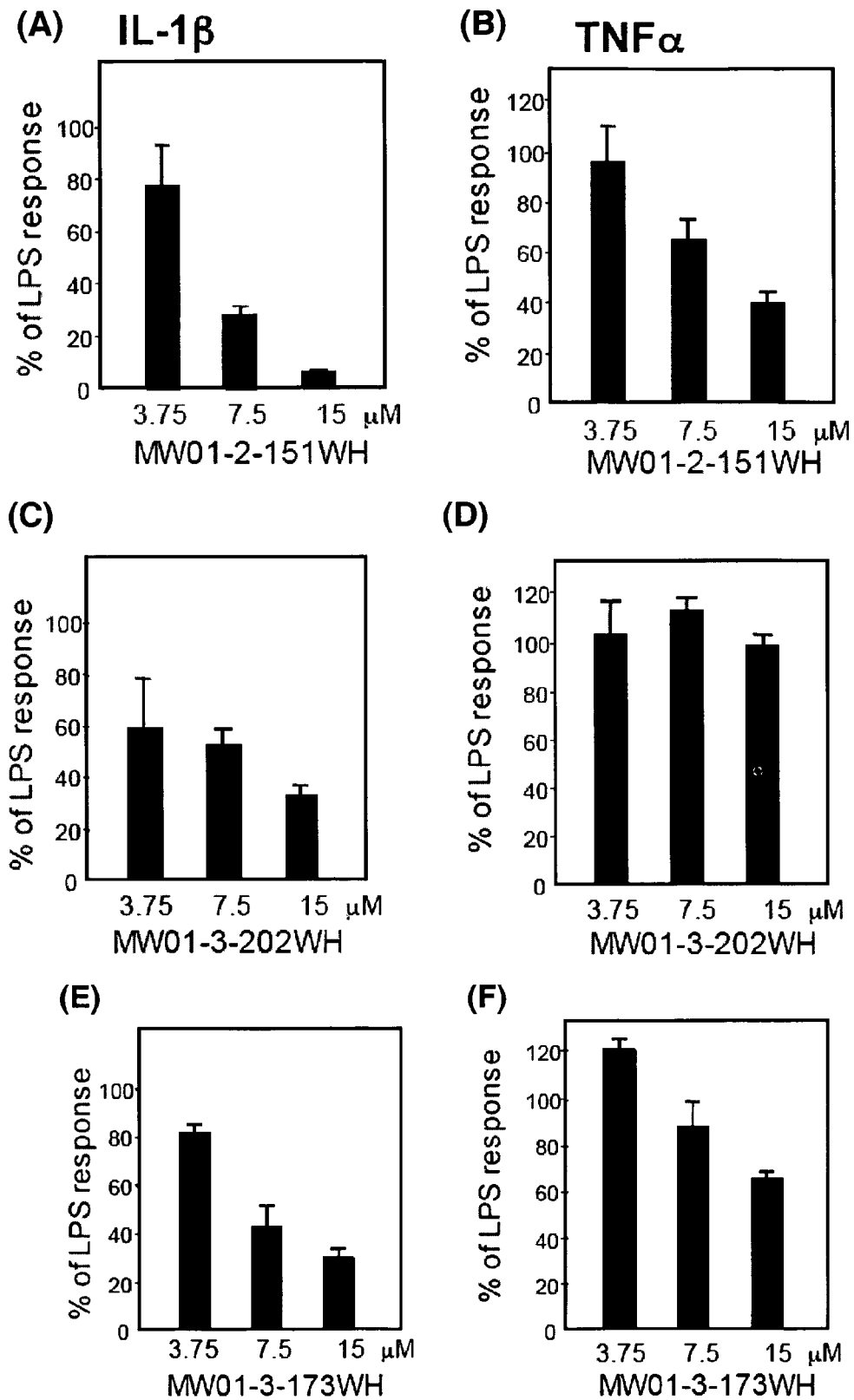
FIGS. 2A-C are graphs of concentration dependent inhibition of proinflammatory cytokine production by MW01-2-151WH and related compounds. BV-2 cells were treated with LPS (100 ng/ml) in the absence or presence of increasing concentrations of MW01-2-151WH or three structurally related analogs (MW01-3-202WH and MW01-3-173WH) for 16 hrs with levels of IL-1β and TNFα in cell lysates measured by the Meso-Scale Discovery electrochemiluminescent detection assay (See, e.g., Example 1, Materials and Methods). Data are the mean+/−SEM of triplicate determinations.

MW01-2-151 WH suppressed both IL-1β and TNFα production in a concentration dependent manner, whereas the closely related analogs MW01-3-202WH and MW01-3-173WH showed somewhat less suppressive activity (See, e.g., FIG. 2).

Figure 3:
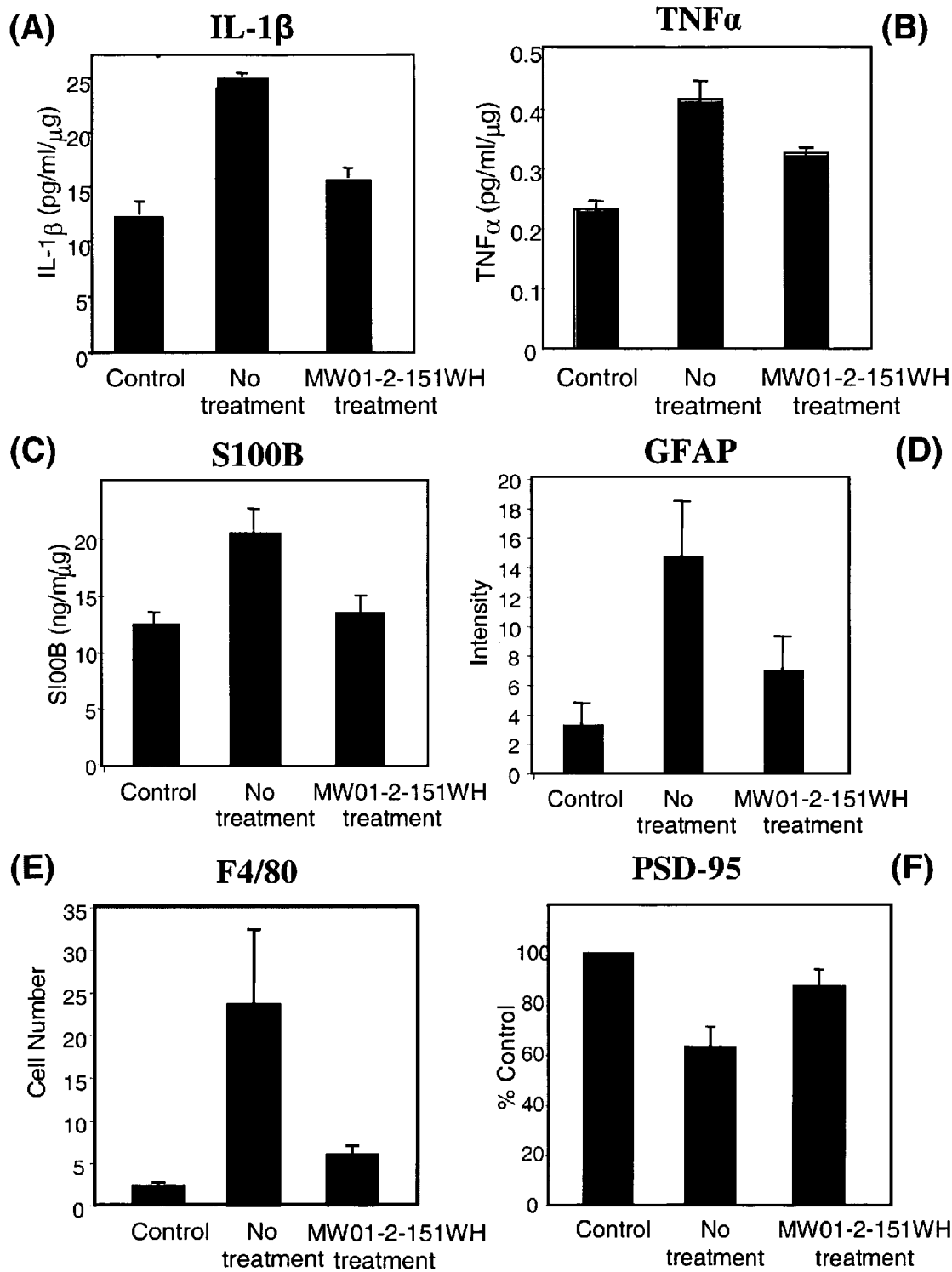
FIG. 3A-F are graphs of MW01-2-151WH suppression of Aβ-induced neuroinflammation and synaptic damage. Hippocampal sections or extracts from vehicle-infused mice (control), Aβ-infused mice injected with solvent, and Aβ-infused mice injected with MW01-2-151 WH were evaluated for neuroinflammation by measurement of the levels of the pro-inflammatory cytokines IL-1β (A), TNFα(B), and S100B (C), and the number of GFAP-positive astrocytes, (D) and F4/80-positive microglia, (E), and evaluated for synaptic damage by analysis of the levels of the postsynaptic density protein 95 (PSD-95) (F). Data are from one of two independent experiments, and are the mean±SEM for 4-5 mice per experimental group.
Figure 4:
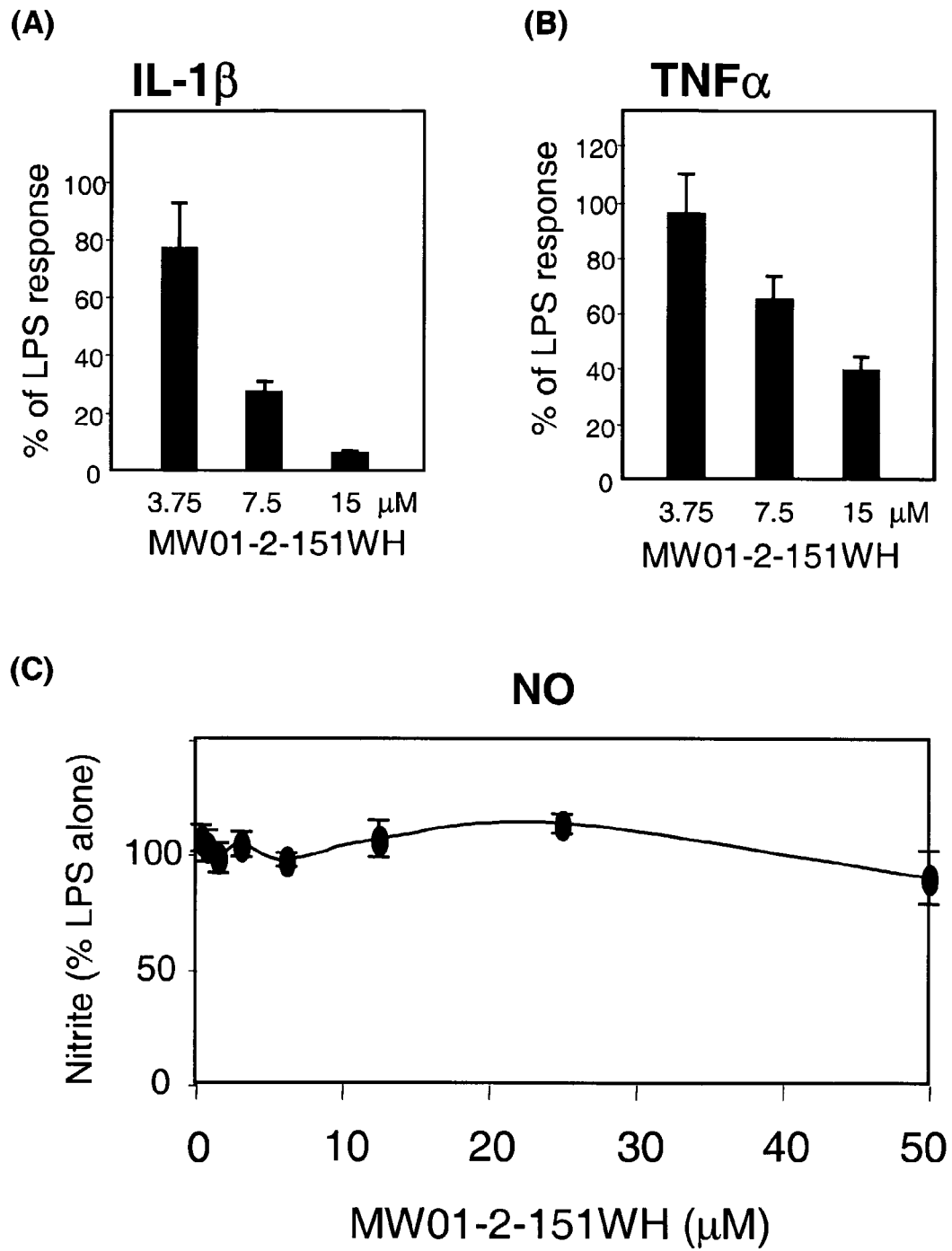
FIG. 4 A-C are graphs of the cell-based activity of MW01-2-151WH in BV-2 microglial cells. MW01-2-151WH is a concentration-dependent and selective inhibitor of proinflammatory cytokine production by activated glia. Concentration-dependent inhibition by MW01-2-151WH of LPS-induced increases in (A) IL-1β and (B) TNFα levels by the BV2 microglial cell line. (C) Accumulation of the NO metabolite, nitrite, was not inhibited at concentrations up to 50 μM.

Based on the concentration-dependent suppression of neuroinflammation in the cell-based assay, MW01-2-151 WH was tested in a recently developed animal model [5,6]. Mice infused ICV with Aβ-42 and administered MW01-2-151 WH peripherally (intraperitoneal injection) showed significant inhibition of Aβ-induced neuroinflammation in the hippocampus (See, e.g., FIG. 3). MW01-2-151 WH treatment blocked the Aβ-induced increase in the pro-inflammatory cytokines IL-1β, TNFα, and S100B, and suppressed a number of activated GFAP-positive astrocytes and F4/80 positive microglia (See, e.g., FIG. 3). MW01-2-151WH treatment also showed some neuroprotection, in that it partially prevented the Aβ-induced reduction of the postsynaptic protein, PSD-95 (See, e.g., FIG. 3).

Figure 5:
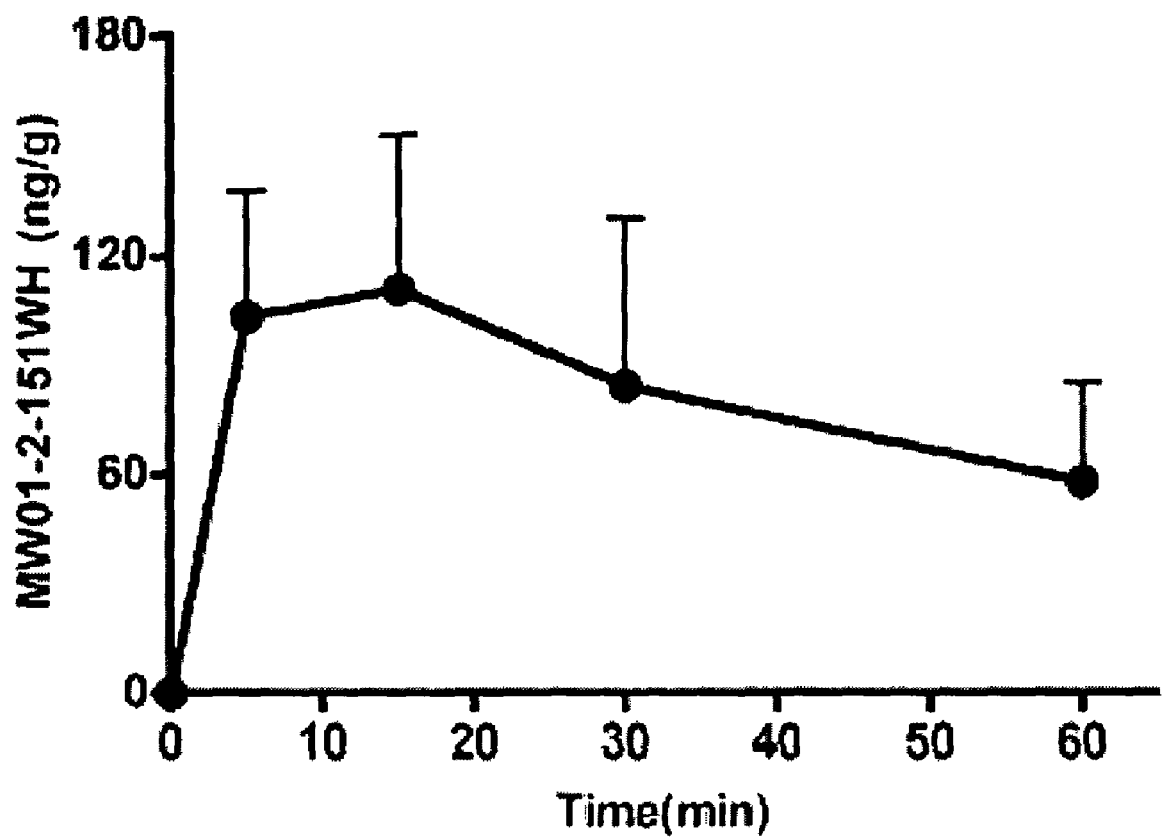
FIG. 5 is a graph of rapid brain uptake of an orally administered, therapeutic dose of MW01-2-20 151WH. Oral gavage administration of a 2.5 mg/kg dose of MW01-2-151WH to mice was followed by sacrifice, rapid removal of brain, and tissue processing at different times after administration (described in Materials and Methods). Tissue samples were processed by perchloric acid treatment followed by extraction into dichloromethane. Analysis and quantification was done by HPLC, using external calibration by addition of known concentrations of MW01-2-151WH to naive brain homogenates and processing as above. Data are the mean±SEM for four mice.

An important aspect to consider in lead compound development for inflammatory diseases (e.g., Alzheimer's disease) is to address questions of bioavailability and toxicity. Therefore, the ability of MW01-2-151WH to be taken up into brain after oral gavage administration to mice was analyzed. The compound was rapidly detected in brain tissue, reaching a maximum within 5 minutes after administration (See, e.g., FIG. 5). MW01-2-151WH induced tissue toxicity was also examined by testing a series of escalating doses in an acute toxicity paradigm. Three different doses of MW01-2-15WH (3,1, 12.5, or 50 mg/kg) were administered by oral gavage once daily for 3 days, mice were sacrificed on day 4, and liver, lungs, and kidney were analyzed for histological evidence of toxicity. No tissue toxicity was observed, even at the highest dose tested (See, e.g., FIG. 5). The high dose of 50 mg/kg represents a dose 20-fold higher than the therapeutic dose used in FIG. 3. No evidence of tissue toxicity was observed under the chronic administration conditions of the Alzheimer's disease relevant mouse model used for the studies in FIG. 3. Thus, compound MW01-2-151WH is bioavailable and rapidly taken up into brain, and is non-toxic under both acute and chronic conditions of administration.

Table 1 provides examples depicting differences in computed molecular properties between MW01-2-151WH and MW01-070C. MW01-070C, described in U.S. Patent Application No. 20030176437 (herein incorporated by reference in its entirety for all purposes) was developed as a bioavailable inhibitor of glial activation and used for in vivo proof of concept pathway validation studies [2,5,6]. MW01-2-151 WH serves as a minimalist pyridazine derivative from the focused libraries that represent diversifications of the inactive pyridazine fragment. The physical properties of MWOI-2-151WH allow further medicinal chemistry refinement that are contemplated to produce compounds well within the parameters recently identified as characteristic of orally bioavailable and safe drugs [11].

The information herein provided adds to the accumulating body of evidence that documents the benefits of targeting inflammation cycles (e.g, neuroinflammation cycle) in drug discovery (e.g., Alzheimer's disease drug discovery). MW01-2-151WH and related compounds (e.g., see Figures and Tables) provide compounds with desired in vivo effects. Furthermore, these compounds can be developed by the de novo focused library synthesis and iterative screen protocol that starts with a privileged core fragment (See, e.g., FIG. 1, and U.S. Patent Application No. 20030176437). The focused compound libraries of the present invention provide discrete chemical diversifications that generate compounds with desired molecular properties, in vivo efficacy, and promising safety profiles. These minimalist pyridazine structures have in vivo function but are well below the maximal desired molecular weight and are still amenable to further medicinal chemistry refinement in future drug development (e.g., addition of hydrogen, alkyl, substituted alkyl, phenyl, substituted phenyl, arylalkyl, substituted arylalkyl, halogen, amino, heterocyclic, substituted heterocyclic, cycloalkyls, hydroxy, amine, substituted amine, arylamine, heteroarylamine, arylalkylamine, hydrazinyl, substituted hydrazinyl, pyrimidinyl and substituted pyrimidinyl, pyridinyl and substituted pyridinyl, pyrazinyl and substituted pyrazinyl, thienyl and substituted thienyl, thiazolyl and substituted thiazolyl, pyrazolyl and substituted pyrazolyl, stilbenzyl and substituted stilbenzyl, imidazolyl and substituted imidazolyl, phthalazine and substituted phthalazine, piperazinyl and/or substituted piperazinyl moieties).

Example 2

Acute and Chronic Toxicity Assays

Liver toxicity is an especially important initial consideration for orally administered compounds, as the liver is the major site of initial drug metabolism and is critical to overall metabolism and homeostasis of an animal. Liver injury is also a component of idiopathic tissue injury seen in certain chronically administered drugs. Therefore, it is important to do initial assessments of liver toxicity after oral administration of compounds to mice.

A standard approach is to test compounds in two initial in vivo toxicity assays: an acute, escalating-dose paradigm and a chronic, therapeutic dose regimen. For the escalating-dose, acute toxicity assays, mice (5 per experimental group) will be administered either test compound or vehicle in 0.5% carboxymethylcellulose (alternatively, castor oil or sesame oil can be used) by oral gavage once daily for 3 days. Standard test compound doses will be 3.1, 12.5, and 50 mg/kg; the highest dose will be 20× a therapeutic dose. On the 4th day, mice will be sacrificed and the liver harvested and fixed for histology. Paraffin-embedded, hematoxylin & eosin (H&E)-stained sections of liver tissue will be analyzed microscopically for injury by two individuals blinded to the treatment groups. A semi-quantitative histological scoring system from 0 (best) to 9 (worst) will be applied that considers architecture features (normal to extensive fibrosis), cellular features (normal to extensive edema and widespread necrosis), and degree of inflammatory infiltrate (normal to extensive infiltrate). For each acute toxicity assay, 15 mg of compound will be required.

For the therapeutic dose, chronic toxicity assays, mice (5 per experimental group) will be administered either compound or vehicle in 0.5% carboxymethylcellulose by oral gavage once daily for 2 weeks at a therapeutic dose of 2.5 mg/kg/day. After two weeks of treatment, mice will be sacrificed and liver toxicity analyzed as described above. For each chronic toxicity assay, 5 mg of test compound will be required.

Example 3 hERG Channel Inhibition Assays and Cardiac QT Interval Assays

Compounds are screened for hERG (human ether-a-go-go) potassium ion channel binding and inhibition in order to eliminate early in the process any compounds with high potential to induce prolongation of cardiac QT interval in later studies due to off-target toxicities. The hERG channel conducts rapidly activating delayed rectifier potassium currents that critically contribute to cardiac repolarization. Mutations in the hERG channel gene and drug-induced blockade of the currents have been linked to delayed repolarization of action potentials resulting in prolonged QT interval (Finlayson et al., 2004; Recanatini et al., 2005; Roden, 2004). QT prolongation is considered a significant risk factor against cardiac safety of new drugs. Therefore, consideration of cardiac safety early in the development process by testing for hERG channel inhibition provides an efficient and predictive means to assess potential compound cardiac safety liabilities. In addition, the FDA (USA) is considering this as an approval criteria in the future and has specific recommendations at this time. The assays may be conducted using a commercial service (MDS PharmaService).

The initial assay is a radioligand binding assay that tests the ability of the test compound to compete with $^3$H-astemizole (a reference standard that binds to hERG channels with nM affinity) for binding to recombinant hERG channels stably expressed on human HEK-293 cells. This cell line was chosen because it is of human origin, has been fully characterized with regard to hERG electrophysiology and pharmacology and displays the expected characteristics of $I_{Kr}$ current as well as expected pharmacological sensitivities, and is easy to maintain in culture (Zhou et al., 1998). A single concentration (10 µM) of test compound will be assayed, and % inhibition of $^3$H-astemizole binding will be calculated. Generally, any compounds that show >50% inhibition will be tested further in the hERG channel activity assay. This is usual for medium throughput screens but is not recommended in the FDA document and tends to give false positives.

The hERG channel activity inhibition assay provides whole cell electrophysiological data about compound effects on the hERG K$^+$ channel function. Whole cell patch clamp methodology is generally considered to be the gold-standard determination of ion channel activity, rather than simply measuring channel binding. The standard testing procedure will be to use 3 to 5 concentrations of compound at log dilutions with each concentration tested in triplicate (three cells). This allows a balance between achieving a reasonably accurate $IC_{50}$ measurement against a broad concentration range, and reducing cell attrition that would occur during more protracted experiment durations. After completion of compound dose-response procedures, a known hERG channel inhibitor, such as astemizole, will be applied as a positive control.

Compounds which exhibit inhibition of hERG channel activity will be verified as positives (the hERG channel activity assay can give false positives and false negatives) by testing in vivo for prolongation of cardiac QT interval. The QT interval studies will be performed by evaluating compounds for effects on QT interval in Lead II electrocardiograms measured in anesthetized guinea pigs (Hirohashi et al., 1991), one of the species recommended in the FDA white paper. Vehicle or compound will be administered orally at 15 mg/kg (dosing volume of 10 ml/kg) to groups of male guinea pigs (weighing 330-350 g), with 5 animals per group. This dose corresponds approximately to 20-fold the therapeutic dose by taking into account the body surface area of the animals. Heart rate, arterial blood pressure, and QT intervals will be measured at baseline, and at 15, 30, 45, and 60 min after compound administration. Sotalol administered iv at 0.3 mg/kg will serve as the positive control compound. The QT intervals will be corrected for changes in heart rate using both Bazett's and Fridericia's formulae. Any increase in QT interval values over baseline values exceeding the upper 95% confidence limit of the mean changes at the corresponding time point in the vehicle-treated control group for two consecutive observation times indicates significant QT interval prolongation in the individually treated animals. This functional testing in early discovery provides a rapid and cost-effective method to better anticipate and eliminate compounds that may have adverse QT prolongation potential in humans.

Example 4

Preparation of 3-chloro-5,6-dihydrobenzo[h]cinnoline

A common precursor, 3-chloro-5,6-dihydrobenzo[h]cinnoline (7; FIG. 1), was used to make compounds MW01-2-151WH, MW01-3-202WH, and MW01-3-173WH. This key precursor 7 was prepared using a combination of previously reported methods [12-16]. Condensation of glyoxylic acid with the α-tetralone (CAS 529-34-0) 2 gave the unsaturated acid 3, which was reduced to the corresponding saturated acid 4. Cyclization of the intermediate 4 with hydrazine hydrate provided 4,4a,5,6-tetrahydrobenzo[A]cinnolin-3(2H)-one (5) which was dehydrogenated efficiently by anhydrous copper (II) chloride in acetonitrile to give pyridazinone 6. The common chloropyridazine 7 precursor was then obtained by the chlorination of pyriazinone 6 with phosphorus oxychloride. Specifically, a mixture of 5,6-dihydrobenzo[A]cinnolin-3(2H)-one (6, 19.8 g, 0.1 mol) in 100 mL of phosphorus oxychloride was stirred at 95° C. for 2 h. Most of the solvent was removed by distillation under reduced pressure. The residue was then cooled to room temperature, poured onto crushed ice, neutralized with NaOH solution. The precipitation was filtered off and washed with water, dried over filter funnel to give dark green solid. The crude product was decolored by dissolving it in dichloromethane and filtering through a short silica gel column to give a yellow solution. Removal of solvent followed by recrystallization from 95% ethanol gave golden yellow crystals (18.0 g, yield 82.9%). HRMS calculated 216.0449, found 216.0442; 1H NMR (CDCl3): 6 8.529 (dd, J=5.0, J=3.5, 1H), 7.423 (dd, J=5.5, J=3.5, 2H), 7.353 (s, 1H), 7.274 (t, J=3.5, J=5.0, 1H), 2.992 (s, 4H). The final compounds MW01-3-173WH, MW01-3-202WH and MW01-2-151WH were then synthesized by the amination reaction of compound 7 with the corresponding piperazines, as indicated in FIG. 1.

Example 5

Preparation of 5,6-dihydro-3-(4-(pyrimidin-2-yl) piperazin-1-yl)benzo[h]cinnoline (MW01-2-151WH A mixture of comprising about 0.01 mol of 3-chloro-5,6-dihydrobenzo[h]cinnoline, about 0.05 mol of 1-(2-pyrimidyl)piperazine and about 0.01 mol of ammonium hydrochloride was prepared in about 15 ml of 1-BuOH. The mixture was stirred at 130° C. for 48 h, and then the solvent was removed under reduced pressure. The remaining residue was then extracted with ethyl acetate, washed with water and brine, dried over anhydrous $Na_2SO_4$. Removal of solvent followed by recrystallization from 95% ethanol yielded golden yellow crystals, yield 87.0%; HPLC: 96.6% purity; HRMS calculated 344.1744, found 344.1738; 1H NMR (CDCl3): d 8.452 (d, J=7.5, 1H), 8.346 (d, J=4.5, 2H), 7.200-7.364 (m, 3H), 6.794 (S, 1H), 6.542 (t, J=4.5, 1H), 3.999 (t, J=5.0, 4H), 3.808 (t, J=5.0, 4H), 2.909 (s, 4H).

Example 6

Preparation of 5,6-dihydro-3-(4-phenylpiperazin-1-yl)benzo[h]cinnoline (MW01-3-173WH)

A mixture of comprising about 0.01 mol of 3-chloro-5,6-dihydrobenzo[h]cinnoline, about 0.05 mol of 1-phenylpiperazine and about 0.01 mol of ammonium hydrochloride was prepared in about 15 ml of 1-BuOH. The mixture was stirred at 130° C. for 48 h, and then the solvent was removed under reduced pressure. The remaining residue was then extracted with ethyl acetate, washed with water and brine, dried over anhydrous $Na_2SO_4$. Removal of solvent followed by recrystallization from 95% ethanol yielded bright yellow crystals, yield 88.1%; HPLC: 96.0% purity; HRMS calculated 342.1839, found 342.1831; 1H NMR (CDCl3): δ 8.474 (d, J=7.5, 1H), 7.222-7.400 (m, 4H), 7.012 (d, J=10, 2H), 6.925 (t, J=6.5, 3=7.5, 1H), 6.824 (S, 1H), 3.900 (s, 4H), 3.370 (d, J=4.5, 4H), 2.932 (s, 4H).

Example 7

Preparation of 5,6-dihydro-3-(4-(pyridm-2-yl)piperazin-1-yl)benzo[h]cinnoline (MW01-3-202WH)

A mixture of comprising about 0.01 mol of 3-chloro-5,6-dihydrobenzo[h]cinnoline, about 0.05 mol of 1-(pyridin-2-yl)piperazine and about 0.01 mol of ammonium hydrochloride was prepared in about 15 ml of 1-BuOH. The mixture was stirred at 130° C. for 48 h, and then the solvent was removed under reduced pressure. The remaining residue was then extracted with ethyl acetate, washed with water and brine, dried over anhydrous $Na_2SO_4$. Removal of solvent followed by recrystallization from 95% ethanol yielded light yellow crystals, yield 81.1%; HPLC: 96.4% purity; HRMS calculated 343.1791, found 343.1787; 1H NMR (CDCl3): 5 8.452 (d, J=7.5, 1H), 8.232 (s, 1H), 7.211-7.534 (m, 4H), 6.794 (s, 1H), 6.678-6.731 (m, 2H), 3.862 (d, J=4.0, 4H), 3.745 (d, J=4.0, 4H), 2.918 (s, 4H).

Example 8

Preparation of N-isopropyl-3-(4-(pyrimidin-2-yl) piperazin-1-yl)benzo[h]cinnoline-4-carboxamide (MW01-5-184WH)

Figure 7:
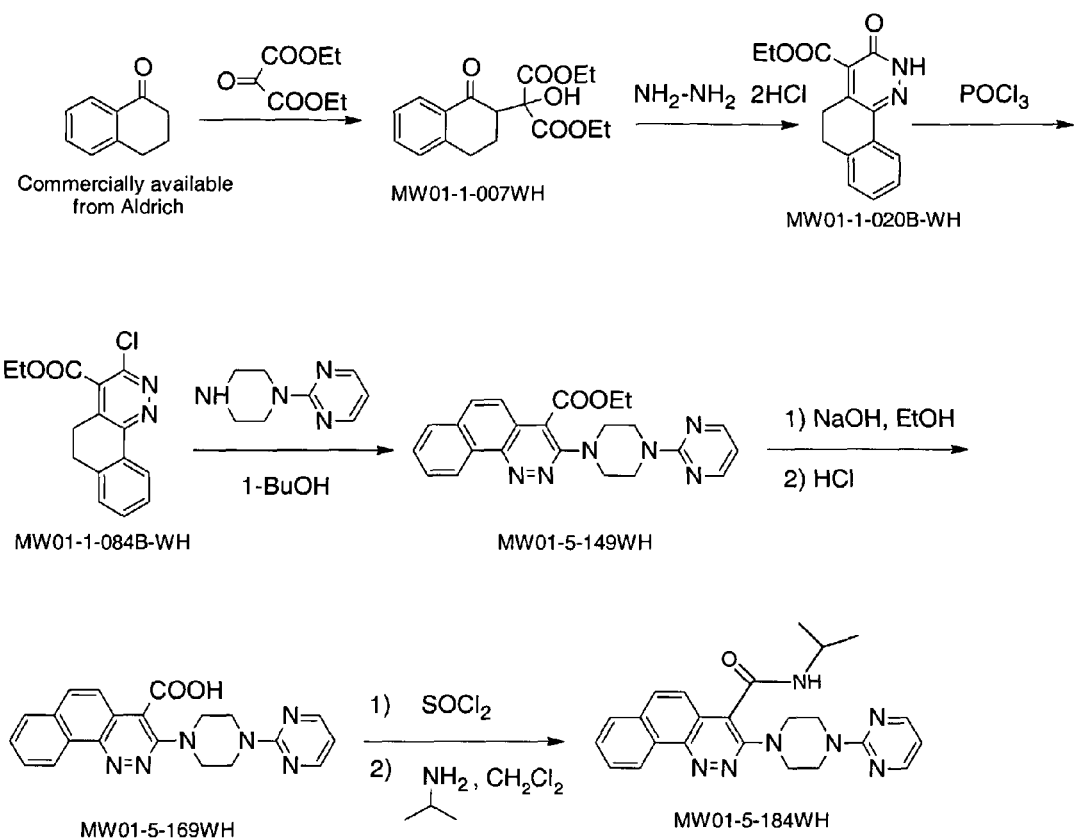
FIG. 7 is a synthetic scheme for the preparation of MW01-5-184WH.

A general synthetic scheme is depicted in FIG. 7, and the various step were carried as described herein.

Diethyl 2-(1,2,3,4-tetrahydro-1-oxonaphthalen-2-yl)-2-hydroxymalonate (MW01-1-007WH)

A mixture of the required tetralone (0.01 mol) and diethyl mesoxalate (0.014 mol) was heated at 100° C. for 12 h. After cooling, the reaction mixture was purified by silica gel chromatography, eluting with cyclohexane/ethyl acetate (8/2), to give the white crystals. Yield 70.4%. ESI-MS: m/z 321.1 (M+H$^+$).

Ethyl 2,3,5,6-tetrahydro-3-oxobenzo[h]cinnoline-4-carboxylate (MW01-1-020B-WH)

A mixture of the required diester MW01-1-007WH (0.01 mol) and hydrazine dihydrochloride (0.01 mol) in ethanol (60 ml) was refluxed for 24 h. After cooling, the solvent was evaporated and the residue brought to pH 7 with 5% sodium bicarbonate and extracted with dichloromethane (3×30 mL). After drying with anhydrous $Na_2SO_4$ and evaporation of the solvent, the product was isolated by silica gel chromatography, eluting with dichloromethane/methanol (95/5). Yield 12.2%. ESI-MS: m/z 271.1 (M+H$^+$).

Ethyl 3-chloro-5,6-dihydrobenzo[h]cinnoline-4-carboxylate (MW01-1-084B-WH)

0.01 mol of the substituted pyridazinone MW01-1-020B-WH was suspended in 20 mL of phosphorus oxychloride. The suspension was heated at about 90,ã for 2 h, then cooled to room temperature and poured onto 400 g of ice. The mixture was stirred for 20 min while green yellow solid was precipitated. The solid was filtered off and washed with water, dried over filter funnel in vacuo. The solid was then purified by crystallization from 95% ethanol to give white crystals. Yield 87.0%. ESI-MS: m/z 289.1 (M+H$^+$).

Ethyl 3-(4-(pyrimidin-2-yl)piperazin-1-yl)benzo[h] cinnoline-4-carboxylate (MW01-5-149WH)

A mixture of 1.0 equiv. of MW01-5-149WH, 2.5 equiv. of 2-(piperidin-4-yloxy)pyrimidine Dihydrochloride, 2.5 equiv. of triethylamine and 1.0 equiv. of the ammonium hydrochloride in 10 ml of 1-BuOH was heated at 130° C. under argon with magnetic stirring for 48 h. The solvent was removed under reduced pressure. The residue was then extracted with ethyl acetate, washed with water and brine, and dried over $MgSO_4$. After solvent was evaporated, the product was crystallized from the 95% ethanol to give gold yellow crystals. Yield 75%. ESI-MS: m/z 415.2 (M+H$^+$).

3-(4-(pyrimidin-2-yl)piperazin-1-yl)benzo[h]cinnoline-4-carboxylic acid (MW01-5-169WH)

NaOH solution (2M) was made by dissolving 2 g of NaOH solid in 25 ml of anhydrous EtOH. 207 mg of MW01-5-149WH was dissolved in 20 ml of anhydrous EtOH, then 20 ml of 2N of NaOH/EtOH solution was added. The reaction mixture was stirred at room temperature for 4 h, then the solvent was removed by evaporation. The residue was treated with water and acidified to PH 5.0 with dilute HCl. The mixture was extracted with $CH_2Cl_2$. The organic layer was separated, dried over $Na_2SO_4$, then recrystallized from 90% ethanol. Yield 90%. ESI-MS: m/z 387.2 (M+H$^+$).

N-isopropyl-3-(4-(pyrimidin-2-yl)piperazin-1-yl) benzo[h]cinnoline-4-carboxamide MW01-5-184WH 50 mg of MW01-5-169WH was dissolved in 1 ml of anhydrous CH2Cl2, 200 µl of thionyl chloride was then added. The mixture was refluxed for 5 hours. The solvent was then removed by distillation, the residue was used directly in the next step. The residue thus obtained was dissolved in 2 ml of anhydrous THF, to which 38 mg of isopropylamine was added. The reaction vessel was then purged with argon and then sealed tightly. The mixture was stirred until the reaction was complete, generally about 1-4 hours. The completeness of the reaction was monitored by HPLC. The reaction mixture was then concentrated to dryness, treated with water and extracted with ethyl acetate. Removal of solvent was followed by recrystallization from 95% ethanol which yielded a yellow solid. Yield 81%. ESI-MS: m/z 428.2 (M+H$^+$)

The present invention is not to be limited in scope by the specific embodiments described herein, since such embodiments are intended as but single illustrations of one aspect of the invention and any functionally equivalent embodiments are within the scope of this invention. Indeed, various modifications of the invention in addition to those shown and described herein will become apparent to those skilled in the art from the foregoing description and accompanying drawings. Such modifications are intended to fall within the scope of the appended claims.

All publications, patents and patent applications referred to herein are incorporated by reference in their entirety to the same extent as if each individual publication, patent or patent application was specifically and individually indicated to be incorporated by reference in its entirety. All publications, patents and patent applications mentioned herein are incorporated herein by reference for the purpose of describing and disclosing the methods etc. which are reported therein which might be used in connection with the invention. Nothing herein is to be construed as an admission that the invention is not entitled to antedate such disclosure by virtue of prior invention.

TABLE 1

Improved Computed Molecular Properties of Second-Generation Anti-Neuroinflammatory Compound MW01-2-151WH

| Molecular Property | MW01-151WH | MW01-070C |
|---|---|---|
| Molecular Weight | 344.4 | 527.7 |
| H-bond donors (sum of OHs and NHs) | 0 | 1 |
| H-bond acceptors (sum of Ns and Os) | 6 | 8 |
| Polar surface area (PSA) value (Å$^2$) | 58.04 | 88.78 |
| Rotable Bonds | 2 | 12 |
| LogP | 3.06 ± 0.51 | 5.22 ± 0.81 |

TABLE 2

| Compound Structure | Synthesis ID |
|---|---|
| 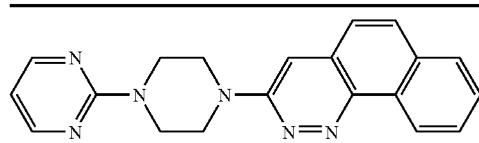 | MW01-2-151WH |
| 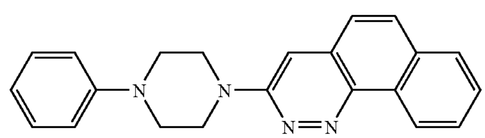 | MW01-3-173WH |
| 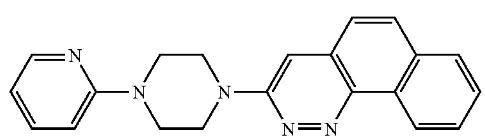 | MW01-2-202WH |

TABLE 3

| Compound Number | Compound Structure | Synthesis Code |
|---|---|---|
| 21 | 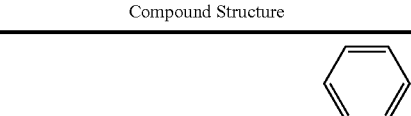 | MW01-1-17-L-G06 |

TABLE 3-continued

| Compound Number | Compound Structure | Synthesis Code |
|---|---|---|
| 28 | 5,6-dihydrobenzo[h]cinnolin-3-yl-NH-(CH₂)₃-N(CH₂CH₃)₂ | MW01-1-17-L-H10 |
| 57 | 3-oxo-2,3,5,6-tetrahydrobenzo[h]cinnoline-4-carboxylic acid | MW01-7-137Z |
| 98 | 3-amino-5,6-dihydrobenzo[h]cinnoline | MW01-8-103Z |
| 139 | ethyl 3-oxo-2,3,5,6-tetrahydrobenzo[h]cinnoline-4-carboxylate | MW01-1-020B-WH |
| 144 | 3-chloro-5,6-dihydrobenzo[h]cinnoline | MW01-2-141WH |
| 170 | 5,6-dihydrobenzo[h]cinnolin-3-yl-NH-CH₂CH₂-morpholine | MW01-5-152WH |
| 182 | benzo[h]cinnolin-3-yl-NH-CH₂CH₂-morpholine | MW01-5-154WH |

TABLE 3-continued
| Compound Number | Compound Structure | Synthesis Code |
|---|---|---|
| 193 | 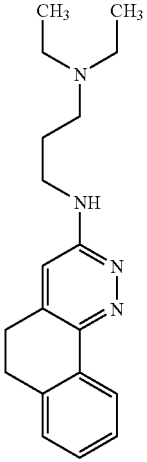 | MW01-1-17-L-H10 |
| 195 | 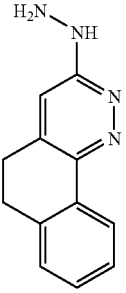 | MW01-2-03-L-F03 |
| 196 | 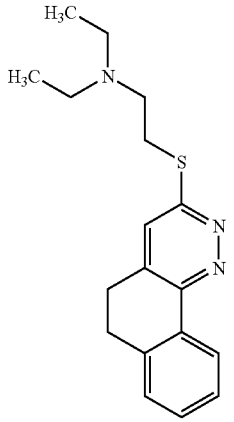 | MW01-3-06-L-F03 |
| 353 | 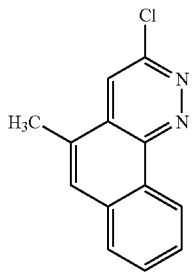 | MW01-1-04-L-D04 |

TABLE 3-continued

| Compound Number | Compound Structure | Synthesis Code |
|---|---|---|
| 354 | 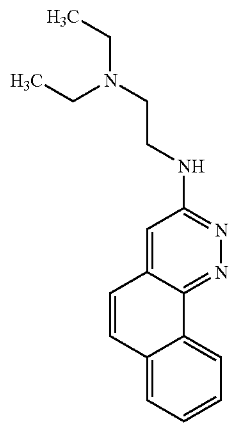 | MW01-3-101-L-F02 |

TABLE 4

| Compound Number | Compound Structure | Synthesis Code |
|---|---|---|
| 27 | 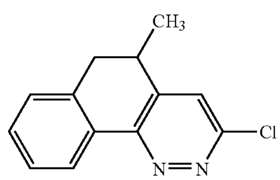 | MW01-1-04-L-C11 |
| 58 | 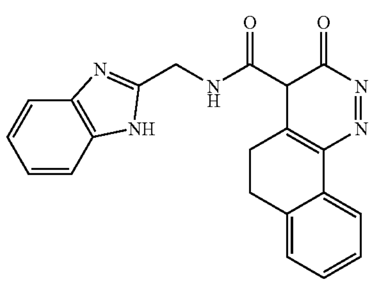 | MW01-7-144Z |
| 59 | 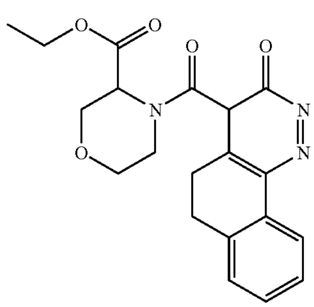 | MW01-7-168Z |

TABLE 4-continued
| Compound Number | Compound Structure | Synthesis Code |
|---|---|---|
| 77 | 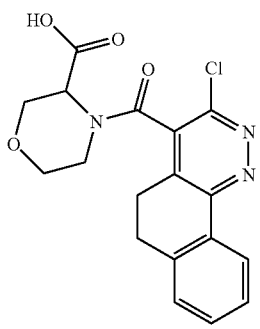 | MW01-7-171Z |
| 78 | 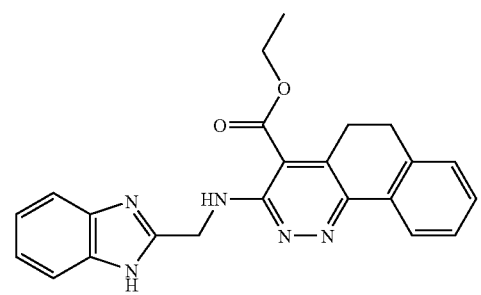 | MW01-7-203Z |
| 79 | 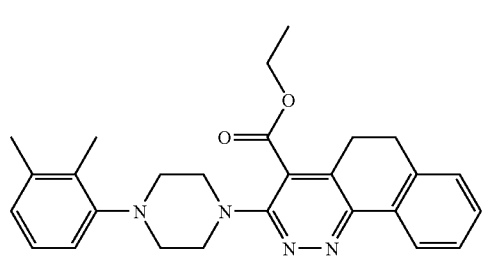 | MW01-7-204Z |
| 80 | 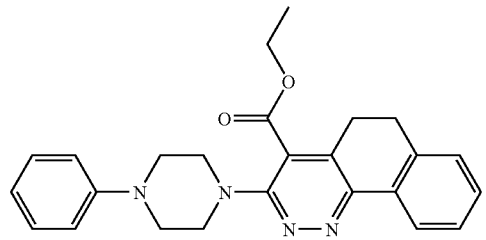 | MW01-8-052Z |
| 81 | 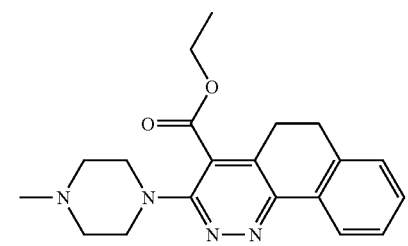 | MW01-8-054Z |

TABLE 4-continued
| Compound Number | Compound Structure | Synthesis Code |
|---|---|---|
| 82 | 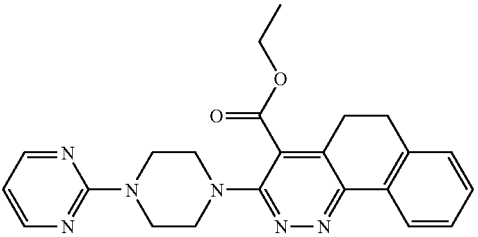 | MW01-8-056Z |
| 83 | 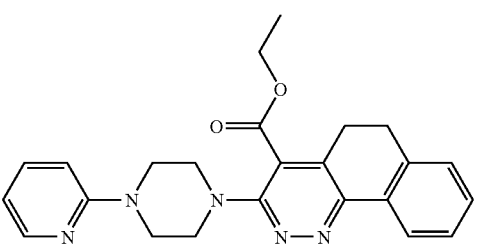 | MW01-8-093Z |
| 84 | 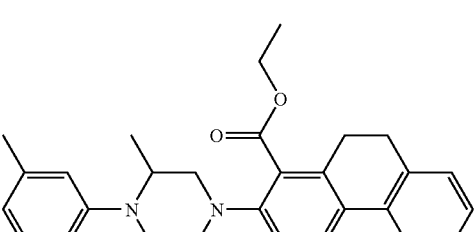 | MW01-8-094Z |
| 85 | 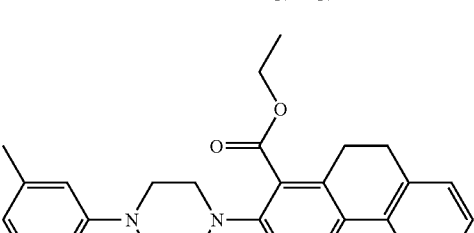 | MW01-8-096Z |
| 86 | 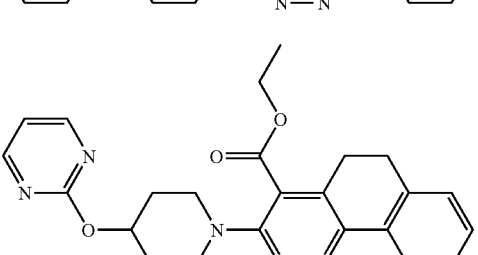 | MW01-3-153WH |
| 100 | 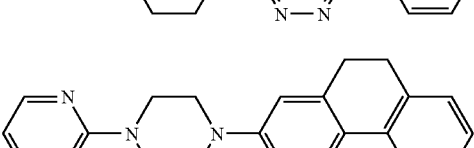 | MW01-3-202WH |
| 101 | 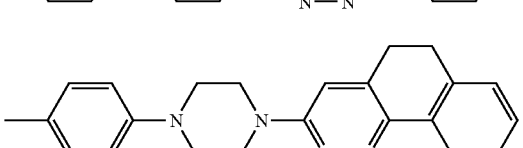 | MW01-9-004Z |

TABLE 4-continued

| Compound Number | Compound Structure | Synthesis Code |
|---|---|---|
| 103 | 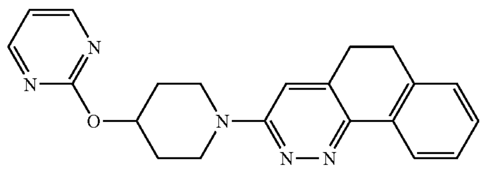 | MW01-9-006Z |
| 104 | 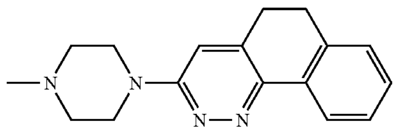 | MW01-9-007Z |
| 117 | 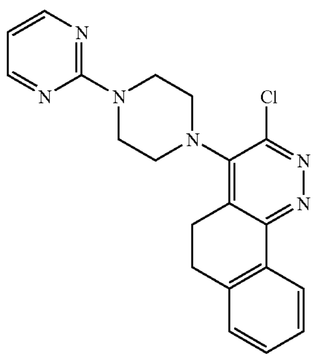 | MW01-1-126A-SRM |
| 119 | 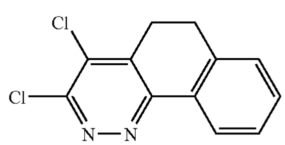 | MW01-1-042SRM |
| 131 | 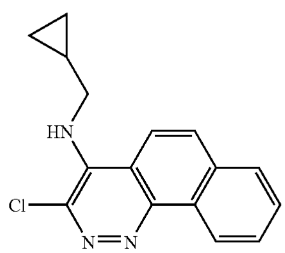 | MW01-1-150A-SRM |
| 132 | 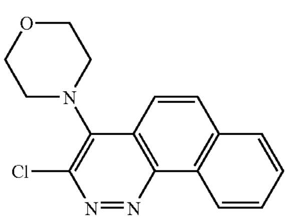 | MW01-1-161B-SRM |
| 133 | 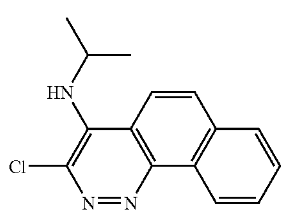 | MW01-1-166B-SRM |

TABLE 4-continued
| Compound Number | Compound Structure | Synthesis Code |
|---|---|---|
| 134 | 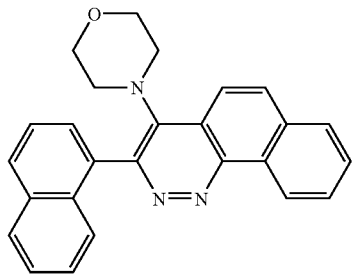 | MW01-1-194SRM |
| 135 | 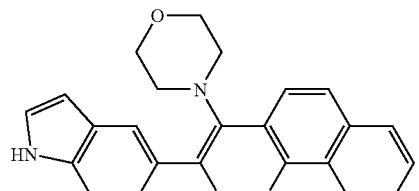 | MW01-1-195SRM |
| 141 | 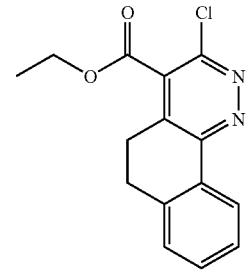 | MW01-1-188B-WH |
| 142 | 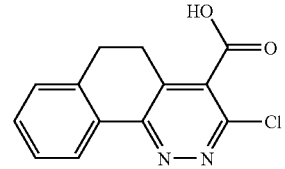 | MW01-1-201WH |
| 145 | 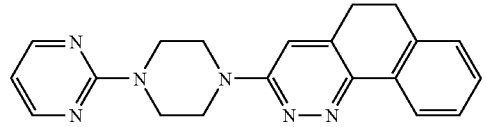 | MW01-2-151WH |
| 165 | 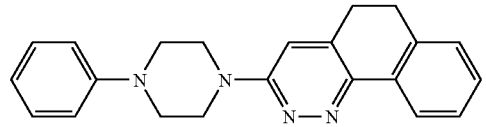 | MW01-3-173WH |
| 167 | 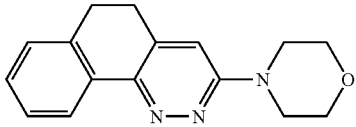 | MW01-5-147AB-WH |

TABLE 4-continued

| Compound Number | Compound Structure | Synthesis Code |
|---|---|---|
| 168 | 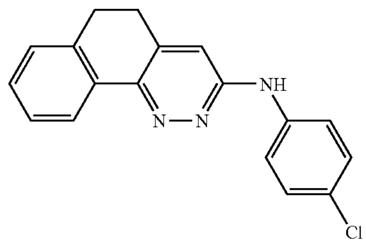 | MW01-5-148WH |
| 169 | 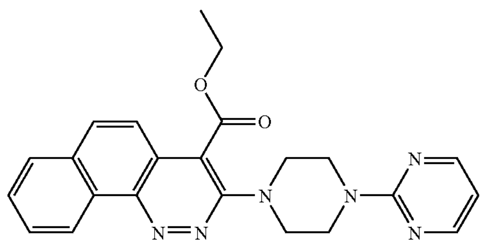 | MW01-5-149WH |
| 185 | 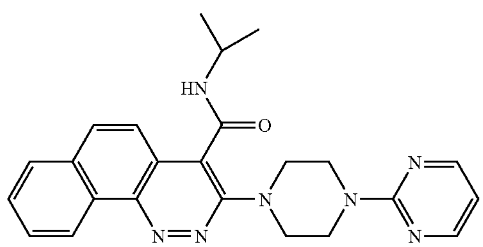 | MW01-5-184WH |
| 187 | 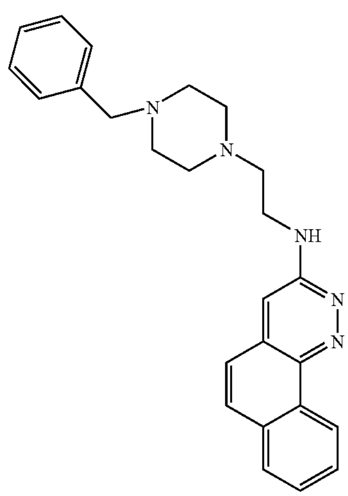 | MW01-5-193A-WH |
| 194 | 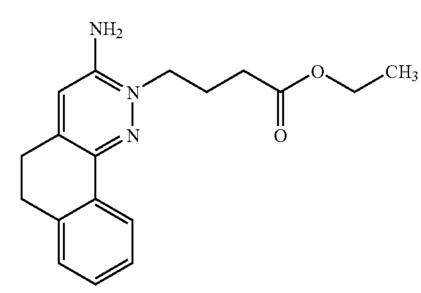 | MW01-2-03-L-A06 |

TABLE 4-continued

| Compound Number | Compound Structure | Synthesis Code |
|---|---|---|
| 370 | 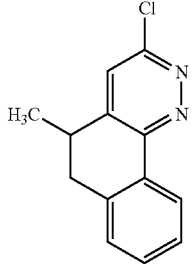 | MW01-1-04-L-C11 |
| 383 | 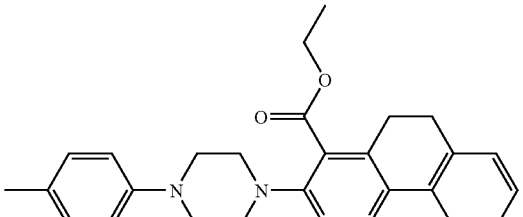 | MW01-8-095Z |

What is claimed is:

1. A compound of the formula I

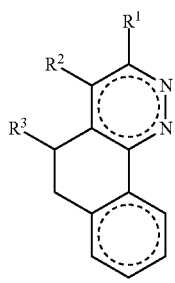

wherein $R^1$ is a heterocyclic group which may have one or more substituents, $R^2$ is hydrogen, an alkoxy carbonyl or an alkylamino carbonyl, and $R^3$ is hydrogen or alkyl.

2. A compound of the formula I according to claim 1 wherein $R^1$ is pyrrolidinyl, imidazolidinyl, piperidinyl, or piperazinyl, each of which may be substituted.

3. A compound of the formula I according to claim 2 wherein the pyrrolidinyl, imidazolidinyl, piperidinyl, or piperazinyl group is substituted with heteroaryl, aryl, alkyl, or a heterocyclic group each of which may be substituted.

4. A compound of the formula I according to claim 2 wherein $R^1$ is piperazinyl substituted with a substituted or unsubstituted pyrimidinyl, pyridyl or pyridinyl; with aryl or substituted aryl; or with alkyl.

5. A compound of the formula I according to claim 1 wherein $R^1$ is piperazinyl substituted with pyrimidinyl, and $R^2$ is hydrogen, methoxy carbonyl, ethoxy carbonyl, isopropoxy carbonyl, t-butoxycarbonyl, t-pentyloxycarbonyl, or heptyloxy carbonyl, or alkylamino carbonyl, and $R^3$ is hydrogen.

6. A compound of the formula I according to claim 1 wherein $R^1$ is piperazinyl substituted with one or more of alkyl, phenyl, substituted phenyl, pyrimidinyl, substituted pyrimidinyl, or pyridinyl.

7. A pharmaceutical composition comprising a compound of the formula I according to claim 1, and a pharmaceutically acceptable carrier, excipient, or vehicle.

8. A kit comprising one or more compounds of the formula I according to claim 1 for preventing and/or treating a disease, a container, and instructions for use.

9. A compound of the formula I:

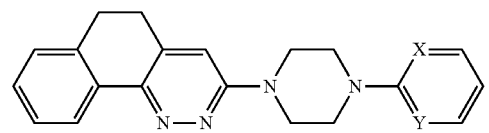

wherein X and Y are each independently N or CH; or a pharmaceutically acceptable salt thereof.

10. A compound of claim 9 wherein X and Y are N.

11. A compound of claim 9 wherein X and Y are CH.

12. A compound of claim 9 wherein X is N and Y is CH.

13. A pharmaceutical composition comprising a compound of the formula I according to claim 9, and a pharmaceutically acceptable carrier, excipient, or vehicle.

* * * * *

UNITED STATES PATENT AND TRADEMARK OFFICE
CERTIFICATE OF CORRECTION

| | | |
|---|---|---|
| PATENT NO. | : 8,063,047 B2 | Page 1 of 1 |
| APPLICATION NO. | : 12/119208 | |
| DATED | : November 22, 2011 | |
| INVENTOR(S) | : D. Martin Watterson et al. | |

It is certified that error appears in the above-identified patent and that said Letters Patent is hereby corrected as shown below:

On the Title Page:

Item (75) Inventors:

"Martin Watterson, Chicago, IL (US)" should read as -- D. Martin Watterson, Chicago, IL (US) --;

"Linda Van El Dik, Chicago, IL (US)" should read as -- Linda Van Eldik, Chicago, IL (US) --;

"Anastasia Veleniza, San Diego, CA (US)" should read as -- Anastasia Velentza, San Diego, CA (US) --;

"Magdaena Zasadzki, Chicago, IL (US)" should read as -- Magdalena Zasadzki, Chicago, IL (US) --.

PCT filing information is added, as follows:

Item (22)     PCT Filed: Nov. 2, 2005

Item (86)     PCT No.:   PCT/US2005/039476

Item (87)     PCT Pub. No.: WO 2006/050359
              PCT Pub. Date: May 11, 2006

Signed and Sealed this
Twenty-fourth Day of July, 2012

David J. Kappos
*Director of the United States Patent and Trademark Office*